United States Patent
Cheshire et al.

(12)

(10) Patent No.: US 6,300,352 B1
(45) Date of Patent: Oct. 9, 2001

(54) PYRIDINE DERIVATIVES AND PHARMACEUTICAL COMPOSITIONS CONTAINING THEM

(75) Inventors: David Cheshire, Chilwell; David Cladingboel, Mountsorrel; Simon Hirst, West Bridgford; Carol Manners, Arnold; Michael Stocks, Long Eaton, all of (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/068,522
(22) PCT Filed: Mar. 20, 1998
(86) PCT No.: PCT/SE98/00505
  § 371 Date: May 11, 1999
  § 102(e) Date: May 11, 1999
(87) PCT Pub. No.: WO98/42670
  PCT Pub. Date: Oct. 1, 1998

(30) Foreign Application Priority Data

Mar. 25, 1997 (SE) .................................................. 9701100
Jun. 9, 1997 (SE) .................................................. 9702199
Nov. 28, 1997 (SE) .................................................. 9704403

(51) Int. Cl.$^7$ ..................... A61K 31/4406; C07D 213/24
(52) U.S. Cl. ..................... 514/357; 514/277; 514/235.5; 546/334; 546/336; 546/339; 546/340; 544/131
(58) Field of Search .................................... 546/339, 334, 546/340, 336; 514/277, 357, 235.5

(56) References Cited

U.S. PATENT DOCUMENTS 5,977,105 * 11/1999 Cheshire et al. ..................... 514/241

FOREIGN PATENT DOCUMENTS

| 0 264 114 A1 | 4/1988 | (EP) . |
| 0 267 439 A2 | 5/1988 | (EP) . |
| 97/20815 | 6/1997 | (WO) . |

* cited by examiner

Primary Examiner—Jane Fan
(74) Attorney, Agent, or Firm—Nixon & Vanderhye

(57) ABSTRACT

The invention relates to novel pyridyl derivatives, their use as medicaments, pharmaceutical formulations containing them and methods for their preparation.

10 Claims, No Drawings

PYRIDINE DERIVATIVES AND PHARMACEUTICAL COMPOSITIONS CONTAINING THEM

This Application is A 371 of PCT/SE98/00505 Mar. 20, 1998.

This invention relates to novel pyridyl derivatives, their use as medicaments, pharmaceutical formulations including them and methods for their preparation.

European Patent Applications EP-A-0 264 114 and EP-A-0 267 439 disclose certain phenylalkyl- and phenylalkoxypyridine alkanol derivatives and their use as platelet-activating factor (PAF) antagonists.

A series of structurally distinct compounds have now been found to be useful for the modulation of inflammatory conditions. In a first aspect the present invention therefore provides a compound of formula I:

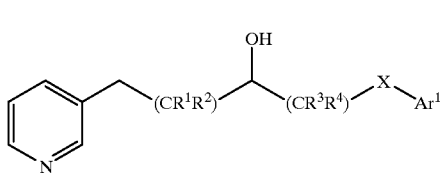

(I)

wherein:

X is O or S;

$R^1$ and $R^2$ are independently hydrogen, $C_{1-6}$ alkyl or $C_{3-6}$ cycloalkyl or $R^1$ and $R^2$ together with the carbon atom to which they are attached form a $C_{3-6}$ cycloalkyl group;

$R^3$ is hydrogen, and $R^4$ is $C_{1-6}$ alkyl or $C_{3-6}$ cycloalkyl or $R^3$ and $R^4$ together with the carbon atom to which they are attached form a $C_{3-6}$ cycloalkyl group;

$Ar^1$ is indanyl, tetrahydronaphthyl, naphthyl, phenyl, $C_{7-9}$ alkylphenyl or biphenyl, which latter four groups can be optionally substituted by one or more groups selected from halo, nitro, cyano, pyridyl, thiazinyl, $C_{1-10}$ alkyl (optionally substituted by one or more fluorine atoms), —Y—$OR^5$, —Y—$NR^6C(O)NR^7$—$R^8$, —O—Z—$C(O)NR^7R^8$, —O—Y—$C(S)NR^7R^8$, —Y—$C(O)NR^7R^8$, —Y—$SO_2NR^7R^8$, —Y—$NR^7R^8$, —Y—$OC(O)NR^7R^8$, —Y—$C(S)NR^7R^8$, —Y—$C(O)R^9$, —Y—$OC(O)R^9$, —Y—$CO_2R^9$, Y—$NR^{10}C(O)NR^{11}$—Z—$R^{12}$, $SO_2NR^{10}C(O)NR^7R^8$, —Y—$SO_2NHNR^7R^8$, —Y—$C(O)NR^{11}$—Z—$R^{12}$, —Y—$C(S)NR^{11}$—Z—$R^{12}$, —Y—$N(R^{10})SO_2R^{11}$, —Y—$N(R^{10})C(O)R^{11}$ or —Y—$N(R^{10})CO_2R^{11}$;

where:

Y is a bond, $C_{1-6}$ alkylene or $C_{2-6}$ alkenylene;

$R^7$ and $R^8$ are independently hydrogen or $C_{1-6}$ alkyl or together with the nitrogen atom to which they are attached form an optionally substituted 5- to 7-membered heterocyclic ring optionally containing a further heteroatom selected from nitrogen, oxygen or sulfur;

$R^5$, $R^6$, $R^9$, $R^{10}$ and $R^{11}$ are independently hydrogen or $C_{1-10}$ alkyl (optionally substituted by one or more fluorine atoms);

Z is $C_{1-6}$ alkylene; and $R^{12}$ is a group $NR^{10}C(O)R^{11}$, $NR^{10}CO_2R^{11}$, $OR^5$, $NR^7R^8$ or $CO_2R^{13}$ where $R^5$, $R^7$, $R^8$, $R^{10}$ and $R^{11}$ are as defined above and $R^{13}$ is hydrogen, $C_{1-6}$ alkyl, $C_{1-6}$ alkylaryl or aryl optionally substituted by hydroxy, or a salt or solvate thereof.

Alkyl, alkylene, alkenyl and alkenylene groups, whether alone or part of another group, can be straight chained or branched.

Suitably X is O or S, preferably X is O.

Suitably $R^1$ and $R^2$ are independently hydrogen, $C_{1-6}$ alkyl or $C_{3-6}$ cycloalkyl or $R^1$ and $R^2$ together with the carbon atom to which they are attached form a spiro linked $C_{3-6}$ cycloalkyl group. Preferably $R^1$ and $R^2$ are both hydrogen.

Suitably $R^3$ is hydrogen, and $R^4$ is $C_{1-6}$ alkyl or $C_{3-6}$ cycloalkyl or $R^3$ and $R^4$ together with the carbon atom to which they are attached form a $C_{3-6}$ cycloalkyl group. Preferably $R^3$ is hydrogen and $R^4$ is $C_{1-6}$ alkyl, in particular methyl, ethyl or isopropyl or $R^3$ and $R^4$ together with the carbon atom to which they are attached form a cyclopropyl group.

Suitably $Ar^1$ is indanyl, tetrahydronaphthyl, naphthyl, phenyl, $C_{7-9}$ alkylphenyl or biphenyl, which latter four groups can be optionally substituted by one or more groups selected from halo, nitro, cyano, pyridyl, thiazinyl, $C_{1-10}$ alkyl (optionally substituted by one or more fluorine atoms), —Y—$OR^5$, —Y—$NR^6C(O)NR^7$—$R^8$, —O—Z—$C(O)NR^7R^8$, —O—Y—$C(S)NR^7R^8$, —Y—$C(O)NR^7R^8$, —Y—$SO_2NR^7R^8$, —Y—$NR^7R^8$, —Y—$OC(O)NR^7R^8$, —Y—$C(S)NR^7R^8$, —Y—$C(O)R^9$, —Y—$OC(O)R^9$, —Y—$CO_2R^9$, —Y—$NR^{10}C(O)NR^{11}$—Z—$R^{12}$, $SO_2NR^{10}C(O)NR^7R^8$, —Y—$SO_2NHNR^7R^8$, —Y—$C(O)NR^{11}$—Z—$R^{12}$, —Y—$C(S)NR^{11}$—Z—$R^{12}$, —Y—$N(R^{10})SO_2R^{11}$, —Y—$N(R^{10})C(O)R^{11}$ or —Y—$N(R^{10})CO_2R^{11}$; where Y is a bond, $C_{1-6}$ alkylene or $C_{2-6}$ alkenylene. More than one substituent can be present on the $Ar^1$ group and multiple substituents can be the same or different.

Preferably $Ar^1$ is a naphthyl or a biphenyl group. Preferred sustituents for $Ar^1$ groups include those groups exemplified herein.

More preferably $Ar^1$ is biphenyl optionally substituted by one or more substituents selected from halo, cyano, alkyl or $SO_2NR^7R^8$. Most preferably $Ar^1$ is biphenyl substituted by cyano, halo, methyl or —$SO_2NH_2$.

Particularly preferred compounds of the invention include those exemplified herein in free base form as well as salts or solvates thereof.

Compounds of the invention can form pharmaceutically acceptable solvates and salts. The compounds of the formula (I) can form acid addition salts with acids, such as conventional pharmaceutically acceptable acids, for example maleic, hydrochloric, hydrobromic, phosphoric, acetic, fumaric, salicylic, citric, lactic, oxalic, mandelic, tartaric and methanesulfonic acids. Compounds of the invention may also form alkali metal salts such as magnesium, sodium, potassium and calcium salts.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

According to the invention there is also provided a process for the preparation of compounds of formula I which comprises:

(a) reduction of a compound of formula (II):

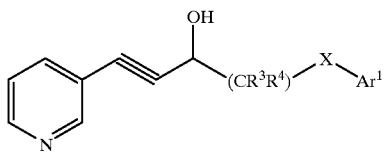

(II)

in which $R^3$, $R^4$, X and $Ar^1$ are as defined in formula (I); or
(b) reduction of a compound of formula (III):

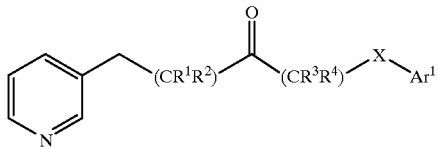

(III)

in which $R^1$, $R^2$, $R^3$, $R^4$, X and $Ar^1$ are as defined in formula (I); or
(c) preparation of compounds of formula (I) where $Ar^1$ is a substituted biphenyl group by reaction of a compound of formula (IV):

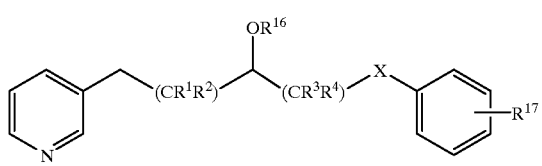

(IV)

with a compound of formula (V):

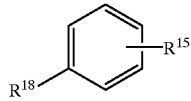

(V)

where X, $R^1$, $R^2$, $R^3$, and $R^4$ are as defined in formula (I), $R^{15}$ is an $Ar^1$ substituent as defined in formula (I), and $R^{16}$ is a suitable hydroxy protecting group, and one of $R^{17}/R^{18}$ is triflate or halo and the other is $B(OH)_2$ or ZnHal, or and optionally thereafter in any order:
removing any protecting groups
converting a compound of formula (I) into another compound of formula (I)
forming a pharmaceutically acceptable salt or solvate.

Reduction of compounds of formula (II) is carried out using conventional procedures, for example by hydrogenation using a palladium catalyst in an inert solvent such as ethyl acetate. Reduction of compounds of formula (III) is carried out using conventional procedures, for example using sodium or zinc borohydride or other reducing agents in a suitable solvent such as ethanol.

Process (c) is carried out under the conditions of the Suzuki reaction (*Synthetic Communications* 11(7), 513–519, 1081) for example at about 100° C. in the presence of a suitable catalyst and base (e.g. tetrakis(triphenylphosphine) palladium (0) and aqueous sodium carbonate) in a suitable solvent (e.g. ethanol/toluene).

Compounds of formula (II) can be prepared by oxidation of a compound of formula (VI):

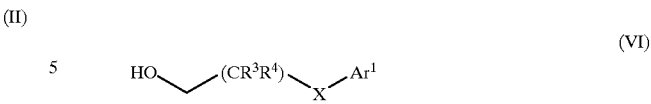

(VI)

in which X, $Ar^1$, $R^3$ and $R^4$ are as defined in formula (I) followed by reaction of the resulting aldehyde with a compound of formula (VII):

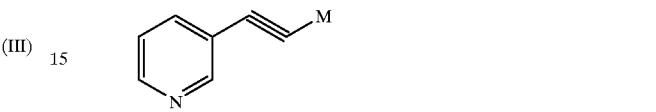

(VII)

in which M is lithium, sodium, potassium, MgX' or ZnX' where X' is halogen optionally in the presence of additives such as boron trifluoride.

Oxidation of a compound of formula (VI) can be carried out under conventional conditions, for example by Swern oxidation.

Compounds of formula (VI) can be prepared by reduction of a compound of formula (VIII):

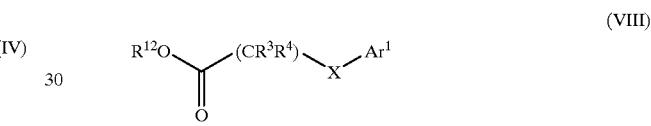

(VIII)

in which X, $Ar^1$, $R^3$ and $R^4$ are as defined in formula (VI) and $R^{19}$ is hydrogen $C_{1-6}$ alkyl or benzyl using a suitable reducing agent such as lithium aluminium hydride or diborane.

Compounds of formula (VIII) can be prepared from compounds of formula (IX):

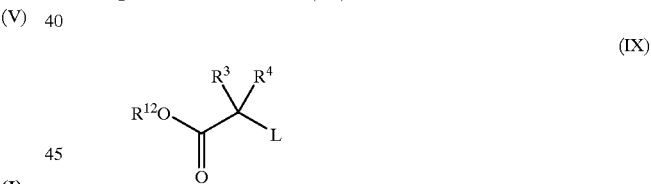

(IX)

in which $R^{19}$, $R^3$ and $R^4$ are as defined in formula (VIII) and L is a leaving group such as halogen or a group which can be activated to subsequently act as a leaving group, for example hydroxy, with a compound of formula (X):

$Ar^1$—OH (X)

in which $Ar^1$ is as defined in formula (I). The reaction is carried out in the presence of a base such as potassium or cesium carbonate in an inert solvent such as dimethylformamide or acetone.

Compounds of formula (VIII) can also be prepared using Mitsonobu chemistry using a compound of formula (IX) wherein L is hydroxy.

Compounds of formula (IX) are commercially available or can be prepared using standard procedures. For example when L is hydroxy compounds of formula (IX) can be prepared by diazotization of commercially available amino acids. The compounds of formula (IX) where $R^{19}$ is hydrogen or $C_{1-6}$ alkyl and one of $R^3/R^4$ is hydrogen and the other is methyl are available as lactic acid or esters thereof.

Compounds of formula (IV) are prepared from a compound of formula (XI):

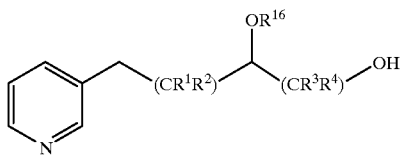

in which $R^1$, $R^2$, $R^3$, $R^4$, and $R^{16}$ are as defined above by reaction with a compound of formula (XII):

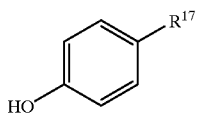

in which $R^{17}$ is triflate or halogen,

The reaction is carried out under the conditions of the Mitsonobu reaction for example at approximately 0–25° C. in the presence of diethyl azodicarboxylate and triphenylphosphine in an appropriate solvent (e.g. toluene).

Compounds of formula (XI) can be prepared by reduction of a compound of formula (XIII) using conventional procedures, for example hydrogenation using a palladium catalyst in an inert solvent such as ethyl acetate, followed by debenzylation using conventional methods such as thos described in 'Protective Groups in Organic Synthesis', 2nd Edition, T. W. Greene & P. G. M. Wuts, Wiley-Interscience (1991).

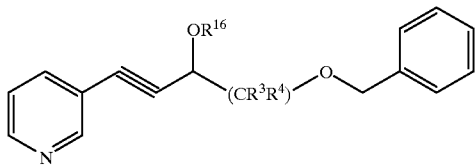

Compounds of formula (XIII) can be prepared by the reaction of compound (XIV) in which $R^3$ and $R^4$ are as defined in formula (I) reported by Reetz et. al. Angew. Chem. Suppl., (1983), 1511.) with a compound of formula (VII):

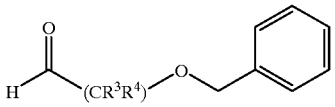

in which $R^3$ and $R^4$ are as defined in formula (I).

Compounds of formula (I) can be converted into further compounds of formula (I) using standard procedures. For example compounds of formula (I) where the $A^1$ group is substituted by bromo can be converted to compounds of formula (I) where the $Ar^1$ group is substituted by —CH=CH—$R^{20}$ where Y is CH=CH and $R^{20}$ is a group —$NR^6C(O)NR^7$—$R^8$, —$C(O)NR^7R^8$, —$NR^7R^8$, —$C(O)OR^9$, —$NR^{10}C(O)NR^{11}$—Z—$R^{12}$, or —$C(O)NR^{11}$—Z—$R^{12}$ where $R^6$, $R^7$, $R^8$, $R^9$, $R^{10}$, $R^{11}$ and $R^{12}$ are as defined in formula (I) by reacting with compounds of formula (XV):

$$H_2C=CH-R^{20} \quad (XV)$$

where $R^{20}$ is as defined above using Heck chemistry. For example compounds of formula (I) where $Ar^1$ is naphthyl substituted by bromo or iodo can be treated with a palladium catalyst and a compound of formula (XV) in a suitable solvent at elevated temperature. If desired the palladium catalyst can be formed in situ.

The resulting compounds of formula (I) prepared using the above chemistry can be converted into yet further compounds of formula (I) by reduction of the double bond of the —CH=CH—$R^{20}$ group. This can be carried out under standard hydrogenation conditions, for example using palladium on charcoal.

Other procedures for converting compounds of formula (I) into further compounds of formula (I) will be apparent to those skilled in the art. For example compounds of formula (I) containing a —Y—$C(O)OR^9$ group where $R^1$ is methyl can be converted to compounds of formula (I) having a —Y—C(O)NHMe group by treating with methylamine in methanol at elevated temperature. Preferably the reaction is carried out at about 100° C. in a sealed vessel. The same transformation can be carried out using trimethylaluminium and methylamine hydrochloride in toluene at reduced temperature, e.g. at about 0° C.

Compounds of formula (I) containing a —Y—$C(O)OR^9$ group can also be converted to the corresponding carboxylic acids by hydrolysis. Preferred conditions include treatment with lithium hydroxide in a suitable solvent system, for example in water/THF at ambient temperature.

Compounds of formula (I) containing a —Y—C(O)OH group can also be converted to compounds of formula (I) having a —Y—$C(O)NR^7R^8$ group by reacting with the appropriate amine. For example amines of formula $HNR^7R^8$ can be reacted in a suitable solvent such as DMF in the presence of 1-hydroxybenzotriazole and 1-ethyl-3-(3'-dimethylaminopropyl)-carbodiimide.

Compounds of formula (I) containing a —Y—C(O)$NR^7R^8$ group can be converted to compounds of formula (I) having a —Y—$NR^7R^8$ group by treating with borane-tetrahydrofuran complex.

An alternative synthesis of compounds of formula (II) is via (a) selective reduction of compounds of formula (XVI):

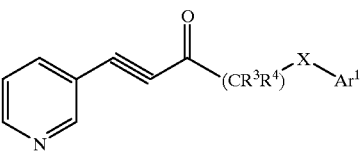

in which $R^3$, $R^4$, X and $Ar^1$ are as defined in formula (I). Suitable reducing agents include sodium borohydride or zinc borohydride (Tetrahedron Lett., (1985), 26, 4463).

The triple bond in compounds of formula (XVI) can also be reduced to form compounds of formula (III) using conventional procedures, for example hydrogenation using a palladium catalyst in an inert solvent such as ethyl acetate.

Compounds of formula (XII) can be prepared by reacting a compound of formula (VIII) as defined above with a compound of formula (VII) as hereinbefore defined.

Intermediate compounds described above are either prepared as described above, are commercially available, or may be prepared conveniently using known techniques. Certain intermediate compounds are novel and form a further aspect of the invention.

It will be appreciated by those skilled in the art that in the process described above the functional groups of intermediate compounds may need to be protected by protecting groups.

Functional groups which it is desirable to protect include hydroxy, amino and carboxylic acid. Suitable protecting groups for hydroxy include organosilyl groups (e.g. tert-butyldimethylsilyl, tert-butyldiphenylsilyl or trimethylsilyl), benzyl and tetrahydro-pyranyl. Suitable protecting groups for amino include tert-butoxycarbonyl or benzyloxy carbonyl. Suitable protecting groups for carboxylic acid include $C_{1-6}$ alkyl or benzyl esters. The protection and deprotection of functional groups may take place before or after a reaction step.

The use of protecting groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wutz, Wiley-Interscience (1991).

The compounds of the invention are useful because they possess pharmacological activity and more particularly activity in the modulation of inflammatory and allergic conditions, for example as shown in the test described below. The compounds of the invention inhibit the activation of a range of cell types from haematopoetic lineage, including mast cells, neutrophils and eosinophils. In a further aspect the invention therefore provides a compound of formula (I) or a pharmaceutically acceptable salt or solvate thereof for use in therapy.

The compounds of the invention are indicated for use in the treatment or prevention of allergic, inflammatory, auto-immune, proliferative and hyper-proliferative diseases.

The compounds of the invention are also indicated in the treatment and prevention of allergic, inflammatory or auto-immune conditions of the lung, including reversible obstructive airways diseases which includes asthma (e.g. bronchial, allergic, intrinsic asthma, extrinsic and chronic asthma), and associated manifestations of the disease (late responses, hyper-responsiveness), also farmer's lung and related diseases, fibrosis, ideopathic interstitial pneumonia, chronic obstructive airways disease (COPD), bronchiectasis, cystic fibrosis, eosinophilic pneumonias, adult respiratory distress syndrome (ARDS), emphysema and alveolitis, for example cryptogenic fibrosing alveolitis.

Further, the compounds of the invention are indicated in the treatment or prevention of allergic, inflammatory or auto-immune conditions in the nose including all conditions characterised by inflammation of the nasal mucous membrane such as acute rhinitis, allergic rhinitis, atrophic rhinitis, chronic rhinitis including rhinitis caseosa, hypertrophic rhinitis, rhinitis purulenta and rhinitis sicca, rhinitis medicamentosa, membranous rhinitis including croupous, fibrinous and pseudomembranous rhinitis, scrofulous rhinitis, seasonal rhinitis including rhinitis nervosa (hay fever) and vasomotor rhinitis. Of particular interest are allergic rhinitis and seasonal rhinitis including rhinitis nervosa (hay fever). The compounds are also indicated for the treatment of nasal polyps and allergic menifestations of the nasopharynx other than those described hereintofore.

The compounds of the invention are also indicated the treatment or prevention of allergic, inflammatory or auto-immune conditions of the eye such as conjunctivitis (allergic, acute, vernal, of hay fever, chronic), inflammation disorders of the eyelids, cornea, uveal tract and retina.

The compounds of the invention are also indicated in the treatment and prevention of allergic, inflammatory and auto-immune conditions of the gastrointestinal tract such as food allergy and food intolerance, ulcerative colitis, Crohn's disease, irritable bowel disease, gastric ulcers, and food related allergic diseases which have symptomatic manifestations remote from the gastrointestinal tract, for example migraine, rhinitis and eczema.

The compounds of the invention are indicated for use in the treatment or prevention of allergic, inflammatory or auto-immune conditions of the skin such as psoriasis, atopical dermatitis, contact dermatitis/dermatitis herpetiformis, erythema nodosum, urticaria, cutaneous eosinophilias, acne, Alopecia areata, eosinophilic fascitis dermatomyositis, photoallergic sensitivity and periodontal disease.

The compounds of the invention are therefore indicated for use in the treatment or prevention of allergic, inflammatory or auto-immune conditions of the joints and connective tissue, including osteoarthritis, rheumatoid arthritis, systemic lupus erythematosis, vasculitis, Wegener's granulomatosis, polyarthritis nodosa, bursitis, tendonitis, gout, Behcet's syndrome, ankylosing sponditis, Reiter's syndrome and psoriatic arthritis.

The compounds of the invention are indicated in the treatment and prevention of allergic, inflammatory, and auto-immune conditions of the circulatory system including atheroma, reperfusion injury (e.g. on angioplasty), myocardial infarction, thrombosis and vascular and tissue damage caused by ischaemic disease or injury.

The compounds of the invention are indicated in the treatment and prevention of allergic, inflammatory or auto-immune conditions of the CNS including Parkinson's disease, Alzheimers and other dementias, stroke and subarachnoid haemorrhage. The compounds of the invention are indicated in the treatment and prevention of inflammatory conditions of the liver for example hepatitis, cirrhosis and glomerulonephritis.

The compounds of the invention are indicated in the treatment and prevention of allergic, inflammatory or auto-immune conditions of the bladder and uro-genital tract including cystitis.

The compounds of the invention are indicated in the treatment and prevention of tumours and other proliferative diseases.

Of particular interest amongst the above indications is use of the compounds of the invention in a reversible obstructive airways disease, most particularly asthma and especially the treatment and prophylaxis of asthmaand rhinitis.

According to a further aspect of the invention there is thus provided the use of a compound of formula I, as hereinbefore defined, or a pharmaceutically acceptable salt or solvate thereof in the manufacture of a medicament for the treatment of the above diseases, in particular reversible obstructive airways disease, especially the treatment and prophylaxis of asthma.

Administration of the compounds of the invention may be topical (for example by inhalation to the lung). The compounds of the invention may be inhaled as a dry powder which may be pressurised or non-pressurised.

In non-pressurised powder compositions, the active ingredient in finely divided form may be used in admixture with a larger sized pharmaceutically acceptable inert carrier.

The composition may alternatively be pressurised and contain a compressed gas, e.g. nitrogen, or a liquefied gas propellant. In such pressurised compositions, the active ingredient is preferably finely divided. The pressurised composition may also contain a surface active agent. The pressurised compositions may be made by conventional methods. The compounds of the invention may be administered systemically (for example by oral administration to the gastrointestinal tract). The active ingredient may be formulated together with known adjuvants, diluents or carriers using conventional techniques to produce tablets or capsules for oral administration to the gastrointestinal tract.

Examples of suitable adjuvants, diluents or carriers for oral administration in the form of tablets, capsules and dragees include microcrystalline cellulose, calcium phosphate, diatomaceous earth, a sugar such as lactose, dextrose or mannitol, talc, stearic acid, starch, sodium bicarbonate and/or gelatin.

According to a further aspect of the invention there is provided a pharmaceutical composition including a compound of formula I or a salt or solvate thereof as hereinbefore defined in association with a pharmaceutically acceptable adjuvant, diluent or carrier.

Suitable doses for such oral administration are in the range from 0.3 to 30 mg kg$^{-1}$ day$^{-1}$, for example 3 mg kg$^{-1}$ day$^{-1}$.

According to a further aspect of the present invention, there is provided a method of treatment or prophylaxis of a reversible obstructive airways disease, in particular asthma, which method comprises administration of a therapeutically effective amount of a compound of formula I as hereinbefore defined, or a pharmaceutically acceptable derivative thereof, to a person suffering from, or susceptible to, the disease.

The invention is illustrated by the following Examples.

EXAMPLE 1

(3R,4R)-4-(Biphenyl-4-yloxy)-1-pyridin-3-yl-pentan-3-ol and (3S,4R)-4-(biphenyl-4-yloxy)-1-pyridin-3-yl-pentan-3-ol

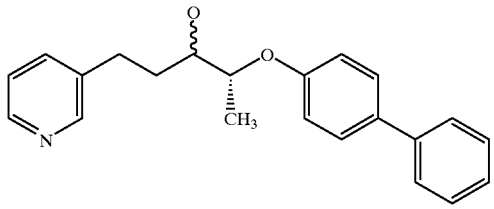

a) (2R)-2-(Biphenyl-4-yloxy)propionic acid, ethyl ester

Diethylazodicarboxylate (8.66 ml) in dry tetrahydrofuran (25 ml) was added dropwise over 30 minutes to a stirred solution of triphenylphosphine (13.11 g), (S)-(−)-ethyl lactate (5.67 ml) and 4-phenylphenol (8.51 g) in dry tetrahydrofuran (100 ml). The resulting solution was stirred at room temperature for 18 hours then concentrated under reduced pressure. A mixture of isohexane: ether (9:1) (200 ml) was added to the residue and stirred at room temperature for 30 minutes. The solution was filtered and the filtrate concentrated under reduced pressure. The residue was purified by column chromatography over silica eluting with isohexane : dichloromethane (2:3) to give the sub-title compound as an oil (11.79 g).

$^1$H NMR (CDCl$_3$) 7.55–7.47(4H, m); 7.43–7.38(2H, m); 7.32–7.25(1H, m); 6.97–6.92(2H, m); 4.78(1H, q); 4.24(2H, q); 1.64(3H, d); 1.26(3H, t).

b) (2R)-2-(Biphenyl-4-yloxy)propan-1-ol

Lithium aluminium hydride (86.67 ml, 1.0 M solution in tetrahydrofuran) was added dropwise to a stirred solution of (2R)-2-(biphenyl-4-yloxy)propanoic acid, ethyl ester (11.79 g, Example 1a) in dry tetrahydrofuran (200 ml) at 0° C. The resulting solution was stirred at room temperature under nitrogen for 3 hours. Water (3.3 ml), then aqueous sodium hydroxide (50% solution, 3.3 ml) then water (9.9 ml) were cautiously added to the solution at 0° C. Diethyl ether (200 ml) and anhydrous magnesium sulfate (20 g) were added and the solution stirred at room temperature for 20 minutes. The solution was filtered and the filtrate concentrated under reduced pressure to give the sub-title compound as a solid (9.43 g).

m.p. 76–77.6° C.

MS (EI) 228 (M)$^+$ $^1$H NMR (CDCl$_3$) 7.56–7.49(4H, m); 7.39(2H, t); 7.33–7.28(1H, m); 7.03–6.98(2H, m); 4.57–4.52(1H, m); 3.83–3.69(2H, m); 2.02(1H, dd); 1.31(3H, d).

The sub-title compound could also be prepared as follows:

A suspension of 4-biphenol (3.4 g), (S)-(+)-2-bromopropionic acid (3.06 g) and potassium carbonate (5.52 g) in acetone (50 ml) was heated at reflux for 3 hours before being cooled and concentrated under reduced pressure. The residue was partitioned between water (100 ml), saturated aqueous sodium hydrogen carbonate solution (50 ml) and ether (100 ml). The organic phase was separated and the aqueous phase acidified with 2M hydrochloric acid and extracted with ethyl acetate (3×50 ml). The combined organic extracts were dried over anhydrous magnesium sulfate, filtered and concentrated under reduced pressure. The residual white solid was immediately dissolved in tetrahydrofuran (50 ml) and cooled to 0° C. A solution of lithium aluminium hydride (1M in diethyl ether, 20 ml) was then added dropwise. The reaction was allowed to warm to room temperature and was stirred for 1 hour before being re-cooled to 0° C. Water (0.75 ml), followed by sodium hydroxide solution (50% w/v, 0.75 ml) and a second aliquot of water (2 ml) were cautiously added. The resulting mixture was stirred at room temperature for 30 minutes and then dried over anhydrous magnesium sulfate (10 g), filtered and concentrated to give the sub-title compound (1.44 g) as a solid.

m.p. 66–69° C.

MS (APCI) 229 (M+H)$^+$ $^1$H NMR (CDCl$_3$) 7.56–7.50(4H, m); 7.42(2H, t); 7.31 (1H, t); 7.01(2H, d); 4.58–4.51(1H, m); 3.77–3.71(2H, m); 2.03(1H, br); 1.31(3H, d).

c) (2R, 3SR)-4-(Biphenyl-4-yloxy)-1-pyridin-3-yl-pent-4-yn-3-ol

Oxalyl chloride (1.4 ml) was added dropwise to a solution of dimethyl sulfoxide (1.70 ml) in dry dichloromethane (60 ml) at −60° C. was dropwise. The resulting solution was stirred for 20 minutes and then a solution of (2R)-2-(biphenyl-4-yloxy)-1-propanol (2.88 g, Example 1b) in dry dichloromethane (20 ml) was added dropwise. The mixture was stirred for a further 30 minutes and then triethylamine (11.2 ml) was added dropwise. The mixture was allowed to reach room temperature with stirring over 1 hour. The mixture was diluted with anhydrous ether (100 ml), filtered and concentrated under reduced pressure. The residue was dissolved in dry tetrahydrofuran (20 ml) and added to a solution of 1-lithio-2-pyridin-3-ylacetylene [generated by the addition of n-butyllithium (2.5 M in hexanes, 4.4 ml) to a solution of 3-pyridylacetylene (1.04 g) (*J. Amer. Chem. Soc.* 1935, 57, 1284) in tetrahydrofuran (40 ml) at −60° C. with stirring for 20 minutes]. The mixture was stirred for 1 hour at −60° C. and was then allowed to warm to room temperature over 2 hours. The mixture was poured into saturated ammonium chloride solution (100 ml) and extracted with ethyl acetate (3×100 ml). The combined organic extracts were dried over anhydrous magnesium sulfate, filtered and concentrated under reduced pressure. The residue was purified by column chromatography over silica eluting with ethyl acetate:hexane (1:4) and then ethyl acetate to give the sub-title compound as a solid and as a 4:1 mixture of diastereomers (2.18 g).

MS (APCI) 330 (M+H)+

¹H NMR (CDCl₃, major diastereomer) 8.72(1H, dd); 8.55(1H, dd); 7.76–7.72(1H, m); 7.55–7.52(4H, m); 7.44 (2H, t); 7.34–7.26(2H, m); 7.07–7.04(2H, m); 4.86–4.83 (1H, m); 4.67–4.64(1H, m); 2.78(1H, d); 1.51(3H, d).

d) (2R, 3RS)-2-(Biphenyl-4-yloxy)-5-pyridin-3-yl-pentan-3-ol (2R, 3RS)-2-(Biphenyl-4-yloxy)-5-pyridin-3-yl-pent-4-yn-3-ol (4.86 g, Example 1c) was dissolved in ethyl acetate (100 ml) and hydrogenated at 5 atmospheres using 10% palladium on charcoal (0.5 g) as catalyst. The mixture was filtered through celite® and the filtrate concentrated under reduced pressure to give the title compounds (3.95 g)

The diastereomers were separated by normal phase HPLC eluting with isopropanol: dichloromethane (1:20) to give the title compounds.

The product (3R,4R) was recrystallised from ethyl acetate:isohexane (1:4) to give (3R,4R)-4-(Biphenyl-4-yloxy)-1-pyridin-3-yl-pentan-3-ol as a solid (0.25 g).

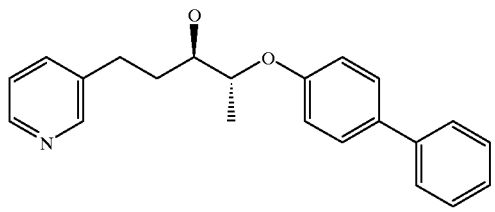

m.p. 98–99.5° C

MS (APCI) 334 (M+H)+

¹H NMR (CDCl₃) 8.52(1H, d); 8.46(1H, dd); 7.57–7.50 (5H, m); 7.41(2H, t); 7.33–7.31(1H, m); 7.24–7.21(1H, m); 6.97(2H, d); 4.28(1H, quintet); 3.68–3.64(2.96–2.89(1H, m); 2.83–2.76(1H, m); 2.51(1H, d); 1.90–1.83(2H, m); 1.29(3H, d).

(3S,4R)-4-(Biphenyl-4-yloxy)-1-pyridin-3-yl-pentan-3-ol (major diastereomer) was recrystallised from ethyl acetate:isohexane (1:1) to give the title compound as a solid (2.23 g).

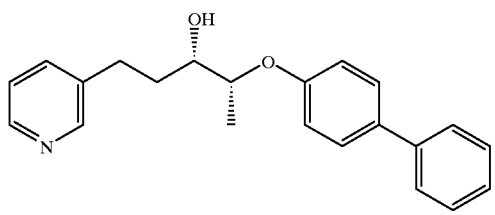

m.p. 121.5–123° C.

MS (APCI) 334 (M+H)+

¹H NMR (CDCl₃) 8.51(1H, d); 8.46(1H, dd); 7.57–7.49 (5H, m); 7.42(2H, t); 7.39–7.33(1H, m); 7.26–7.22(1H, m); 6.94(2H, d); 4.40–4.37(1H, m); 3.89–3.85(1H, m); 3.0–2.95 (1H, m); 2.76–2.71(1H, m); 2.28(1H, d); 1.89–1.81(2H, m); 1.31(3H, d).

EXAMPLE 2

(3R,4S)-4-(Biphenyl-4-yloxy)-1-pyridin-3-yl-pentan-3-ol and (3S,4S)-4-(Biphenyl-4-yloxy)-1-pyridin-3-yl-pentan-3-ol

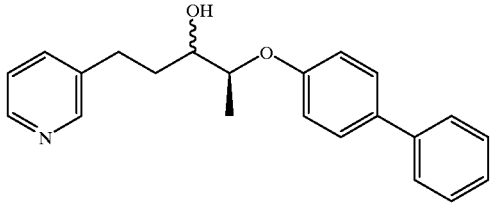

(2S)-2-(Biphenyl-4-yloxy)propanoic acid, ethyl ester

Prepared according to the method described in Example 1a) from diethylazodicarboxylate (6.74 ml), triphenylphosphine (13.11 g), (R)-(+)-ethyl lactate (5.67 ml) and 4-phenylphenol (8.51 g) in dry tetrahydrofuran (125 ml). The residue obtained after work-up was purified by column chromatography over silica eluting with isohexane:dichloromethane (2:3) to give the sub-title compound as an oil (11.3 g).

MS (EI) 270 (M)+

¹H NMR (CDCl₃) 7.55–7.47(4H, m); 7.43–7.38(2H, m); 7.32–7.25(1H, m); 6.97–6.92(2H, m); 4.78(1H, q); 4.24(2H, q); 1.64(3H, d); 1.26(3H, t).

b) (2S)-2-(Biphenyl-4-yloxy)propan-1-ol

Prepared according to the method described in Example 1b) from lithium aluminium hydride (41.9 ml, 1.0M solution in ether) and solution (2S)-2-(biphenyl-4-yloxy)propanoic acid, ethyl ester (11.3 g, Example 2a)) in dry tetrahydrofuran (200 ml) at 0° C. The sub-title compound obtained after work-up was used directly without further purification (9.52 g).

m.p. 75–78° C.

MS (EI) 228 (M)+

¹H NMR (CDCl₃) 7.56–7.49(4H, m); 7.39(2H, t);7.33–7.28(1H, m);7.03–6.98(2H, m); 4.574.52(1H, m); 3.83–3.69(2H, m); 2.04–1.99(1H, dd); 1.31(3H, d).

c) (3RS,4S)-4-(Biphenyl-4-yloxy)-1-pyridin-3-yl-pent-4-yn-3-ol

Prepared according to the method described in Example 1c) from (2S)-2-(biphenyl-4-yloxy)-1-propanol (2.88 g, Example 2b), oxalyl chloride (1.4 ml), dimethyl sulfoxide (1.70 ml), triethylamine (11.18 ml), 3-pyridylacetylene (1.04 g) and n-butyllithium (2.5M in hexanes, 4.4 ml) to give the sub-title compound as a cream solid and as a 4:1 mixture of diastereomers (2.13 g).

MS (APCI) 330 (M+H)+

¹H NMR (CDCl₃, major diastereomer) 8.72(1H, dd); 8.55(1H, dd); 7.76–7.72(1H, m); 7.55–7.52(4H, m); 7.44 (2H, t); 7.34–7.26(2H, m); 7.07–7.04(2H, m); 4.86–4.83 (1H, m); 4.67–4.64(1H, m); 2.78(1H, d); 1.51(3H, d).

d) (3RS,4S)-4-(Biphenyl-4-yloxy)-1-pyridin-3-yl-pentan-3-ol

Prepared according to the method described in Example 1d) from (2S, 3RS)-2-(biphenyl-4-yloxy)-5-pyridin-3-yl-pent-4-yn-3-ol (4.16 g, Example 4c)), 10% palladium on charcoal (0.5 g) in ethyl acetate (100 ml) to give the sub-title compound as a white solid and as a 4:1 mixture of diastereomers (4.13 g).

The diastereomers were separated by normal phase HPLC eluting with isopropanol:dichloromethane (1:20) to give the title compounds.

(3S,4S)-4-(Biphenyl-4-yloxy)-1-pyridin-3-yl-pentan-3-ol (minordiastereomer) was recrystallised from ethyl acetate:isohexane (1:4) to give the title compound as a solid (0.352 g).

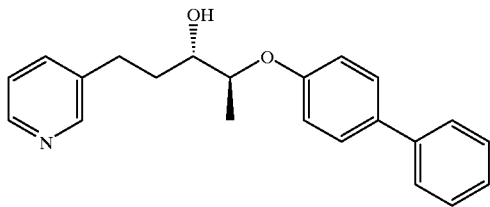

m.p. 102.5–103.5° C.
MS (APCI) 334 (M+H)+
$^1$H NMR (CDCl$_3$) 8.52(1H, d); 8.46(1H, dd); 7.57–7.50 (5H, m); 7.41(2H, t); 7.33–7.31(1H, m); 7.24–7.21(1H, m); 6.97(2H, d); 4.28(1H, quintet); 3.68–3.64(1H, m); 2.96–2.89 (1H, m); 2.83–2.76(1H, m); 2.52(1H, d); 1.90–1.83(2H, m); 1.29(3H, d).

(3R,4S)-4-(Biphenyl-4-yloxy)-1-pyridin-3-yl-pentan-3-ol (majordiastereomer) was recrystallised from ethyl acetate:isohexane (1:1) to give the title compound as a solid (1.76 g).

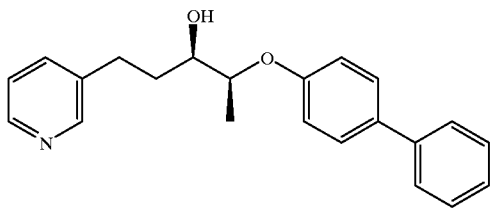

m.p. 123.5–124° C.
MS (APCI) 334 (M+H)+
$^1$H NMR (CDCl$_3$) 8.51(1H, d); 8.46(1H, dd); 7.57–7.49 (5H, m); 7.42(2H, t); 7.39–7.33(1H, m); 7.26–7.22(1H, m); 6.94(2H, d); 4.40–4.37(1H, m); 3.89–3.85(1H, m); 3.0–2.95 (1H, m); 2.76–2.71(1H, m); 2.24(1H, d); 1.89–1.81(2H, m); 3H, d).

EXAMPLE 3

(3R,4S)-4-(Biphenyl-4-yloxy)-1-pyridin-3-yl-pentan-3-ol via diastereomeric esters

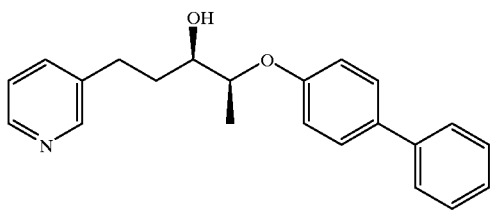

a) (2S)-Methoxyphenylacetic acid, 2-(biphenyl-4-yloxy)-1-(2-pyridin-3-ylethylpropyl ester.

Solid (S)-(+)-(c-methoxyphenylacetic acid (0.25 g), 4-dimethylaminopyridine (0.18 g), and 1-(3-dimethylaminopropyl)-3-ethylcarbodiimide hydrochloride (0.29 g) were added to a solution of (3RS,4S)-4-(biphenyl-4-yloxy)-1-pyridin-3-yl-pentan-3-ol (0.44 g, Example 2c) in dry dichloromethane (30 ml). The reaction was stirred at room temperature for 20 hours and was then concentrated under reduced pressure. The residue was purified by chromatography over silica eluting with ethyl acetate:hexane (2:1) to give the sub-title compound as an oil (0.44 g).

MS (APCI) 482 (M+H)+
$^1$H NMR (CDCl$_3$) 8.40(1H, d); 8.11(1H, d); 7.56–7.48 (6H, m); 7.48–7.37(6H, m); 7.15–7.12(2H, m); 6.92(2H, d); 5.18–5.02(1H, m); 4.76(1H, s); 4.52(1H, dq); 3.41(3H, s);2.22–2.11(2H, m); 1.97–1.9(2H, m); 1.30(3H, d).

b) (3R,4S)-4-(Biphenyl-4-yloxy)-1-pyridin-3-yl-pentan-3-ol

Water (1 ml) and lithium hydroxide (0.063 g) were added to a solution of (S)-(-α-methoxyphenylacetic acid (2S,3R)-4-(biphenyl-4-yloxy)-1-pyridin-3-yl-pent-3-yl ester (0.44 g) in methanol (5 ml) and the resulting solution stirred at room temperature for 4 hours. The mixture was concentrated under reduced pressure and the residue partitioned between ethyl acetate (10 ml) and water (10 ml). The organic layer was separated and the aqueous layer was extracted with ethyl acetate (2×10 ml). The combined organic extracts were dried over anhydrous magnesium sulfate, filtered and concentrated under reduced pressure. The residue was recrystallised from ethyl acetate:hexane (1:3) to give the title compound as a solid (0.21 g).
m.p. 122–123° C.
MS (APCI) 334 (M+H)+
$^1$H NMR (CDCl$_3$) 8.52(1H, d); 8.46(1H, d); 7.57–7.50 (5H, m); 7.43(2H, t); 7.33(1H, t); 7.23(1H, dd); 6.97(2H, d); 4.39(1H, qd); 3.88–3.86(1H, m); 2.96–2.92(1H, m); 2.78–2.72(1H, m); 2.05(1H, br); 1.89–1.83(2H, m); 1.31 (3H, d).

EXAMPLE 4

(1S,2R)-4'-(2-Hydroxy-1-methyl-4-pyridin-3-ylbutoxy)biphenyl-3-carbonitrile and (1S,2S)-4'-(2-Hydroxy-1-methyl-4-pyridin-3-ylbutoxy)biphenyl-3-carbonitrile

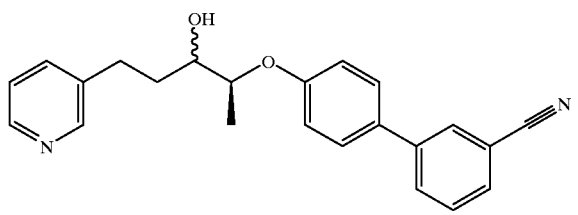

a) (2S)-2-(4-Bromophenoxy)propionic acid, ethyl ester
Prepared according to the method described in Example 1a) from diethylazodicarboxylate (6.7 ml), triphenylphosphine (13.11 g), (R)-(+)-ethyl lactate (5.67 ml) and 4-bromophenol (8.65 g) in dry tetrahydrofuran (125 ml). The residue obtained after work-up was purified by column chromatography over silica eluting with isohexane:dichloromethane (2:3) to give the sub-title compound as an oil (12.2 g).
$^1$H NMR (CDCl$_3$) 7.36(2H, d); 6.75(2H, d); 4.69(1H, q); 4.20(2H, q); 1.61(3H, d); 1.25(3H, t).

b) (2S)-2-(4-Bromophenoxy)propan-1-ol
Sodium borohydride (1.15 g) was added to a solution of (2S)-2-(4-bromophenoxy)propionic acid, ethyl ester (7.5 g, Example 4a)) in ethanol (20 ml) at 5° C. The resulting solution was allowed to attain room temperature and was stirred for 10 hours before being concentrated under reduced pressure. The residue was partitioned between ethyl acetate (100 ml) and 2M hydrochloric acid (50 ml). The mixture was extracted into ethyl acetate and the combined extracts were dried over anhydrous magnesium sulfate, filtered and concentrated under reduced pressure. The product was used directly in the next step without further purification (6.32 g).

MS (EI) 230, 232 (M)+

¹H NMR (CDCl₃) 7.39(2H, d); 6.83(2H, d); 4.50–4.41 (1H, m); 3.77–3.70(2H, m); 1.93(1H, br); 1.26(3H, d).

c) (3RS,4R)-4-(4-Bromophenoxy)-1-pyridin-3-yl-pent-1-yn-3-ol

Prepared according to the method described in Example 1c) from (2S)-2-(4-bromophenoxy)propan-1-ol (9.24 g, Example 4b)), oxalyl chloride (4.38 ml), dimethyl sulfoxide (4.4 ml), triethylamine (22.4 ml), 3-pyridylacetylene (6.3 g) andn-butyllithium (2.5M in hexanes, 24 ml) to give the sub-title compound as an oil and as a 4:1 mixture of diastereomers (8.31 g).

MS (APCI) 332, 334 (M+H)+

¹H NMR (CDCl₃, major diastereomer) 8.73(1H, d); 8.53 (1H, dd); 7.74–7.70(1H, m); 7.39(2H, d);7.29–7.24(1H, m); 8.67(2H, d); 4.82–4.78(1H, m); 4.57–4.53(1H, br); 1.45(3H, d).

d) (3RS ,4R)-4-(4-Bromophenoxy)-1-pyridin-3-yl-pentan-3-ol

Prepared according to the method described in Example 1d) from (3RS,4R)-4-(4-bromophenoxy)-1-pyridin-3-yl-pent-4-yn-3-ol (7.0 g, Example 4c)) and 5% rhodium on charcoal (1.0 g) in ethyl acetate (100 ml) to give the sub-title compound as an oil and as a 4:1 mixture of diastereomers (5.6 g).

MS (APCI) 336, 338 (M+H)+

¹H NMR (CDCl₃, major diastereomer) 8.50(1H, d); 8.45 (1H, dd); 7.54(1H, dt); 7.37(2H, d); 7.22(1H, dd); 6.76(2H, d); 4.30–4.27(1H, m); 3.82(1H, p); 2.94–2.89(1H, m); 2.77–2.70(1H, m); 2.18(1H, br); 1.86–1.78(2H, m); 1.26 (3H, d).

e) (1R,2R)-4'-(2-Hydroxy-1-methyl-4-pyridin-3-ylbutoxy) biphenyl-3-carbonitrile and (1R,2S)-4'-(2-Hydroxy-1-methyl-4-pyridin-3-ylbutoxy)biphenyl-3-carbonitrile A solution of (3RS,4R)-4-(4-bromophenoxy)-1-pyridin-3-yl-pentan-3-ol (1.0 g, Example 4d)), 3-cyanobenzeneboronic acid (0.74 g), 2M aqueous sodium carbonate solution (5 ml) and tetrakis(triphenylphosphine) palladium (0) (0.1 g) in toluene (25 ml) and ethanol (5 ml) was refluxed for 3 hours. The reaction mixture was cooled and poured into water (100 ml) and extracted into ethyl acetate (3×50 ml). The mixture was extracted into ethyl acetate (3×50 ml) and the combined extracts were dried over anhydrous magnesium sulfate, filtered and concentrated under reduced pressure to give the sub-title compound as an oil and as a 4:1 mixture of diastereomers (0.86 g).

The diastereomers were separated by normal-phase HPLC eluting with isopropanol:dichloromethane (1:33) to give the title compounds:

(1S,2S)-4'-(2-Hydroxy-1-methyl-4-pyridin-3-ylbutoxy) biphenyl-3-carbonitrile (minor diastereomer) as an oil (0.22 g).

MS (APCI) 359 (M+H)+

¹H NMR (CDCl₃) 8.51 (1H, d); 8.47(1H, d); 7.82(1H, s); 7.76(1H, dt); 7.60–7.48(5H, m); 7.25–7.21(1H, m); 7.10 (2H, d); 4.30(1H, p); 3.72–3.64(1H, m); 2.99–2.90(1H, m); 2.74(1H, m); 2.44(1H, d); 1.91–1.84(2H, m); 1.30(3H, d).

(1S,2R)-4'-(2-Hydroxy-1-methyl-4-pyridin-3-ylbutoxy) biphenyl-3-carbonitrile(major diastereomer) as an oil (0.52 g).

MS (APCI) 359 (M+H)+

¹H NMR (CDCl₃) 8.51 (1H, d); 8.47(1H, d); 7.82(1H, s); 7.76(1H, dt); 7.60–7.48 (5H, m); 7.25–7.21(1H, m); 7.10 (2H, d); 4.42–4.39(1H, m); 3.88–3.82(1H, m); 3.01–2.90 (1H, m); 2.84–2.74(1H, m); 2.20(1H, d); 1.88–1.84(2H, m); 1.32(3H, d).

EXAMPLE 5

(1S,2R)-4'-(2-Hydroxy-1-methyl-4-pyridin-3-yl-butoxy)-biphenyl-3-sulfonic acid amide and (1S,2S)-4'-(2-Hydroxy-1-methyl-4-pyridin-3-yl-butoxy)-biphenyl-3-sulfonic acid amide a) (3RS,4S)-3-[4-(4-Bromophenoxy)-3-(tertbutyldimethylsilanyloxy)pentyl]pyridine To a solution of (3RS,4S)-4-(4-Bromophenoxy)-1-pyridin-3-yl-pentan-3-ol (2.0 g, Example 4d)) in dry dichloromethane (50 ml) was added tert-butyldimethylsilyl chloride (1.17 g) and imidazole (1.08 g) and the resulting solution stirred for 24 hours, concentrated and the residue purified by chromatography on silica gel eluting with ethyl acetate:hexane (1:4 to 1:1) to afford the sub-title compound as an oil (2.52 g).

MS (APCI) 450.1, 452.1 (M+H)+

¹H NMR (CDCl₃, major diastereomer) 8.45–8.42(2H, m); 7.4(1H, dt); 7.35(2H, d); 7.22–7.18 (1H, m); 6.73 (2H, d); 4.23–4.20(1H, m); 3.82–3.78(1H, m); 2.84–2.62(2H, m); 1.96–1.88 (1H, m); 1.82–1.78 (1H, m); 1.27(3H, d); 0.94 (9H, s); 0.12 (3H, s); 0.09 (3H, s).

b) (1S,2RS)-4-[2-(tert-butyldimethylsilanyloxy)-1-methyl-4-pyridin-3-ylbutoxy]benzeneboronic acid A solution of tert-butyllithium (2.5 ml, 1.7M in hexanes) was added over a 1 hour period to a solution of (2S,3RS)-2-(4-bromophenoxy)-3-tert-butyldimethylsilyloxy-5-pyridin-3-ylpentane (1.60 g, Example 5b)) and triisopropylborate (1.07 ml) in tetrahydrofuran (25 ml) at −78° C. The resulting solution was stirred at −78° C. for 2 hours and was then quenched by the addition of a saturated solution of ammonium chloride in water (50 ml). The mixture was poured into water (50 ml) and extracted into ethyl acetate (2×50 ml). The combined extracts were dried over anhydrous magnesium sulfate, filtered and concentrated. The residue was purified by chromatography on silica eluting with ethyl acetate and then ethyl acetate:methanol (4:1) to afford the sub-title compound as a foam (1.2 g).

¹H NMR (CDCl₃, major diastereomer) 8.60–8.53 (2H, m); 7.95 (2H, d); 7.6–7.54 (1H, m) 7.26–7.22 (1H, m); 6.86

(2H, d); 4.33–4.27 (1H, m); 3.93–3.86 (1H, m); 2.82–2.62 (2H, m); 1.98–1.75 (2H, m); 1.28 (3H, d); 0.94 (9H, s); 0.08 (6H, s).

c) (1S, 2R)-4'(2-Hydroxy-1-methyl-4-pyridin-3-ylbutoxy) biphenyl-3-sulfonic acid amide and (1S, 2S)-4'(2-Hydroxy-1-methyl-4-pyridin-3-ylbutoxy)biphenyl-3-sulfonic acid amide Prepared according to the method described in Example 4e) from (1S,2RS)-4-[2-(tert-butyldimethylsilanyloxy)-1-methyl-4-pyridin-3-ylbutoxy]benzeneboronic acid.(1.9 g, Example 5b)), 3-bromobenzenesulfonamide (1.62 g), 2M sodium carbonate solution (5 ml) and tetrakis (triphenylphosphine)palladium (0) (0.1 g) in toluene (25 ml) and ethanol (5 ml). The reaction was refluxed for 3 hours. The solvent was concentrated in vacuo and the residue redissolved in methanol (5 ml) and concentrated hydrochloric acid (1 ml) added. After 16 hours the mixture was again evaporated and worked-up as described in Example 4e) to afford the sub-title compounds as a mixture of diastereomers (1.62 g); The diastereomers were separated by normal phase HPLC eluting with isopropanol:dichloromethane (1:33) to give the title compounds.

(1S, 2R)-4'-(2-Hydroxy-1-methyl-4-pyridin-3-ylbutoxy) biphenyl-3-sulfonic acid amide (major diastereomer) as an oil (0.70 g).

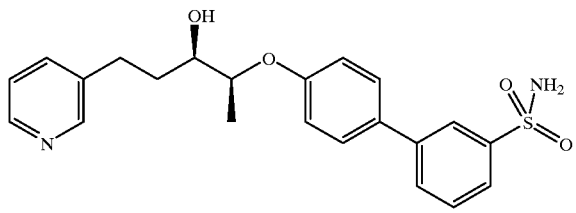

MS (APCI) 413.1 (M+H)$^+$
$^1$H NMR (CDCl$_3$) 8.49(1H, d); 8.45(1H, d); 8.10(1H, t); 7.87(1H, dt); 7.75(1H, dt); 7.58–7.49(4H, m); 7.49–7.21 (1H, m); 6.95(2H, d); 5.03(2H, s); 4.41–4.37(1H m); 3.01–2.92(1H, m); 2.80–2.71(1H, m); 2.32(1H, br); 1.90–1.82(2H, m); 1.31(3H, d).

(1S, 2S)-4'-(2-Hydroxy-1-methyl-4-pyridin-3-ylbutoxy) biphenyl-3-sulfonic acid amide (minor diastereomer) as an oil (0.31 g).

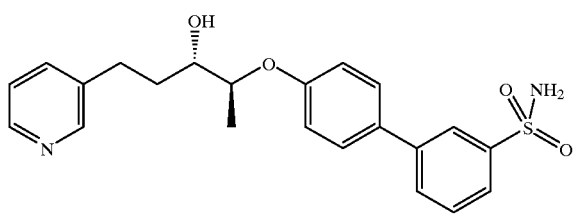

MS (APCI) 413.1 (M+H)$^+$
$^1$H NMR (CDCl$_3$) 8.50 (1H, d); 8.46 (1H, d); 8.10 (1H, t); 7.87 (1H, dt); 7.75 (1H, dt); 7.58–7.49 (4H, m); 7.49–7.21 (1H, m); 6.99 (2H, d); 4.87 (2H, s); 4.30 (1H, p); 3.73–3.63 (1H, m); 3.01–2.92 (1H, m); 2.80–2.71 (1H, m); 2.46 (1H, br); 1.90–1.82 (2H, m); 1.30 (3H, d).

EXAMPLE 6

(3R,4S)-4-(3'-Chlorobiphenyl-4-yloxy)-1-pyridin-3-yl-pentan-3-ol oxalic acid salt and (3S,4S)-4-(3'-Chlorobiphenyl-4-yloxy)-1-pyridin-3-yl-pentan-3-ol oxalic acid salt

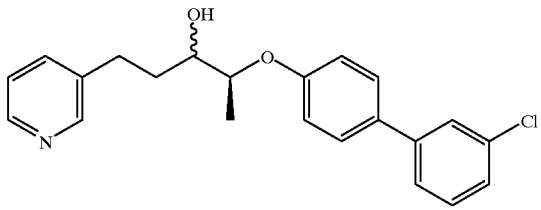

Prepared according to the method as described in Example 4e) from (3RS,4R)-4-(4-Bromophenoxy)-1-pyridin-3-yl-pentan-3-ol (1.05 g, Example 4d), 3-chlorobenzene boronic acid (1.1 g), 2M aqueous sodium carbonate solution (3.6 ml) and tetrakis(triphenylphosphine) palladium (0) (0.36 g), toluene (25 ml) and ethanol (5 ml) to give the sub-title compound as an oil and as a 4:1 mixture of diastereomers (1.09 g). The diastereomers were separated by normal-phase HPLC eluting with isopropanol:dichloromethane (1:33) to give two oils which were converted to the oxalate salts upon treatment with oxalic acid (excess) in ether to give the title compounds:

(3S,4S)-4-(3'-Chlorobiphenyl-4-yloxy)-1-pyridin-3-yl-pentan-3-ol oxalic acid salt(minor diastereomer) as a solid (0.11 g).

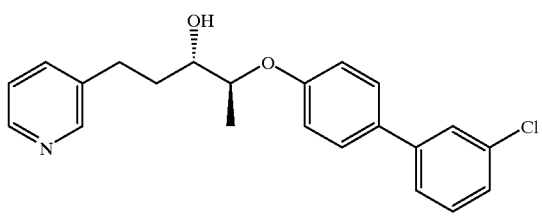

m.p. 71–73° C.
MS (APCI) 368 [(M-oxalic acid)+H]$^+$
$^1$H NMR (DMSO-D6) 8.46(1H, d); 8.40(1H, dd); 7.68–7.57(5H, m); 7.45(1H, t); 7.37–7.30(2H, m); 7.0(2H, d); 4.45–4.37(1H, m); 4.0(1H, br.s); 3.58–3.53(1H, m); 2.87–2.78(1H, m); 2.68–2.58(1H, m); 1.81–1.69(2H, m); 1.21(3H, d).

(3R,4S)-4-(3'-Chlorobiphenyl-4-yloxy)-1-pyridin-3-yl-pentan-3-ol oxalic acid salt (major diastereomer) as a solid (0.50 g).

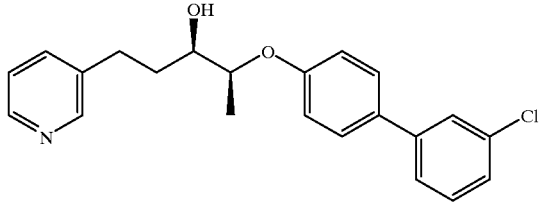

m.p. 146.5–147.5° C.
MS (APCI) 368 [(M-oxalic acid)+H]$^+$
$^1$H NMR (DMSO-D6) 8.47(1H, d): 8.42(1H, dd); 7.70–7.56(5H, m); 7.44(1H, m); 7.36–7.32(2H, m); 7.0(2H, d); 4.36–4.32(1H, m); 3.58–3.53(1H, m); 2.86–2.78(1H, m); 2.71–2.64(1H, m); 1.89–1.85(1H, m); 1.68–1.63(1H, m); 1.24(3H, d).

EXAMPLE 7

(3R,4S)-4-(4'-Fluoro-biphenyl-4-yloxy)-1-pyridin-3-yl-pentan-3-ol and (3S,4R)-4-(4'-Fluoro-biphenyl-4-yloxy)-1-pyridin-3-yl-pentan-3-ol

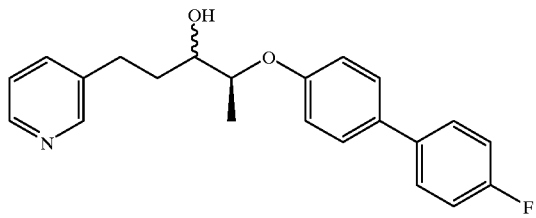

Prepared according to the method as described in Example 4e) from (3RS,4R)-4-(4-Bromophenoxy)-1-pyridin-3-yl-pentan-3-ol (1.0 g, Example 4d), 4-fluorobenzeneboronic acid (0.62 g), 2M aqueous sodium carbonate solution (2.2 ml) and tetrakis(triphenylphosphine) palladium (0) (0.34 g), toluene (30 ml) and ethanol (10 ml) to give the title compound as solid and as a 4:1 mixture of diastereomers (0.6 g). The diastereomers were separated by normal phase HPLC eluting with isopropanol:dichloromethane (1:33) to give two solids which were recrystallised from hexane:ethyl acetate (1:1) to give the title compounds:

(3R,4S)-4-(4'-Fluoro-biphenyl-4-yloxy)-1-pyridin-3-yl-pentan-3-ol (majordiastereomer) as a solid (0.26 g).

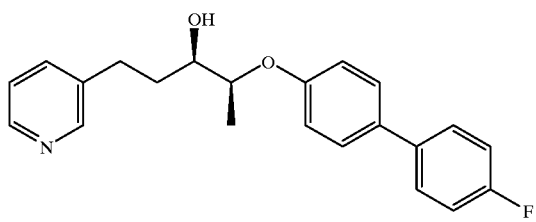

m.p. 121–122° C.
MS (APCI) 352 (M+H)$^+$
$^1$H NMR (CDCl$_3$) 8.50(1H, d): 8.45(1H, dd); 7.60–7.55 (1H, m); 7.50–7.40(4H, m); 7.25–7.20(1H, m); 7.05–7.15 (2H, m); 7.0–6.95(2H, m); 4.45–4.35(1H, m); 3.0–2.90(1H, m); 2.80–2.65(1H, m); 2.50(1H, d); 1.90–1.80(2H, m); 1.30(3H, d);

(3S,4S)-4-(4'-Fluoro-biphenyl-4-yloxy)-1-pyridin-3-yl-pentan-3-ol (minor diasteromer) as a solid (0.106 g).

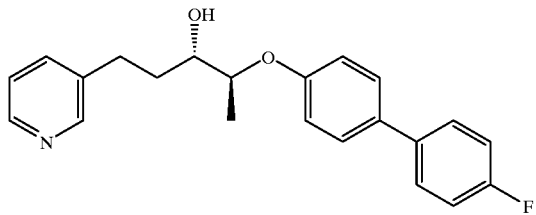

m.p. 147–148° C.
MS (APCI) 352 (M+H)$^+$
$^1$H NMR (CDCl$_3$) 8.50(1H, d):8.45(1H, dd); 7.60–7.55 (1H, m); 7.50–7.40(4H, m) 7.25–7.20(1H, m); 7.05–7.15 (2H, m); 7.0–6.95(2H, m); 4.30–4.20(1H, m); 3.70–3.60 (1H, m); 3.0–2.90(1H, m); 2.85–2.70(1H, m); 2.45(1H, d);1.90–1.80(2H, m); 1.30(3H, d).

EXAMPLE 8

(3R,4S)-4-(Biphenyl-4-yloxy)-5-methyl-1-pyridin-3-yl-hexan-3-ol

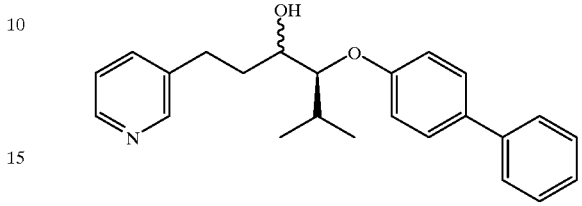

a) (2S)-2-(Biphenyl-4-yloxy)-3-methylbutyric acid, methyl ester

Diethylazodicarboxylate (11.5 ml) in dry tetrahydrofuran (40 ml) was added dropwise over 30 minutes to a stirred solution of triphenylphosphine (22 g), methyl (R)-2-hydroxy-3-methylbutanoate (11.2 g, J.Am.Chem.Soc., (1990), 112, 21, 7659) and 4-phenylphenol (14.5 g) in dry tetrahydrofuran (120 ml). The resulting solution was stirred at room temperature overnight and was then concentrated under reduced pressure. A mixture of isohexane:ether (9:1) (750 ml) was added to the residue and the mixture stirred at room temperature for 30 minutes. The solution was filtered and the filtrate concentrated under reduced pressure. The residue was purified by column chromatography over silica eluting with isohexane:dichloromethane (1:4) then (1:1) to give the sub-title compound as a solid, which was recrystallised from hexane to give a crystalline solid (7.9 g).
m.p. 82–85° C.
$^1$H NMR (CDCl$_3$) 7.55–7.45(4H, m); 7.41(2H, t); 7.35–7.25(1H, m); 6.94(2H, dt) 4.42(1H, d); 3.77(3H, s); 2.30 (1H, sextet), 1.11(3H, d); 1.08(3H, d).

b) (2S)-2-(Biphenyl-4-yloxy)-3-methylbutan-1-ol

A solution of lithium aluminium hydride (1.0M in tetrahydrofuran, 16 ml,) was added dropwise to a stirred (2S)-2-(biphenyl-4-yloxy)-3-methylbutyric acid, methyl ester (4.0 g, Example 8a)) in dry tetrahydrofuran (80 ml) at room temperature and the reaction was left to stir overnight. Water (0.6 ml), then aqueous sodium hydroxide (50%, 0.6 ml) then water (2.4 ml) were cautiously added to the solution at 0° C. Diethyl ether (200 ml) and anhydrous magnesium sulfate (10 g) were added and the solution stirred at room temperature for 10 minutes. The solution was filtered and the filtrate concentrated under reduced pressure. The residue was purified by column chromatography over silica eluting with dichloromethane then dichloromethane:ether (49:1) to give the sub-title compound as an oil which solidified on standing (3.43 g).
m.p. 45–47° C.
$^1$H NMR (CDCl$_3$) 7.58–7.48(4H, m); 7.41(2H, t); 7.35–7.25(1H, m); 7.04(2H, d); 4.25–4.15(1H, m); 3.90–3.75(2H, m); 2.10(1H, sextet); 1.77(1H, dd); 1.1–0.9 (6H, m).

c) (3RS, 4S)-4-(Biphenyl-4-yloxy)-5-methyl-1-pyridin-3-yl-hex-1-yn-3-ol

Oxalyl chloride (1.65 ml) was added dropwise to a solution of dimethyl sulfoxide (2.25 ml) in dry dichloromethane (120 ml) at –65° C. The resulting solution was stirred for 10 minutes and then a solution of (2S)-2-(biphenyl-4-yloxy)-3-methylbutan-1-ol (3.40 g, Example 8b)) in dry dichloromethane (30 ml) was added dropwise at −65° C. The mixture was stirred for a further 15 minutes and then triethylamine (12 ml) was added dropwise. The mixture was allowed to warm to 10° C. with stirring. The mixture was then diluted with isohexane (250 ml), stirred for 10 minutes, filtered and concentrated under reduced pressure. The residue was dissolved in dry tetrahydrofuran (20 ml) and added at −20° C. to a solution of 1-lithio-2-pyridin-3-ylacetylene [generated by the addition of n-butyllithium (2.5 M in hexanes, 8.4 ml) to a solution of pyridylacetylene (2.0 g) (*J. Amer. Chem. Soc.* 1935, 57, 1284) in tetrahydrofuran (80 ml) at −60° C. with stirring for 20 minutes]. The mixture was allowed to warm to room temperature and after 30 minutes was poured into water (200 ml). The mixture was extracted with ethyl acetate, the combined organic extracts dried over anhydrous magnesium sulfate, filtered and concentrated under reduced pressure. The residue was purified by column chromatography over silica eluting with dichloromethane:ethyl acetate (4:1) to give the sub-title compound as an oil and as a 3:1 mixture of diastereomers (4.38 g).

MS (APCI+) 358 (M+H)+

$^1$H NMR (CDCl$_3$) 8.65 & 8.58(together 1H, 2xd); 7.52–7.48(1H, m); 7.65–7.46(5H, m); 7.42(2H, m); 7.35–7.10(4H, m); 4.93⁴.83(1H, m); 4.38–4.30(1H, m); 2.75–2.65(1H, m); 2.32(1H, septet); 1.15–1.05(6H, m).

d) (3RS, 4S)-4-(Biphenyl-4-yloxy)-5-methyl-1-pyridin-3-yl-3-hexanol (3RS, 4S)-4-(Biphenyl-4-yloxy)-5-methyl-1-pyridin-3-ylhex-1-yn-3-ol (4.38 g, Example 8c)) was dissolved in ethyl acetate (100 ml) and hydrogenated at 3 atmospheres using 10% palladium on charcoal (0.6 g) as catalyst. The mixture was filtered through celite® and the filtrate concentrated under reduced pressure to give a mixture of the sub-title compounds as an oil (4.68 g).

The diastereomers were separated by normal-phase HPLC eluting with isopropanol:dichloromethane (1:20) to give the sub-title compounds as oils which were converted to their oxalic acid salts by treatment with a saturated ethereal solution of oxalic acid.

(3S, 4S)-4-(Biphenyl-4-yloxy)-5-methyl-1-pyridin-3-yl-3-hexanol oxalic acid salt (minor diastereomer).

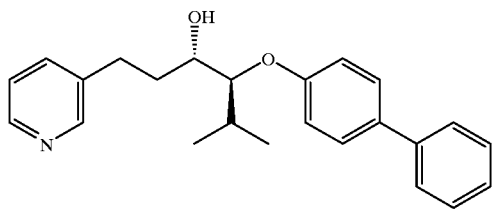

m.p. 75° C. (dec.)

MS (APCI+) 362.2 (M−oxalic acid+H)+

$^1$H NMR (DMSO) 8.42–8.32(2H, m); 7.65–7.50(5H, m); 7.40(2H, t); 7.35–7.25(2H, m); 7.08(2H, m); 4.1–4.05(1H, m); 3.7–3.65(1H, m); 2.85–2.7(1H, m); 2.68–2.55(1H, m); 2.08(1H, sextet); 1.75–1.65(2H, m); 1.0–0.85(6H, m).

(3R, 4S)-4-(Biphenyl-4-yloxy)-5-methyl-1-pyridin-3-yl-3-hexanol oxalic acid salt (major diastereomer).

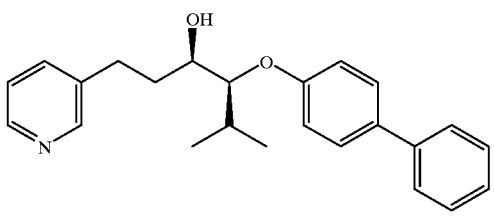

m.p.100–105° C.

MS (APCI+) 362.2 (M−oxalic acid+H)+

$^1$H NMR (DMSO) 8.39(2H, s); 7.65–7.50(5H, m); 7.42 (2H, t); 7.35–7.25(2H, m); 7.05(2H, d); 4.15–4.10(1H, m); 3.7–3.55(1H, m); 2.85–2.55(2H, m); 2.20–2.10(1H, m); 1.9–1.7(1H, m); 1.7–1.55(1H, m); 0.94(3H, d); 0.89(3H, d).

EXAMPLE 9

(±)-1-[1-(Biphenyl-4-yloxy)-cyclopropyl]-3-pyridin-3-yl-propan-1-ol

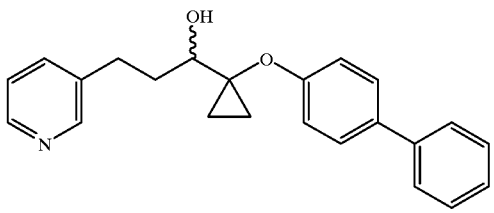

a) 4-(1-Phenylsulfanyl-cyclopropoxy)biphenyl

Butyllithium (2.5M in hexanes, 6.1 ml) was added to a stirred solution of phenyl-cyclopropylsulfide (2 g) in dry tetrahydrofuran (45 ml) at 0° C., under nitrogen. Stirring was continued for 3 hours at 0° C., the solution was then cooled to −78° C. and iodine (4.05 g) in dry tetrahydrofuran (20 ml) added over a 10 minute period. Stirring was continued at this temperature for 15 minutes, then sodium metabisulfite solution (10% aqueous, 20 ml) was added, and the mixture allowed to warm up to room temperature. The iodinated product was extracted into diethyl ether, washed with saturated brine, dried over anhydrous magnesium sulfate and filtered. The filtrate was concentrated under reduced pressure to give a light brown oil.

The above oil was dissolved in acetonitrile (30 ml), and 4-biphenol (2.7 g) and cesium carbonate (5.2 g) added. The mixture was heated at reflux for 24 hours. The cooled mixture was filtered, and the filtrate concentrated under reduced pressure. The residue was purified by column chromatography over silica eluting with dichloromethane:hexane (1:19) to give the sub-title compound as an oil (0.95 g).

MS (EI) 318 (M)+

$^1$H NMR (DMSO) 7.70–7.60(4H, m); 7.53–7.27(8H, m); 7.18 (2H, d); 1.55–1.38(4H, m).

b) (±)-1-[1-(Biphenyl-4-yloxy)-cyclopropyl]-3-pyridin-3-yl-propan-1-ol

Lithium naphthalenide (0.625M, 7.4 ml; prepared by adding equimolar quantities of naphthalene and lithium metal to tetrahydrofuran, under nitrogen, and stirring at room temperature overnight) was added slowly to a stirred solution of 4-(1-phenylsulfanyl-cyclopropoxy)biphenyl (0.7 g) in dry tetrahydrofuran at −78° C., under nitrogen, and then stirred at this temperature for 15 minutes. To this was added a solution of 3-pyridinepropanal (0.3 g, prepared according to the method of Example 3 of International Patent Application No. WO-A-92/19593) in dry tetrahydrofuran (15 ml), and the stirring was continued at −78° C. for 5 minutes, then allowed to warm up to room temperature. The reaction was quenched with saturated aqueous ammonium chloride solution, and extracted into diethyl ether (3×30 ml). The combined extracts were washed with brine, dried over anhydrous magnesium sulfate and filtered. The filtrate was concentrated under reduced pressure to give a pale yellow gum, which was further purified by reverse phase HPLC to give the title compound as a pale yellow gum (0.11 g).

MS (APCI) 346 (M+H)+

1H NMR (DMSO) 8.4(1H, d); 8.35(1H, dd); 7.65–7.50 (5H, m); 7.43(2H, t); 7.35–7.2(2H, m); 7.1(2H, d); 5.1(1H, d); 3.9–3.8(1H, m); 2.9–2.55(2H, m); 2.05–1.9(1H, m); 1.75–1.6(1H, m); 1.15–1.05(1H, m); 0.95–0.88(1H, m); 0.82–0.70(2H, m).

EXAMPLE 10

(2S, 3R)-4-(6-Bromonaphthalen-2-yloxy)-1-pyridin-3-yl-pentan-3-ol and (2R, 3S)-4-(6-Bromonaphthalen-2-yloxy)-1-pyridin-3-yl-pentan-3-ol

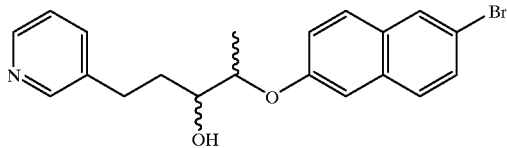

a) (2S)-2-(6-Bromonaphthalen-2-yloxy)-propionic acid ethyl ester

Prepared according to the method described in Example 1a) from 2-hydroxy-6-bromonaphthalene (11.2 g), R-(+)-ethyl lactate (5.93 g), triphenylphosphine (13.15 g) and diethylazodicarboxylate (9.61 g) in dry tetrahydrofuran (120 ml). The crude product was purified by column chromatography over silica eluting with dichloromethane:hexane (1:4–2:3) to give the sub-title compound as a solid (12.45 g). m.p. 72–74° C.

GC/MS 322–324 [M]+

1H NMR (DMSO) 8.13(1H, d); 7.85(1H, d); 7.75(1H, d); 7.57(1H, dd); 7.25(2H, d); 5.12(1H, q); 4.16(2H, q); 1.57 (3H, d); 1.17(3H, t).

b) (2S)-2-(6-Bromonaphthalen-2-yloxy)-propan-1-ol

Prepared according to the method described in Example 4b) from (2S)-2-(6-bromonaphthalen-2-yloxy)-propionic acid ethyl ester (12.45 g, Example 10a)) and sodium borohydride (1.6 g) in ethanol (150 ml). The crude material was purified by column chromatography over silica eluting with ethanol:dichloromethane (1:99) to give the sub-title compound as a solid (10.5 g). m.p. 71–72° C.

gC/MS 280–282 [M]+

1H NMR (CDCl3) 7.92(1H, d); 7.67(1H, dd); 7.59(1H, d); 7.50(1H, dd); 7.18 (2H, dd); 4.70–4.61(1H, m); 3.87–3.74 (2H, m); 2.02(1H, br s); 1.35(3H, d).

c) (2S,3RS)-4-(6-Bromo-naphthalen-2-yloxy)-1-pyridin-3-yl-pent-1-yn-3-ol

Prepared according to the method described in Example 1c) from (2S)-2-(6-bromonaphthalen-2-yloxy)-propan1-ol (5 g, Example 10b)), oxalyl chloride (2.9 g), dimethylsulfoxide (2.64 g), triethylamine (11.43 g), n-butyllithium (2.5M in hexanes, 12 ml) and 3-pyridylacetylene (3.15 g) to give the sub-title compound as a 4:1 mixture of diastereomers (4.4 g).

MS (APCI) 383 (M+H)+

1H NMR (CDCl3 major diastereomer) 8.75(1H, d); 8.54 (1H, dd); 7.93(1H, d); 7.75–7.66(2H, m); 7.60(1H, d); 7.51(1H, dd); 7.49–7.20(3H, m); 4.88(1H, br s); 4.80–4.72 (1H, m); 3.23(1H, br.s); 1.55(3H, d).

d) (2S, 3RS)-4-(6-Bromonaphthalen-2-yloxy)-1-pyridin-3-yl-pentan-3-ol

Prepared according to the method described in Example 1d) from (2S, 3RS)-4-(6-bromonaphthalen-2-yloxy)-1-pyridin-3-yl-pent-1-yn-3-ol (2.78 g, Example 10c)) and 5% rhodium on carbon (1.5 g) in ethyl acetate (150 ml) at 2 atmospheres pressure to give the sub-title compound as an oil and as a 4:1 mixture of diastereomers (2.6 g).

The diastereomers were separated by normal phase HPLC eluting with isopropanol:dichloromethane (1:20) to give (3R, 2S)-4-(6-bromonaphthalen-2-yloxy)-1-pyridin-3-yl-pentan-3-ol as the major second eluting diastereomer.

MS (APCI) 388 (M+H)+

1H NMR (CDCl3) 8.52(1H, d); 8.46(1H, dd); 7.91(1H, d); 7.66(1H, d); 7.56(1H, dt); 7.50(2H, dd); 7.26–7.20(1H, m); 7.16–7.09(2H, m); 4.50–4.47(1H, m); 3.92–3.87(1H, m); 2.96–2.92(1H, m); 2.80–2.73(1H, m); 2.20(1H, br s); 92–1.84(2H, m); 1.35(3H, d). e.e. 44% (estimated by HPLC using a Chiralpak AD column and eluting with isohexane:ethanol (60:40)

e) 5-Oxo-pyrrolidine-1,2-dicarboxylic acid 1-benzyl ester (2R,3S)-2-[2-(6-Bromonaphthalen-2-yloxy)-1-(2-pyridin-3-yl-ethyl)propyl]ester and 5-Oxo-pyrrolidine-1,2-dicarboxylic acid 1-benzyl ester (2S,3R)-2-[2-(6-Bromonaphthalen-2-yloxy)-1-2pyridin-3-yl-ethyl)propyl] ester (2S, 3R)-4-(6-Bromonaphthalen-2-yloxy)-1-pyridin-3-yl-pentan-3-ol, (2R, 3S)-4-(6-bromonaphthalen-2-yloxy)-1-pyridin-3-yl-pentan-3-ol (1.5 g Example 10d)), 5-oxo-pyrrolidine-1,2-dicarboxylic acid 1-benzyl ester (2.05 g), 1-(3-dimethylaminopropyl)-3-ethylcarbodiimide hydrochloride (1.5 g) and 4-dimethylaminopyridine (0.95 g) were stirred in dichloromethane (50 ml) at room temperature overnight. The reaction mixture was concentrated under reduced pressure and the residue purified by column chromatography over silica gel eluting with ethyl acetate:hexane (4:1) to give an oil (2.3 g). The diastereomers were separated by normal-phase HPLC eluting with ethyl acetate:hexane (4:1 ) to give the sub-title compounds.

5-Oxo-pyrrolidine-1,2-dicarboxylic acid 1-benzyl ester (2S, 3R)-2-[2-(6-bromo-naphthalen-2-yloxy)-1-(2-pyridin-3-yl-ethyl)propyl]ester (major, second eluting diastereomer 1.46 g).

MS (APCI) 632 (M+H)+

1H NMR (CDCl3) 8.46(1H, dd); 8.42(1H, d); 7.91(1H, d); 7.64(1H, d); 7.55(2H, d); 7.50(1H, d); 7.45–7.26(5H, m); 7.20(1H, t); 7.08(1H, d); 7.05(1H, s); 5.29(2H, d); 5.18–5.15 (1H, m); 4.75(1H, dd); 4.63–4.53(1H, m) 2.69–2.30(5H, m); 2.05–1.92(3H, m); 1.31(3H, d).

5-Oxo-pyrrolidine-1,2-dicarboxylic acid 1-benzyl ester (2R, 3S)-2-[2-(6-Bromonaphthalen-2-yloxy)-1-(2-pyridin-3-yl-ethylpropyl]ester (minor, first eluting diastereomer 0.37 g)

MS (APCI) 632 (M+H)+

1H NMR (CDCl3) 8.47(1H, dd); 8.45(1H, d); 7.91(1H, s); 7.64(1H, d); 7.52(2H, d); 7.48(1H, d); 7.34–7.26(5H, m); 7.20(1H, t); 7.07–7.01(2H, m); 5.21–5.19(2H, m); 4.75(1H, dd); 4.65–4.55(1H, m); 2.78–2.25(5H, m); 2.18–1.92(3H, m); 1.35(3H, d).

f) (2S, 3R)-4-(6-Bromo-naphthalen-2-yloxy)-1-pyridin-3-yl-pentan-3-ol

5-Oxo-pyrrolidine-1,2-dicarboxylic acid 1-benzyl ester (2S, 3R)-2-[2-(6-bromo-naphthalen-2-yloxy)-1-(2-pyridin-3- yl-ethyl)-propyl]ester (1.46 g Example 10e)) and potassium carbonate (0.96 g) were stirred at room temperature in methanol (24 ml) and water (1 ml) overnight. The reaction mixture was concentrated under reduced pressure and the residue partitioned between ethyl acetate and water. The organic phase was separated, washed with brine, dried over anhydrous magnesium sulfate and filtered. The filtrate was concentrated under reduced pressure and the residue triturated in ether:hexane (1:1) to give the title compound as a solid (0.7 g).

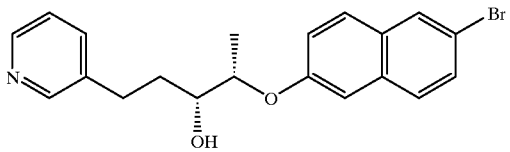

m.p.1 17–118° C.
MS (APCI) 388 (M+H)$^+$
$^1$H NMR (CDCl$_3$) 8.52(1H, d); 8.46(1H, dd); 7.91(1H, d); 7.66(1H, d); 7.56(1H, dt); 7.50(2H, dd); 7.26–7.20(1H, m); 7.16–7.09(2H, m); 4.50–4.47(1H, m); 3.92–3.87(1H, m); 2.96–2.92(1H, m); 2.80–2.73(1H, m); 2.20(1H, br s); 1.92–1.84(2H, m); 1.35(3H, d).

(2R, 3S)-4-(6-Bromonaphthalen-2-yloxy)-1-pyridin-3-yl-pentan-3-ol

Prepared according to the method described in Example 10f) from 5-Oxo-pyrrolidine-1,2-dicarboxylic acid 1-benzyl ester (2R,3S)-2-[2-(6-bromo-naphthalen-2-yloxy)-1-(2-pyridin-3-yl-ethyl)-propyl]ester (0.37 g Example 10e)) and potassium carbonate (0.24 g) in methanol (14 ml) and water (1 ml) to give the title compound as a solid (0.15 g).

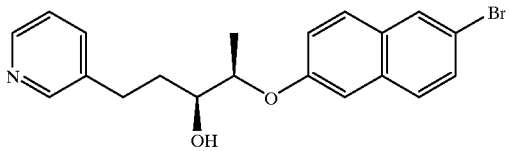

m.p.1 16–117° C.
MS (APCI) 388 (M+H)$^+$
$^1$H NMR (CDCl$_3$) 8.52(1H, d); 8.46(1H, dd); 7.91(1H, d); 7.66(1H, d); 7.56(1H, dt); 7.50(2H, dd); 7.26–7.20(1H, m); 7.16–7.09(2H, m); 4.50–4.47(1H, m); 3.92–3.87(1H, m); 2.96–2.92(1H, m); 2.80–2.73(1H, m); 2.20(1H, br s); 1.92–1.84(2H, m); 1.35(3H, d).

EXAMPLE 11

(1S,2R)-4-[2-(tert-butyldimethylsilanyloxy)-1-methyl-4-pyridin-3-ylbutoxy]benzeneboronic acid

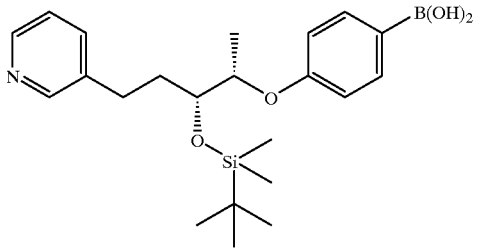

a) (3S,4R)-4-(4-Bromophenoxy)-1-pyridin-3-yl-pentan-3-ol

Prepared according to the method described in Example 1d) from (3RS,4R)-4-(4-bromophenoxy)-1-pyridin-3-yl-pent-1-yn-3-ol (5.93 g, Example 4c)) and 5% rhodium on charcoal (2.0 g) in ethyl acetate (100 ml) to give the sub-title compound as an oil and as a 4:1 mixture of diastereomers (5.6 g). The diastereomers were separated using normal-phase HPLC eluting with 3% isopropyl alcohol in dichloromethane to give (2S, 3R)-2-(4-bromophenoxy)-5-pyridin-3-yl-pentan-3-ol as the majordiastereomer (3.21 g) and (2S, 3S)-2-(4-bromophenoxy)-5-pyridin-3-yl-pentan-3-ol as the second eluting and minor diastereomer (0.71 g).
MS (APCI) 336/338 (M+H)$^+$
$^1$H NMR (CDCl$_3$, major diastereomer) 8.50(1H, d); 8.45 (1H, dd); 7.54(1H, dt); 7.37(2H, d); 7.22(1H, dd); 6.76(2H, d); 4.30–4.27(1H, m); 3.82(1H, p); 2.94–2.89(1H, m); 2.77–2.70(1H, m); 2.18(1H, br); 1.86–1.78(2H, m); 1.26 (3H, d).

b) (3R,4S)-3-[4-(4-Bromophenoxy)-3-(tert-butyldimethylsilanyloxy)pentyl]pyridine Prepared according to the method described in Example 5a) from (3S,4R)-4-(4-Bromophenoxy)-1-pyridin-3-yl-pentan-3-ol (2.01 g, Example 5a)), tert-butyldimethylsilyl chloride (1.81 g) and imidazole (0.814 g) in dry dichloromethane to afford the sub-title compound as an oil (2.52 g) after column chromatography eluting with dichloromethane:diethyl ether (1:1).
MS (APCI) 450/452 (M+H)$^+$
$^1$H NMR (CDCl$_3$) 8.45–8.42(2H, m); 7.4(1H, dt); 7.35 (2H, d); 7.22–7.18 (1H, m); 6.73 (2H, d); 4.23–4.20(1H, m); 3.82–3.78(1H, m); 2.84–2.62(2H, m); 1.96–1.88 (1H, m); 1.82–1.78(1H, m); 1.27(3H, d); 0.94 (9H, s); 0.12 (3H, s); 0.09 (3H, s).

c) (1S,2R)-4-[2-(tert-butyldimethylsilanyloxy)-1-methyl-4-pyridin-3-ylbutoxy]benzeneboronic acid Prepared according to the method described in Example 5b) from tert-butyllithium (3.95 ml, 1.7M in hexanes), (3R,4S)-3-[4-(4-bromophenoxy)-3-(tert-butyldimethyl-silanyloxy)pentyl]pyridine (2.52 g, Example 11b)) and tri-isopropylborate (1.68 ml) in tetrahydrofuran (20 ml) to afford the sub-title compound as a foam (1.22 g) after chromatography on silica eluting with ethyl acetate and then ethyl acetate:methanol (4:1).
MS (APCI) 416 (M+H)$^+$
$^1$H NMR (CDCl$_3$) 8.60–8.53 (2H, m); 7.95 (2H, d); 7.6–7.54 (1H, m) 7.26–7.22 (1H, m) 6.86 (2H, d); 4.33–4.27 (1H, m); 3.93–3.86 (1H, m); 2.82–2.62 (2H, m); 1.98–1.75 (2H, m); 1.28 (3H, d); 0.94 (9H, s); 0.08 (6H, s).

EXAMPLE 12

(1S,2R)-2-[4'(2-Hydroxy-1-methyl-4-pyridin-3-ylbutoxy)biphenyl-3-yl]-N-methylacetamide

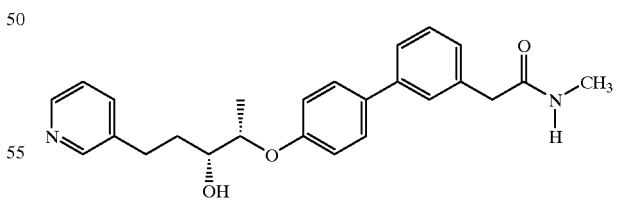

a) 2-(3-Bromophenyl)-N-methyl-acetamide

A solution of 3-bromophenyl acetic acid (2.15 g), a tetrahydrofuran solution of methyl amine (6 ml, 2M), dimethylaminopyridine (1.32 g), and 1-(3-dimethylaminopropyl)-3-ethylcarbodiimide hydrochloride (2.06 g) in dichloromethane was stirred at room temperature for 16 hrs. The organic solution was washed thrice with 2M hydrochloric acid solution, dried over magnesium sulphate, filtered and evaporated to afford a solid (1.86 g).

MS (APCI) 228/230 (M+H)+
1H NMR (CDCl3) 7.44 (2H, m); 7.21(2H, m); 5.39(1H, br.s); 3.54(2H, s); 2.79(3H, d).

b) (1S, 2R)-2-[4'(2-Hydroxy-1-methyl-4-pyridin-3-ylbutoxy)biphenyl-3-yl]-N-methylacetamide A solution of (1S,2R)-4-[2-(tert-butyldimethylsilanyloxy)-1-methyl-4-pyridin-3-ylbutoxy]benzeneboronic acid (0.20 g, Example 11), 2-(3-bromophenyl)-N-methyl-acetamide (0.21 g, Example 12a)), 2M aqueous sodium carbonate (0.57 ml) and tetrakis(triphenylphosphine)palladium (0) (0.1 g) in toluene (5 ml) and ethanol (2 ml) was heated at 100° C. for 4 hours. After cooling, the solution was concentrated under reduced pressure. Concentrated hydrochloric acid (1 ml) was added to a solution of the residue in methanol (5 ml). The suspension was stirred at room temperature for 18 hours. The mixture was concentrated under reduced pressure and the residue partitioned between ether and water. The aqueous layer was neutralised and extracted with dichloromethane (2×50 ml). The combined extracts were dried over anhydrous magnesium sulfate, filtered and concentrated under reduced pressure. The residue was purified by normal-phase HPLC eluting with a gradient of 0–25% ethanol in dichloromethane to give the title compound as an oil (0.15 g).

MS (APCI) 405 (M+H)+
1H NMR(CDCl3) 8.51(1H, d); 8.46(1H, dd); 7.57–7.54 (1H, m); 7.52(2H, d); 7.47–7.46(1H, m); 7.43–7.38(2H, m); 7.24–7.18(2H, m); 6.95(2H, d);5.40(1H, br.s); 4.37(1H, m); 3.88–3.85(1H, m); 3.63(2H, s); 2.98–2.91(1H, m); 2.77(3H, d); 2.68(1H, m); 2.16(1H, d); 1.89–1.82(2H, m); 1.31(3H, d).

EXAMPLE 13

(3R,4S)-4-(4'-Chloro-2'-fluorobiphenyl-4-yloxy)-1-pyridin-3-yl-pentan-3-ol

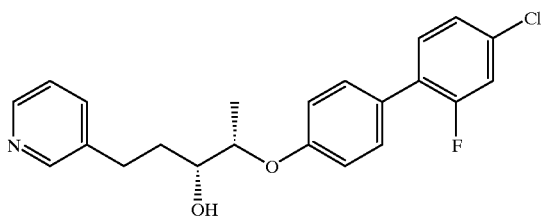

Prepared according to the method described in Example 12b) from (1S,2R)-4-[2-(tert-butyldimethylsilanyloxy)-1-methyl-4-pyridin-3-ylbutoxy]benzeneboronic acid (0.20 g, Example 11)), 1-bromo-4-chloro-2-fluorobenzene (0.21 g), 2M aqueous sodium carbonate (0.57 ml) and tetrakis(triphenylphosphine)palladium (0) (0.1 g) in toluene (5 ml) and ethanol (2 ml). The reaction mixture was heated at 100° C. for 4 hours. After cooling, the solution was concentrated under reduced pressure.

Concentrated hydrochloric acid (1 ml) was added to a solution of the residue in methanol (5 ml) and the suspension was stirred at room temperature for 6 hours. After work up, the residue was purified by normal-phase HPLC eluting with a gradient of 0–25% ethanol in dichloromethane to give an oil (0.13 g).

MS (APCI) 386 (M+H)+
1HNMR(CDCl3) 8.51(1H,d); 8.45(1H,dd); 7.56–7.54 (1H,m); 7.43(2H,dd); 7.33(1H,t); 7.26–7.15(3H,m); 6.94 (2H,d); 4.41–4.37(1H,m); 3.87–3.86(1H,m); 3.0–2.95(1H, m); 2,80–2.75(1H,m); 2.15(1H,d); 1.87–1.84(2H,m); 1.31 (3H,d).

EXAMPLE 14

3R,4S)-4-(4'-Chlorobiphenyl-4-yloxy)-1-pyridin-3-yl-pentan-3-ol

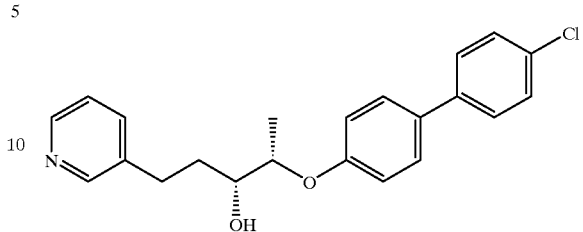

Prepared according to the method described in Example 12b) from (1S,2R)-4-[2-(tert-butyldimethylsilanyloxy)-1-methyl-4-pyridin-3-ylbutoxy]benzeneboronic acid (0.20 g, Example 11)), 4-chloro-iodobenzene (0.24 g), 2M aqueous sodium carbonate (0.5 ml) and tetrakis(triphenylphosphine) palladium (0) (0.1 g) in toluene (4 ml) and ethanol (1 ml). The reaction mixture was heated at 100° C. for 4 hours. After cooling, the solution was concentrated under reduced pressure. Concentrated hydrochloric acid (1 ml) was added to a solution of the residue in methanol (5 ml) and the suspension was stirred at room temperature for 3 hours. After work up, the residue was purified by normal-phase HPLC eluting with a gradient of 0–25% ethanol in dichloromethane to give a gum, from which the oxalate salt was made (0.11 g).

m.p. 133–135° C.
MS (APCI) 368 (M+H)+
1H NMR (DMSO) 8.44(1H, s); 8.38(1H d); 7.63–7.62 (3H, m); 7.56(2H, d); 7.46(2H d); 7.3(1H, q); 7.00(2H, d); 5.00(1H d); 4.37–4.3(1H, m); 3.6–3.5(1H, m); 2.87–2.75 (1H,m); 2.7–2.6(1H, m); 1.93–1.8(1H, m); 1.7–1.6(1H, m); 1.24(3H, d).

EXAMPLE 15

3R,4S)-4-(5'-Methoxy-2'-methylbiphenyl-4-yloxy)-1-pyridin-3-yl-pentan-3-ol

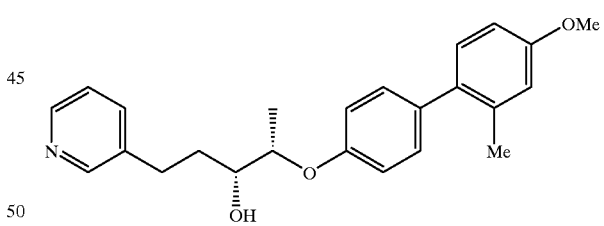

Prepared according to the method described in Example 12b) from (1S,2R)-4-[2-(tert-butyldimethylsilanyloxy)-1-methyl-4-pyridin-3-ylbutoxy]enzeneboronic acid (0.20 g, Example 11)), 4-bromo-3-methylanisole (0.2 g), 2M aqueous sodium carbonate (0.5 ml) and tetrakis(triphenylphosphine)palladium (0) (0.1 g) in toluene (4 ml) and ethanol (1 ml). The reaction mixture was heated at 100° C. for 4 hours. After cooling, the solution was concentrated under reduced pressure. Concentrated hydrochloric acid (1 ml) was added to a solution of the residue in methanol (5 ml) and the suspension was stirred at room temperature for 6 hours. After work up, the residue was purified by normal-phase HPLC eluting with a gradient of 0–25% ethanol in dichloromethane to give a gum, from which the oxalate salt was prepared (0.11 g).

m.p. 86–88° C.

MS (APCI) 377 (M+H)+ (free base)

1H NMR (DMSO) 8.47(1H, s); 8.41(1H, d); 7.68(1H, d); 7.34(1H, q); 7.16(2H, d); 7.07(1H, d); 6.92(2H, d); 6.85–6.75(2H, m); 4.29(1H, t); 3.75(3H, s); 3.6–3.5(1H, m); 2.9–2.7(2H, m); 2.2(3H, s); 1.95–1.8(1H, m); 1.72–1.6(1H, m); 1.24(3H, d).

EXAMPLE 16

(3R,4S)-4-(3',4'-Dichlorobiphenyl-4-yloxy)-1-pyridin-3-yl-pentan-3-ol, oxalic acid salt

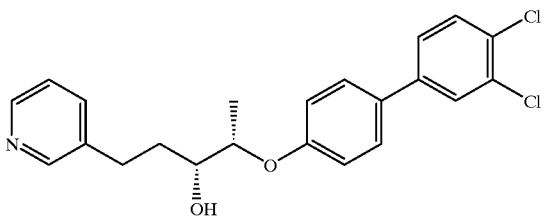

Prepared according to the method described in Example 12b) from (1S,2R)-4-[2-(tert-butyldimethylsilanyloxy)-1-methyl-4-pyridin-3-ylbutoxy]benzeneboronic acid (0.20 g, Example 11)), 3,4-dichloriodobenzene (0.273 g), 2M aqueous sodium carbonate (0.5 ml) and tetrakis (triphenylphosphine)palladium (0) (0.025 g) in toluene (5 ml) and ethanol (1 ml). The reaction mixture was heated at 100° C. for 4 hours. After cooling, the solution was concentrated under reduced pressure. Concentrated hydrochloric acid (1 ml) was added to a solution of the residue in 4:1 methanol:water (5 ml) and the suspension was stirred at room temperature for 3 hours. After work up, the residue was purified by normal-phase HPLC eluting with a gradient of 0–25% ethanol in dichloromethane to give a gum, of which the oxalate salt was made (0.23 g).

m.p. 86.4–88.4° C.

MS (APCI) 402/404 (M+H)+ (free base)

1H NMR (DMSO) 8.51(1H, d); 8.46(1H, dd); 7.62(1H, d); 7.55(1H, dt); 7.48–7.45(3H, m); 7.36(1H, dd); 7.23(1H, dd); 6.93(2H,d); 4.39(1H, dq); 3.87–3.85(1H, m); 2.95–2.91 (1H, m); 2.76–2.77(1H, m); 2.21(1H, br.s); 1.89–1.84(2H, m); 1.30(3H, d).

EXAMPLE 17

Comparative (1S, 2R)-4'-(2-Hydroxy-1-methyl-4-pyridin-3-yl-butoxy)biphenyl-3-sulfonic acid (2-morpholin-4-ylethyl)amide

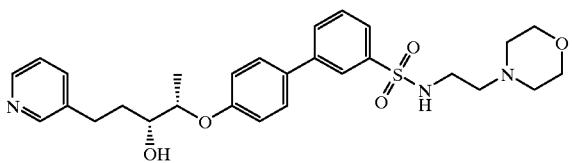

a) 3-Bromo-N-(2-morpholin-4-yl-ethyl)benzenesulfonamide hydrochloride 4-(2-Aminoethyl)morpholine (2.54 g) was added, dropwise to a stirred solution of 3-bromobenzenesulphonyl chloride (5.0 g) in ether (50 ml) at 5° C. The resulting suspension was stirred for 30 minutes and filtered to afford the sub-titled compound as a solid (4.45 g)

m.p. 82.4–84.0° C.

MS (APCI) 349/351 (M+H)+ (free base)

1H NMR (DMSO) 7.96(1H, t); 7.88–7.80(3H, m); 7.56 (1H, t); 3.59(2H, t); 3.50(2H, t); 2.92(2H, t); 2.39(2H, t); 2.35–2.20 (2H, br).

b) (1S, 2R)-4'-(2-Hydroxy-1-methyl-4-pyridin-3-yl-butoxy) biphenyl-3-sulfonic acid (2-morpholin-4-ylethyl)amide Prepared according to the method described in Example 12b) from (1S,2R)-4-[2-(tert-butyldimethylsilanyloxy)-1-methyl-4-pyridin-3-ylbutoxy],enzeneboronic acid (0.20 g, Example 11)), 3-bromo-N-(2-morpholin-4-yl-ethyl)-benzenesulfonamide hydrochloride (0.385 g, Example 17a)), 2M aqueous sodium carbonate (0.5 ml) and tetrakis (triphenylphosphine)palladium (0) (0.025 g) in toluene (5 ml) and ethanol (1 ml). The reaction mixture was heated at 100° C. for 4 hours. After cooling, the solution was concentrated under reduced pressure. Concentrated hydrochloric acid (1 ml) was added to a solution of the residue in 4:1 methanol:water (5 ml) and the suspension was stirred at room temperature for 3 hours. After work up, the residue was purified by normal-phase HPLC eluting with a gradient of 0–25% ethanol in dichloromethane to give a gum, of which the oxalate salt was prepared as a gum (0.295 g).

MS (APCI) 526 (M+H)+ (free base)

1H NMR (DMS0) 8.46(1H, d); 8.41(1H, dd); 7.99(1H, d); 7.90(2H, dt); 7.74(1H, dd); 7.69–7.64(4H, m); 7.33(1H, dd);7.05(2H, d); 4.36 (1H, p); 3.69–3.66(4H, m); 3.58–3.54 (1H, m); 3.10–3.04(2H, br); 2.90–2.81(7H, br.m); 2.75–2.61 (2H, m); 1.94–1.80(2H, m); 1.76–1.62(2H, m); 1.25(3H, d).

EXAMPLE 18

(3R,4S)-4-(2',4'-Dichlorobiphenyl-4-yloxy)-1-pyridin-3-yl-pentan-3-ol

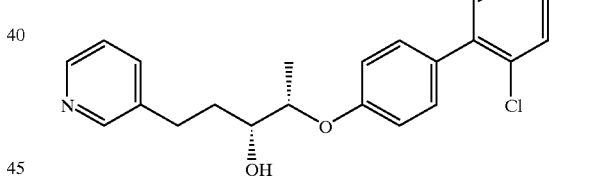

Prepared according to the method described in Example 12b) from (1S,2R)-4-[2-(tert-butyldimethylsilanyloxy)-1-methyl-4-pyridin-3-ylbutoxy]benzeneboronic acid (0.20 g, Example 11)), 1-bromo-2,4-dichlorobenzene (0.218 g), 2M aqueous sodium carbonate (0.5 ml) and tetrakis (triphenylphosphine)palladium (0) (0.020 g)in toluene (5 ml) and ethanol (2 ml). The reaction mixture was heated at 100° C. under nitrogen for 4 hours. After cooling, the solution was concentrated under reduced pressure. Concentrated hydrochloric acid (1 ml) was added to a solution of the residue in methanol (5 ml) and the suspension was stirred at room temperature for 5 hours. The mixture was concentrated under reduced pressure and the residue partitioned between diethyl ether and water. The aqueous layer was neutralised with sodium hydrogen carbonate solution (in water) and the aqueous solution was extracted with ethyl acetate. The combined organic phases were dried over anhydrous magnesium sulfate, filtered and concentrated under reduced pressure. The residue was purified by normal-phase HPLC eluting with a gradient of 0–25% ethanol in dichloromethane to give a solid (0.064 g) from which the oxalate salt was prepared (0.054 g).

m.p. 98–100° C.

MS (APCI) 402.1, 404.1, 405.1 (M+H)$^+$ $^1$H NMR (DMSO) 8.44(2H, m); 7.69(2H, bs); 7.49–7.32 (5H, m); 7.00(2H, d); 4.34(1H, m); 3.38(1H, m); 2.83(1H, m); 2.70(1H, m); 1.86(1H, m); 1.66(1H, m); 1.25(3H, d).

EXAMPLE 19

(1S, 2R)-4'-(2-Hydroxy-1-methyl-4-pyridin-3-yl-butoxy)biphenyl-3-sulfonic acid methylamide

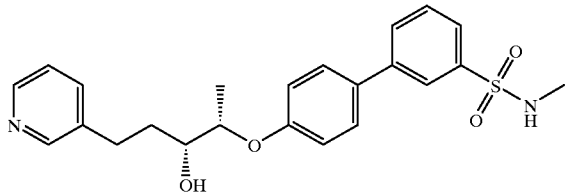

a) 3-Bromo-N-methyl-benzenesulfonamide

Methylamine was bubbled through a solution of 3-bromobenzenesulfonyl chloride (5.0 g) in tetrahydrofuran (50 ml) at 0° C. The resulting suspension was stirred for 3 hours, filtered and concentrated at reduced pressure. The residue was triturated with hexane and filtered to afford the sub-titled compound as a solid (4.52 g).

m.p. 88–89° C.

MS (APCI) 250 (M+H)$^+$ (free base)

$^1$H NMR (DMSO) 8.02(1H, m); 7.80(1H, m); 7.72(1H, m) 7.42(1H, t); 4.44(1H, bm); 2.70(3H, d).

b) (1S, 2R)-4'-(2-Hydroxy-1-methyl-4-pyridin-3-yl-butoxy)biphenyl-3-sulfonic acid methylamide Prepared according to the method described in Example 12b) from (1S,2R)-4-[2-(tert-butyldimethylsilanyloxy)-1-methyl-4-pyridin-3-ylbutoxy],enzeneboronic acid (0.20 g, Example 11)), 3-Bromo-N-methyl-benzenesulfonamide (0.240 g, Example 19a)), 2M aqueous sodium carbonate (0.55 ml) and tetrakis(triphenylphosphine)palladium (0) (0.020 g) in toluene (5 ml) and ethanol (2 ml). The reaction mixture was heated at 100° C. for 4 hours. After cooling, the solution was concentrated under reduced pressure. Concentrated hydrochloric acid (1 ml) was added to a solution of the residue in methanol (4 ml) and the suspension was stirred at room temperature for 1.5 hours. The mixture was concentrated under reduced pressure and the residue partitioned between diethyl ether and water. The aqueous layer was basified with 10% sodium hydrogen carbonate solution and the aqueous solution was extracted with ethyl acetate. The combined organic phases were dried over anhydrous magnesium sulfate, filtered and concentrated under reduced pressure. The residue was purified by normal-phase HPLC eluting with a gradient of 0–25% ethanol in dichloromethane to give a foam (0.0495 g).

MS (APCI) 427.1 (M+H)$^+$ $^1$H NMR (DMSO) 8.44(1H, m); 8.39(1H, dt); 7.95(1H, d); 7.89(1H, dt); 7.72–7.60 (4H, m); 7.47(1H, q); 7.30(1H, dd); 7.05(2H, d); 5.01(1H, d); 4.36(1H, m); 3.56(1H, m); 2.67(1H, m), 2.43(3H, d); 1.87(1H, m); 1.65(1H, m), 1.25 (3H, d).

EXAMPLE 20

Comparative (1S, 2R)-4'-(2-Hydroxy-1-methyl-4-pyridin-3-yl-butoxy)biphenyl-3-sulfonic acid (2-pyrrolidin-1-ylethyl)amide

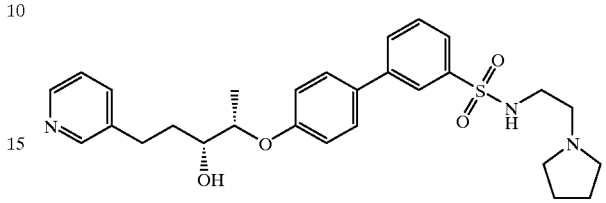

3a) 3-Bromo-N-(2-pyrrolidin-1-yl-ethyl)benzenesulfonamide hydrochloride

N-(2-Aminoethyl)pyrrolidine (1.61 g) was added dropwise to a solution of 3-bromobenzenesulfonyl chloride (3.61 g) in diethyl ether (100 ml) at room temperature. The resulting suspension was stirred for 30 minutes and filtered to afford the sub-title compound as a solid (4.48 g).

m.p. 144–146° C.

MS (APCI) 333/335 [M—HCl]$^+$ $^1$H NMR (DMSO) 8.28(1H, bs); 7.99(1H, m); 7.93–7.84 (2H, m); 7.60(1H, t) 3.3–2.9(8H, bm); 1.88(4H, bs).

b) (1S, 2R)-4'-(2-Hydroxy-1-methyl-4-pyridin-3-yl-butoxy) biphenyl-3-sulfonic acid (2-pyrrolidin-1-ylethyl)amide Prepared according to the method described in Example 12b) from (1S,2R)-4-[2-(tert-butyldimethylsilanyloxy)-1-methyl-4-pyridin-3-ylbutoxy])enzeneboronic acid (0.20 g, Example 11)), 3-bromo-N-(2-pyrrolidin-1-yl-ethyl)benzenesulfonamide hydrochloride (0.355 g, Example 20a)), 2M aqueous sodium carbonate (0.55 ml) and tetrakis (triphenylphosphine)palladium (0) (0.020 g) in toluene (5 ml) and ethanol (1 ml). The reaction mixture was heated at 100° C. for 4 hours. After cooling, the solution was concentrated under reduced pressure. Concentrated hydrochloric acid (1 ml) was added to a solution of the residue in methanol (4 ml) and the suspension was stirred at room temperature for 0.75 hours. The mixture was concentrated under reduced pressure and the residue partitioned between diethyl ether and water. The aqueous layer was basified with sodium hydrogen carbonate solution and the aqueous solution was extracted with ethyl acetate. The combined organic extracts were dried over anhydrous magnesium sulfate, filtered and concentrated under reduced pressure. The residue was purified by normal-phase HPLC eluting with a gradient of 0–25% ethanol in dichloromethane to give a foam (0.113 g).

MS (APCI) 510.1 (M+H)$^+$ $^1$H NMR (DMSO) 8.44(1H, m); 8.39(1H, m); 8.00(1H, m); 7.86(1H, dt); 7.72(1H, m); 7.63(4H, m); 7.30(1H, dd); 7.05(2H, d); 5.01(1H, d); 4.36(1H, quintet); 3.57(1H, m); 2.92(2H, t); 2.89(1H, m); 2.67(1H, m); 2.40(2H, t); 2.31(4H, m); 1.87(1H, m); 1.63(1H, m); 1.58(4H, m); 1.25(3H, d).

EXAMPLE 21

(1S,2R)-4'-(2-Hydroxy-1-methyl-4-pyridin-3-yl-butoxy)-2-methyl-biphenyl-4-carbonitrile

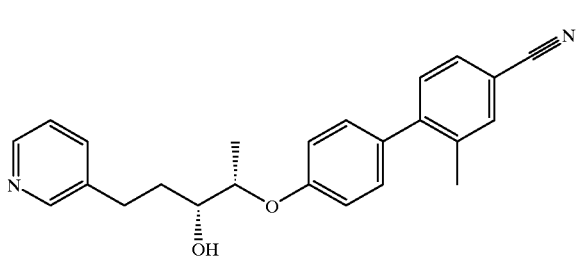

Prepared according to the method described in Example 12b) from (1S,2R)-4-[2-(tert-butyldimethylsilanyloxy)-1-methyl-4-pyridin-3-ylbutoxy]benzeneboronic acid (0.20 g, Example 11)), 4-bromo-3-methylbenzonitrile (0.20 g), 2M aqueous sodium carbonate solution (0.5 ml) and tetrakis (triphenylphosphine)palladium (0) (0.02 g) in toluene (5 ml) and ethanol (2 ml). The reaction mixture was heated at 100° C. under nitrogen for 4 hours. After cooling, the solution was concentrated under reduced pressure. Concentrated hydrochloric acid (1 ml) was added to a solution of the residue in methanol (5 ml) and the suspension stirred at room temperature for 2 hours. The mixture was concentrated under reduced pressure and the residue partitioned between diethyl ether and water. The aqueous layer was neutralised with a saturated solution of sodium bicarbonate in water and extracted with dichloromethane. The combined organics were dried over anhydrous magnesium sulfate, filtered and concentrated under reduced pressure. The residue was purified by normal-phase HPLC eluting with a gradient of 0–25% ethanol in dichloromethane to give an oil (0.15 g)

MS (APCI) 373 (M+H)+

$^1$H NMR (CDCl$_3$) 8.52(1H, d); 8.46(1H, dd); 7.53(3H, m); 7.25(4H, m); 6.94(2H, 4.40(1H, m); 3.87(1H, m); 2.96 (1H, m); 2.75(1H, m); 2.30(3H, s); 2.17(1H, brs); 1.88(2H, m); 1.33(3H, d).

EXAMPLE 22

(1S,2R)-N-[2-Chloro-4'-(2-hydroxy-1-methyl-4-pyridin-3-yl-butoxy)-biphenyl-4-yl]-acetamide, oxalic acid salt

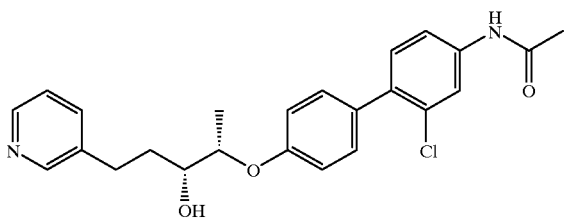

(3R,4S)-4-(4'-Amino-2'-chloro-biphenyl-4-yloxy)-1-pyridin-3-yl-pentan-3-ol, oxalic acid salt

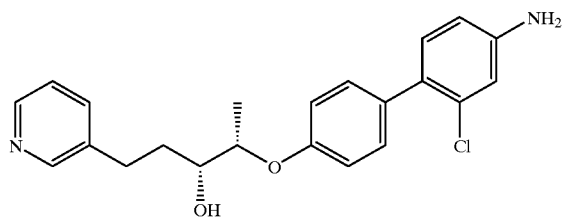

Prepared according to the method described in Example 12b) from (1S,2R)-4-[2-(tert-butyldimethylsilanyloxy)-1-methyl-4-pyridin-3-ylbutoxy]benzeneboronic acid (0.20 g, Example 11)), 4-bromo-3-chloroacetanilide (0.20 g), 2M aqueous sodium carbonate solution (0.5 ml) and tetrakis (triphenylphosphine)palladium (0) (0.02 g) in toluene (5 ml) and ethanol (2 ml). The reaction mixture was heated at 100° C. under nitrogen for 4 hours. After cooling, the solution was concentrated under reduced pressure. Concentrated hydrochloric acid (1 ml) was added to a solution of the residue in methanol (5 ml) and the suspension stirred at room temperature for 16 hours. The mixture was concentrated under reduced pressure and the residue partitioned between diethyl ether and water. The aqueous layer was neutralised with a saturated solution of sodium bicarbonate in water and extracted with dichloromethane. The combined organic extracts were dried over anhydrous magnesium sulfate, filtered and concentrated under reduced pressure. The residue was purified by normal-phase HPLC eluting with a gradient of 0–25% ethanol in dichloromethane to give two products, the first was the title compound (0.05 g) as an oil from which the oxalate salt was prepared as a foam (0.05 g);

MS (APCI) 425 (M+H)+

$^1$H NMR (DMSO) 10.16(1H, s); 8.47(1H, s); 8.41(1H, d); 7.88(1H, d); 7.68(1H, d); 7.49(1H, dd); 7.35–7.29(3H, m); 6.96(2H, d); 6.68(1H, dd); 4.32(1H, m); 3.56(1H, m); 2.82 (1H, m); 2.66(1H, m); 2.07(3H, s); 1.86(1H, m); 1.66(1H, m); 1.25(3H, d).

On further elution a second compound (3R,4S)-4-(4'-amino-2'-chloro-biphenyl-4-yloxy)-1-pyridin-3-yl-pentan-3-ol (0.10 g), was obtained as an oil from which the solid oxalate salt was also prepared (0.10 g).

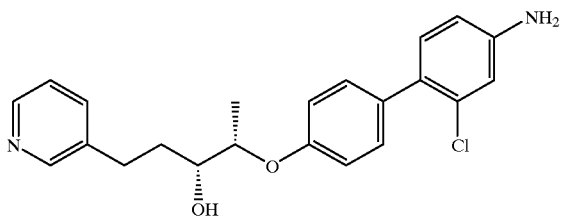

M.P. 142–145° C.
MS (APCI) 383 (M+H)+
¹H NMR (DMSO) 8.47(1H, d); 8.42(1H, dd); 7.70(1H, d); 7.35(1H, m); 7.22(2H, d); 7.00(1H, d); 6.91(2H, d); 6.68(1H, d); 6.55(1H, dd); 4.28(1H, m); 3.54(1H, m); 2.80 (1H, m); 2.69(1H, m); 1.87(1H, m); 1.64(1H, m); 1.24(3H, d).

EXAMPLE 23

Comparative (1S, 2R)-4'-(2-Hydroxy-1-methyl-4-pyridin-3-yl-butoxy)biphenyl-3-sulfonic acid (2-dimethylaminoethyl)amide

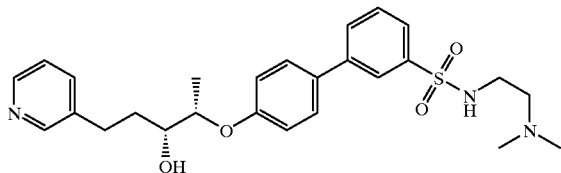

a) 3-Bromo-N-(2-dimethylamino-ethyl)benzenesulfonamide hydrochloride

N,N-Dimethylethylenediamine (1.76 g) was added dropwise to a solution of 3-bromobenzenesulfonyl chloride (5.11 g) in diethyl ether (100 ml) at room temperature. The resulting suspension was stirred for 30 minutes and filtered to afford the sub-title compound as a solid (4.31 g).

m.p. 154–156° C.
MS (APCI) 305/307 [(M—HCl)+1]+
¹H NMR (DMSO) 8.32(1H, bs); 8.00(1H, m); 7.95–7.85 (2H, m); 7.60(1H, t); 3.15(4H,s); 2.75(6H,s).

b) (1S, 2R)-4'-(2-Hydroxy-1-methyl-4-pyridin-3-yl-butoxy)biphenyl-3-sulfonic acid (2-dimethylaminoethyl)amide Prepared according to the method described in Example 12b) from (1S,2R)-4-[2-(tert-butyldimethylsilanyloxy)-1-methyl-4-pyridin-3-ylbutoxy]enzeneboronic acid (0.20 g, Example 11)), 3-bromo-N-(2-dimethylamino-ethyl)benzenesulfonamide hydrochloride (0.331 g, Example 23a)), 2M aqueous sodium carbonate (0.723 ml) and tetrakis (triphenylphosphine)palladium (0) (0.1 g) in toluene (5 ml) and ethanol (2 ml). The reaction was heated at 110° C. for 6 hours. After cooling, the solution was concentrated under reduced pressure the residue was dissolved in methanol (10 ml), concentrated hydrochloric acid (1 ml) was added and the solution stirred at room temperature for 18 hours. The mixture was concentrated under reduced pressure and neutralised using saturated sodium hydrogen carbonate and extracted with ethyl acetate. The combined extracts were dried over anhydrous magnesium sulfate, filtered and concentrated under reduced pressure. The residue was purified by normal-phase HPLC eluting with a gradient of 0–10% ethanol in dichloromethane to give the title compound as a colourless oil (0.087 g).

MS (APCI) 484 (M+H)+
¹H NMR(CDCl₃) 8.51(1H,s); 8.45(1H,d); 8.05(1H, t); 7.80(1H, dd); 7.75(1H, dd); 7.60–7.5(4H, m); 7.3–7.2(1H, m); 7.0(2H, d); 4.45–4.35(1H, m); 3.95–3.80(1H, m); 3.05–2.80(3H, m); 2.80–2.70(1H, m); 2.40–2.30(21H, m); 2.1(6H, s); 1.90–1.80(4H, m); 1.30(32H, d).

EXAMPLE 24

(1S,2R)-2-[4'-(2-Hydroxy-1-methyl-4-pyridin-3-ylbutoxy)biphenyl-4-yl]-N-methylacetamide

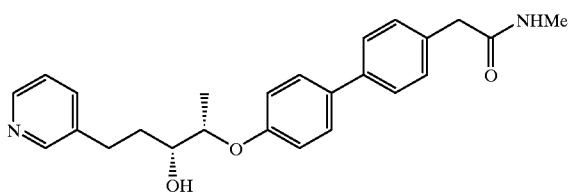

a) 2-(3-Bromophenyl)-N-methyl-acetamide 1-(3-Dimethylaminopropyl)-3-ethylcarbodiimide 4-hydrochloride (8.88 g), 4-dimethylaminopyridine (5.67 g) and a 2M solution of methylamine in tetrahydrofuran (23 ml) were added to a solution of 4-bromophenylacetic acid (5.0 g) in dichloromethane (100 ml). The mixture was stirred overnight at room temperature. The reaction mixture was washed with 2M hydrochloric acid (3×100 ml), the organic layer was dried over anhydrous magnesium sulfate, filtered and concentrated. The sub-title compound was obtained as a solid (4.74 g) after recrystallisation from 1% hexane in ethyl acetate.

m.p. 117–118° C.
MS (APCI) 228/230(M+H+)
¹H NMR(CDCl₃) 7.96(1H, s); 7.48(2H, d); 7.20(2H, d); 3.40(2H, s); 2.60, (3H, d).

b) (1S,2R)-2-[4'-(2-Hydroxy-1-methyl-4-pyridin-3-ylbutoxy)biphenyl-4-yl]-N-methylacetamide Prepared according to the method described in Example 12b) from (1S,2R)-4-[2-(tert-butyldimethylsilanyloxy)-1-methyl-4-pyridin-3-ylbutoxy]benzeneboronic acid (0.20 g, Example 11)), 2-(3-bromophenyl)-N-methyl-acetamide (0.244 g, Example 24a)), 2M aqueous sodium carbonate (0.265 ml) and tetrakis(triphenylphosphine)palladium (0) (0.1 g) in toluene (5 ml) and ethanol (2 ml). The reaction was heated at 110° C. for 6 hours. After cooling, the solution was concentrated under reduced pressure the residue was dissolved in methanol (10 ml), concentrated hydrochloric acid (1 ml) was added and the solution stirred at room temperature for 18 hours. The mixture was concentrated under reduced pressure the residue was neutralised using saturated sodium hydrogen carbonate and extracted with ethyl acetate. The combined extracts were dried over anhydrous magnesium sulfate, filtered and concentrated under reduced pressure. The residue was purified by normal-phase HPLC eluting with a gradient of 0–10% ethanol in dichloromethane to give the title compound as an oil which was converted to the oxalic acid salt by treatment with a saturated ethereal solution of oxalic acid to give the title compound as a gum (0.123 g).

MS (APCI) 405 [(M+H)-oxalate]+
¹H NMR(DMSO) 8.45(1H, s); 8.40(1H, d); 7.95(1H, d); 7.70(1H, d); 7.50(4H, dt); 7.35(1H, dd); 7.30(2H, d); 7.0 (2H, d); 4.35–4.30(1H, m); 3.55–3.50(1H, m); 3.45–3.40 (2H, m); 2.85–2.75(1H, m); 2.70–2.60(1H, m); 2.55(3H, d); 1.85–1.80(1H, m); 1.70–1.55(1H, m); 1.25(3H, d).

EXAMPLE 25

(1S,2R)-2-[4'(2-Hydroxy-1-methyl-4-pyridin-3-ylbutoxy)biphenyl-3-yl]-N,N-dimethylacetamide

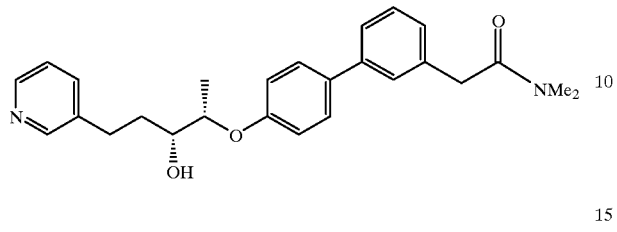

a) 2-(3-Bromophenyl)-N,N-dimethyl-acetamide

Prepared according to the method described in Example 24a) from 1-(3-is dimethylaminopropyl)-3-ethylcarbodiimide 4-hydrochloride (2.15 g), 4-dimethylaminopyridine (3.82 g), a 2M solution of dimethylamine in tetrahydrofuran (10 ml) and a solution of 3-bromophenylacetic acid (2.15 g) in dichloromethane (100 ml). The mixture was stirred overnight at room temperature. The reaction mixture was washed with 2M hydrochloric acid (3×100 ml), the organic layer was dried over anhydrous magnesium sulfate, filtered and concentrated. The sub-title compound was obtained as an oil (2.89 g).

MS (APCI) 242/244(M+H$^+$)

$^1$H NMR(CDCl$_3$) 7.45–7.35(2H, m); 7.20–7.15(2H, m); 3.65(2H, s); 3.05(3H, s); 2.95(3H, s).

b) (1S, 2R)-2-[4'(2-Hydroxy-1-methyl-4-pyridin-3-ylbutoxy)biphenyl-3-yl]-N,N-dimethylacetamide Prepared according to the method described in Example 12b) from (1S,2R)-4-[2-(tert-butyldimethylsilanyloxy)-1-methyl-4-pyridin-3-ylbutoxy])enzeneboronic acid (0.20 g, Example 11), 2-(3-bromophenyl)-N,N-dimethyl-acetamide (0.234 g, Example 25a)), 2M aqueous sodium carbonate (0.241 ml) and tetrakis(triphenylphosphine)palladium (0) (0.1 g) in toluene (5 ml) and ethanol (2 ml). The reaction was heated at 110° C. for 6 hours. After cooling, the solution was concentrated under reduced pressure the residue was dissolved in methanol (10 ml), concentrated hydrochloric acid (1 ml) was added and the solution stirred at room temperature for 18 hours. The mixture was concentrated under reduced pressure the residue was neutralised using saturated sodium hydrogen carbonate and extracted with ethyl acetate. The combined extracts were dried over anhydrous magnesium sulfate, filtered and concentrated under reduced pressure. The residue was purified by normal-phase HPLC eluting with a gradient of 0–10% ethanol in dichloromethane to give the title compound as an oil (0.144 g).

MS (APCI) 419 (M+H)$^+$ $^1$HNMR(CDCl$_3$) 8.50(1H, d); 8.45(1H, d); 7.55(1H, d); 7.50(2H, d); 7.45(2H, d); 7.35(1H, t); 7.25–7.15(2H, m); 6.95(2H, d); 4.45–4.35(1H, m); 3.90–3.80(1H, m); 3.75(2 H, s); 3.00(3H, s); 2.95(3H, s); 2.95–2.90(1H, m); 2.80–2.65 (1H, m); 2.20(1H, d); 1.90–1.80(2H, m); 1.25(3H, d).

EXAMPLE 26

Comparative (4S,3R)-4-(4'-Methanesulfonyl-biphenyl-4-yloxy)-1-pyridin-3-yl-pentan-3-ol

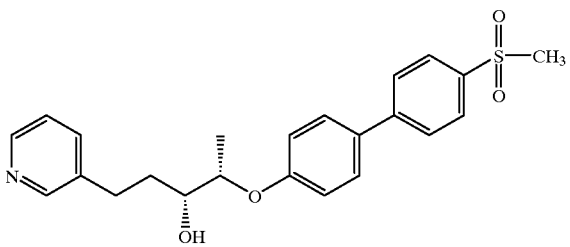

Prepared according to the method described in Example 12b) from (1S,2R)-4-[2-(tert-butyldimethylsilanyloxy)-1-methyl-4-pyridin-3-ylbutoxy]benzeneboronic acid (0.25 g, Example 11c)), 4-bromophenylmethylsulfone (0.19 g), 2M aqueous sodium carbonate (0.64 ml) and tetrakis (triphenylphosphine)palladium (0) (0.016 g) in ethanol (3 ml) with heating at 90 C. for 4 hours. After cooling, the solution was concentrated under reduced pressure. The residue was partitioned between water and ethyl acetate. The organic layer was concentrated under reduced pressure. The residue was purified by column chromatography over silica gel eluting with ethyl acetate to give an oil. Concentrated hydrochloric acid (1 ml) was added to a solution of the oil in methanol (5 ml). The solution was stirred at room temperature for 18 hours. The mixture was concentrated under reduced pressure. The residue was neutralised using saturated sodium bicarbonate solution and extracted with ethyl acetate. The combined extracts were dried over anhydrous magnesium sulfate, filtered and concentrated under reduced pressure to give a solid (0.17 g).

MS(APCI) 412 (M+H)$^+$ $^1$H NMR(CDCl$_3$) 8.44(1H, d); 8.39(1H, dd); 7.95(2H, d); 7.88(2H, d); 7.69–7.61(3H, m); 7.32–7.29(1H, m); 7.04(2H, d); 5.01(1H, d); 4.38–4.35(1H, m); 3.57–3.55(1H, m); 3.24 (3H, s); 2.81–2.67(2H, m); 1.941.79(1H, m); 1.72–1.57(1H, m); 1.25(3H, d).

EXAMPLE 27

(3R,4S)-4-[3'-(2-Dimethylaminoethyl)biphenyl-4-yloxy]-1-pyridin-3-yl-pentan-3-ol

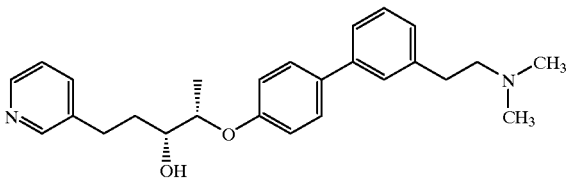

a) [2-(3-Bromophenyl)ethyl]dimethylamine hydrochloride

Borane in tetrahydrofuran (1.0M, 24.7 ml) was added dropwise to a tetrahydrofuran solution of 2-(3-bromophenyl)-N,N-dimethyl-acetamide (1.5 g, Example 25a)) at 0° C. Once addition was complete the solution was refluxed at 90° C. for 20 hours. The solution was cooled to room temperature, acidified with hydrochloric acid (6M, 10 ml) and refluxed for a further hour. The solution was cooled to room temperature and extracted with diethyl ether. The aqueous layer was basified with 10% aqueous sodium hydroxide and extracted with ethyl acetate. The extracts were dried over anhydrous magnesium sulfate, filtered and concentrated. The residue was converted to the hydrochloride salt by treatment with a solution of 4M hydrogen chloride in dioxan to give the sub-title compound as a hygroscopic gum (0.949 g).

MS (APCI) 228/230[(M—HCl)+H]⁺

¹H NMR(DMSO) 7.63(1H, s); 7.55–7.45(1H, m); 7.35–7.25(2H, m); 3.28–3.24(2H, m); 3.05–3.00(2H, m); 2.84(6H, s).

b) (3R,4S)-4-[3'-(2-Dimethylaminoethyl)biphenyl-4-yloxy]-1-pyridin-3-yl-pentan-3-ol Prepared according to the method described in Example 12b) from (1S,2R)-4-[2-(tert-butyldimethylsilanyloxy)-1-methyl-4-pyridin-3-ylbutoxy]benzeneboronic acid (0.2 g, Example 11), [2-(3-bromophenyl)ethyl]dimethylamine hydrochloride (0.21 g, Example 27a)), aqueous sodium carbonate (2M, 0.82 ml) and tertakistriphenylphosphine palladium (0) (0.1 g) in toluene (5 ml) and ethanol (2 ml). The reaction was heated at 100° C. for 4 hours. After cooling, the solution was concentrated under reduced pressure. Concentrated hydrochloric acid (1 ml) was added to a solution of the residue in methanol (5 ml) and stirred at room temperature for 2 hours. After work up, the residue was purified by normal-phase HPLC eluting with a gradient of 0–25% ethanol in dichloromethane to give the title compound as an oil (0.07 g).

MS (APCI) 405 (M+H)⁺

¹H NMR(CDCl₃) 8.51(1H, d); 8.46(1H, dd); 7.57–7.54 (1H, m); 7.5(2H, d); 7.39–7.31(3H, m); 7.24–7.17(2H, m); 6.95(2H, d); 4.40–4.37(1H, m); 3.95–3.85(1H, m); 2.95–2.90(1H, m); 2.88–2.85(2H, m); 2.76–2.71(1H, m); 2.67–2.61(2H, m); 2.36(6H, s); 2.10(1H, br.s); 1.89–1.81 (2H, m); 1.31(3H, d).

EXAMPLE 28

(1S,2R)-2-[4'(2-Hydroxy-1-methyl-4-pyridin-3-ylbutoxy)biphenyl-3-yl]-1-morpholin-4-yl-ethanone oxalic acid salt

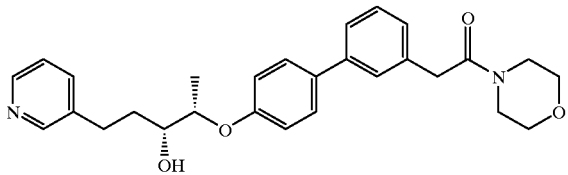

a) 3-Bromophenyl-1-morpholin-4-yl-ethanone

Prepared according to the method described in Example 24a) from 1-(3-dimethylaminopropyl)-3-ethylcarbodiimide 4-hydrochloride (0.764 g), 4-dimethylaminopyridine (0.488 g), morpholine (0.35 ml) and a solution of 3-bromophenylacetic acid (0.43 g) in dichloromethane (10 ml). The mixture was stirred overnight at room temperature. The reaction mixture was washed with 2M hydrochloric acid (3×100 ml), the organic layer was dried over anhydrous magnesium sulfate, filtered and concentrated. The sub-title compound was obtained as a solid (0.550 g).

MS (APCI) 242/244(M+H⁺)

¹H NMR(CDCl₃) 7.40(2H, m); 7.17(2H, m); 3.70(2H, s); 3.65(4H, s); 3.53(2H, m); 3.45(2H, m).

b) (1S, 2R)-2-[4'(2-Hydroxy-1-methyl-4-pyridin-3-ylbutoxy)biphenyl-3-yl]-1-morpholine-4-yl-ethanone, oxalic acid salt Prepared according to the method described in Example 12b) form (1S,2R)-4-[2-(tert-butyldimethylsilanyloxy)-1-methyl-4-pyridin-3-ylbutoxy]benzeneboronic acid (0.20 g, Example 11)), 3-bromophenyl-1-morpholin-4-yl-ethanone (0.234 g, Example 28a)), 2M aqueous sodium carbonate (0.241 ml) and tetrakis(triphenylphosphine)palladium (0) (0.1 g) in toluene (5 ml) and ethanol (2 ml). The reaction was heated at 110° C. for 6 hours. After cooling, the solution was concentrated under reduced pressure the residue was dissolved in methanol (10 ml), concentrated hydrochloric acid (1 ml) was added and the solution stirred at room temperature for 18 hours. The mixture was concentrated under reduced pressure the residue was neutralised using, saturated sodium hydrogen carbonate and extracted with ethyl acetate. The combined extracts were dried over anhydrous magnesium sulfate, filtered and concentrated under reduced pressure. The residue was purified by normal-phase HPLC eluting with a gradient of 0–10% ethanol in dichloromethane to give the title compound as an oil (0.144 g).

MS (APCI) 419 (M+H)⁺

¹H NMR(CDCl₃) 8.50(1H, d); 8.45(1H, d); 7.55(1H, d); 7.50(2H, d); 7.45(2H, d); 7.35(1H, t); 7.25–7.15(2H, m); 6.95(2H, d); 4.45–4.35(1H, m); 3.90–3.80(1H, m); 3.75(2H, s); 3.00(3H, s); 2.95(3H, s); 2.95–2.90(1H, m); 2.80–2.65 (1H, m); 2.20(1H, d); 1.90–1.80(2H, m); 1.25(3H, d).

EXAMPLE 29

(3R,4S)-4-[4-(3'-(Methylaminoethyl)biphenyl-4-yloxy]-1-pyridin-3-yl-pentan-3-ol

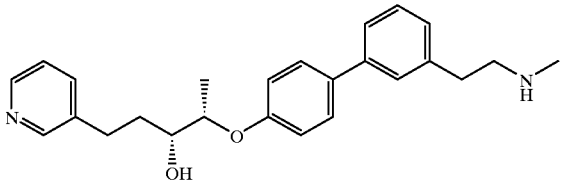

a) [2-(3-Bromophenyl)ethyl]methylamine hydrochloride

Borane in tetrahydrofuran (1.0M, 26.3 ml) was added dropwise to a tetrahydrofuran solution of 2-(3-bromophenyl)-N-methyl-acetamide (1.5 g, Example 12a)) at 0° C. Once addition was complete the solution was refluxed at 90° C. for 20 hours. The solution was cooled to room temperature, acidified with 6M hydrochloric acid (10 ml) and refluxed for a further hour. The solution was cooled to room temperature and extracted with diethyl ether. The aqueous layer was basified with 10% sodium hydroxide and extracted with ethyl acetate. The extracts were dried over anhydrous magnesium sulfate, filtered and concentrated. The residue was converted to the hydrochloride salt by treatment with a 4M solution of hydrochloric acid in dioxan to give the sub-title compound as a solid (0.727 g).

m.p. 135–136° C.

MS (APCI) 214/216[(M—HCl)+H]⁺

¹H NMR(DMSO) 9.00(1H, s); 7.51(1H, s); 7.50–7.45 (1H, m); 7.35–7.25(2H, m); 3.20–3.05(2H, m); 3.00–2.90 (2H, m); 2.55(3H, s).

b) (3R,4S)-4-[4-(3'-Methylaminoethyl)biphenyl-4-yloxy]-1-pyridin-3-yl-pentan-3-ol Prepared according to the method described in Example 12b) from (1S,2R)-4-[2-(tert-butyldimethylsilanyloxy)-1-methyl-4-pyridin-3-ylbutoxy]benzeneboronic acid (0.20 g, Example 11)), [2-(3-bromophenyl)ethyl]methylamine hydrochloride (0.241 g, Example 29a)), 2M aqueous sodium carbonate (0.72 ml) and tetrakis(triphenylphosphine) palladium (0) (0.1 g) in toluene (5 ml) and ethanol (2 ml). The reaction was heated at 110° C. for 6 hours. After cooling, the solution was concentrated under reduced pressure the residue was dissolved in methanol (10 ml), concentrated hydrochloric acid (1 ml) was added and the solution stirred at room temperature for 18 hours. The mixture was concentrated under reduced pressure the residue was neutralised using saturated sodium hydrogen carbonate and extracted with ethyl acetate. The combined extracts were dried over anhydrous magnesium sulfate, filtered and concentrated under reduced pressure. The residue was purified by normal-phase HPLC eluting with a gradient of 0–10% ethanol in 1% triethylamine in dichloromethane to give the title compound as an oil (0.14 g).

MS (APCI) 391 (M+H)+

1H NMR(CDCl3) 8.50(1H, d); 8.45(1H, dd); 7.55(1H, dd); 7.50(2H, dd); 7.40–7.30(3H, m); 7.25–7.15(2H, m); 6.95(2H, d); 4.45–4.30(1H, m); 3.90–3.80(1H, m); 3.00(4H, s); 2.95–2.90(1H, m); 2.80–2.65(1H, m); 2.50(3H, s); 1.90–1.80(2H, m); 1.30(3H,

EXAMPLE 30

(3R,4S)-4-[4'-(2-Methylaminoethyl)biphenyl-4-yloxy]-1-pyridin-3-yl-pentan-3-ol

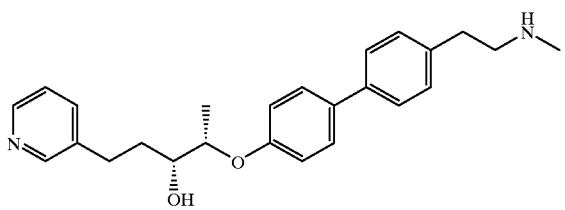

a) [2-(4-Bromophenyl)ethyl]-N-methylamine hydrochloride

Prepared according to the method described in Example 29a) from borane (1.0M solution in tetrahydrofuran, 35 ml), 4-bromophenyl acetic acid methylamide (2.0 g, Example 24a)) in dry tetrahydrofuran (60 ml) to afford the sub-title compound as a solid (0.45 g).

m.p. 198–200° C.

MS (APCI) 214 (M+H)+

1H NMR (CDCl3) 7.43(2H, d); 7.12(2H, d); 3.25–3.09 (4H, m); 2.72(3H, s).

b) (3R,4S)-4-[4'-(2-Methylaminoethyl)biphenyl-4-yloxy]-1-pyridin-3-yl-pentan-3-ol Prepared according to the method described in Example 12b) from [2-(4-bromophenyl)ethyl]-N-methylamine hydrochloride (0.214 g, Example 30a)), ethanol (1 ml), toluene (4 ml), 2M aqueous sodium carbonate (0.5 ml), (1S,2R)-4-[2-(tert-butyldimethylsilanyloxy)-1-methyl-4-pyridin-3-ylbutoxy]benzeneboronic acid (0.2 g, Example 11)), and tetrakis(triphenylphosphine)palladium (0) (0.02 g) with heating at 120° C. for 4 hours. After work-up, the residue was purified by normal-phase HPLC eluting a gradient of 0–25% ethanol in dichloromethane to give the title compound as a pale yellow solid (0.081 g).

m.p. 113–114° C.

MS (APCI) 391 (M+H)+

1H NMR (DMSO) 8.44(1H, d); 8.38(1H, d); 7.62(1H, d); 7.51(4H, t); 7.32–7.23(3H, m); 6.97(2H, d); 4.98(1H, d); 4.31(1H, q); 3.54(1H, br.d); 2.89–2.73(1H, m); 2.71(4H, s); 2.69–2.53(1H, m); 2.30(3H, s); 1.91–1.79(1H, m); 1.72–1.59(1H, m); 1.23(3H, d).

EXAMPLE 31

(1S, 2R)-4'-(2-Hydroxy-1-methyl-4-pyridin-3-ylbutoxy)biphenyl-3-yl-urea

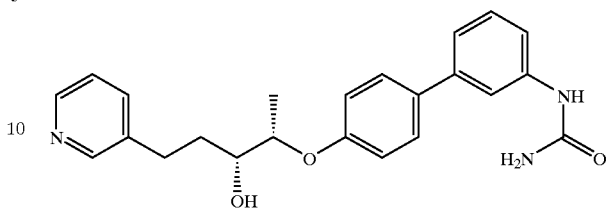

Prepared according to the method described in Example 12b) from 3-bromophenylurea (0.215 g), ethanol (1 ml), toluene (4 ml), 2M aqueous sodium carbonate (0.5 ml), (1S,2R)-4-[2-(tert-butyldimethylsilanyloxy)-1-methyl-4-pyridin-3-ylbutoxy]benzeneboronic acid (0.2 g, Example 11)), and tetrakis(triphenylphosphine)palladium (0) (0.02 g) with heating at 120° C. for 4 hours. After work-up, the residue was purified by normal-phase HPLC eluting a gradient of 0–25% ethanol in dichloromethane to give the title compound as a solid (0.116 g).

m.p. 75–76° C.

MS (APCI) 392 (M+H)+

1H NMR (DMSO) 8.58(1H, s); 8.43(2H, d); 7.64(2H, d); 7.48(2H, d); 7.32–7.23(3H, m); 7.1 1(1H, d); 6.98(2H, d); 5.87(2H, d); 5.00(1H, d); 3.56(1H, d); 3.49–3.34(1H, m); 2.87–2.76(1H, m); 2.71–2.60(1H, m); 1.92–1.82(1H, m); 1.72–1.63(1H, m); 1.24(3H, d).

EXAMPLE 32

(3R,4S)-4-(3',4'-Dichlorobiphenyl-4-yloxy)-1-pyridin-3-yl-pentan-3-ol oxalic acid salt

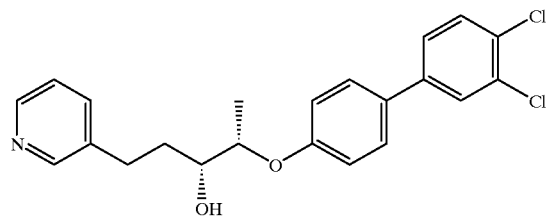

Prepared according to the method described in Example 12b) from 3,4-dichloro-iodobenzene (0.273 g), ethanol (2 ml), toluene (5 ml), 2M aqueous sodium carbonate (0.5 ml), (1S,2R)-4-[2-(tert-butyldimethylsilanyloxy)-1-methyl-4-pyridin-3-ylbutoxy]benzeneboronic acid (0.2 g, Example 11)), and tetrakis(triphenylphosphine)palladium (0) (0.025 g) with heating at 120° C. for 4 hours. After work-up, the residue was purified by normal-phase HPLC eluting a gradient of 0–25% ethanol in dichloromethane to give the title compound which was converted to the oxalic acid salt by treatment with a saturated ethereal solution of oxalic acid to give the title compound as a solid (0.229 g).

m.p. 86–88° C.

MS (APCI) 402, 404 (M+H)+

1H NMR (DMSO) 8.46(1H, d); 8.44 (1H, d); 7.87 (1H, d); 7.70 (1H, dt); 7.65–7.58 (4H, m); 7.35 (1H, dd); 7.0 (2H, d); 4.35 (1H, dq); 3.60–3.52 (1H, m); 2.88–2.78 (1H, m) 2.61 (1H, m); 1.95–1.82 (1H, m); 1.70–1.59 (1H, m); 1.25 (3H, d).

EXAMPLE 33

(1S,2R)-4-(2-Hydroxy-1-methyl-4-pyridin-3-ylbutoxy)benzeneboronic acid

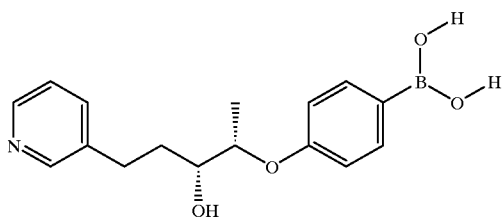

A solution of (1S,2R)-4-[2-(tert-butyldimethylsilanyloxy)-1-methyl-4-pyridin-3-ylbutoxy]benzeneboronic acid (10 g, Example 11) in methanol (150 ml) was stirred for 16 hours at room temperature and 2M hydrochloric acid (25 ml). The solution was concentrated to give an acidic aqueous residue which was washed with diethyl ether. The aqueous layer was basified with saturated sodium bicarbonate, the product was extracted into ethyl acetate, dried over anhydrous magnesium sulfate, filtered and concentrated to give the title compound as a foam. (6.97 g).

MS (APCI) 302 (M+H)$^+$ $^1$H NMR (DMSO/D$_2$O) 8.42(1H, s); 8.39(1H, s); 7.70–7.64(3H, m); 7.33(1H, dd); 6.85 (2H, d); 4.32(1H, m); 3.53(1H, m); 2.79(1H, m); 2.66(1H, m); 1.84(1H, m); 1.65 (1H, m); 1.21(3H, d).

EXAMPLE 34

(1S,2R)-4'-(2-Hydroxy-1-methyl-4-pyridin-3-yl-butoxy)-3-methyl-biphenyl-4-carbonitrile

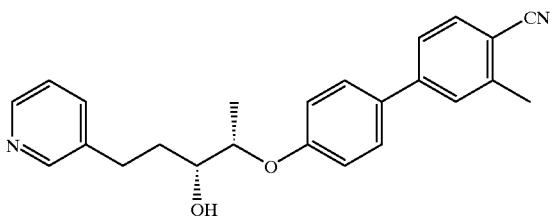

Prepared according to the method described in Example 12b) from (1S,2R)-4-(2-hydroxy-1-methyl-4-pyridin-3-ylbutoxy)benzeneboronic acid (0.150 g, Example 33), 4-bromo-2-methylbenzonitrile (0.301 g), 2M aqueous sodium carbonate (0.50 ml) and tetrakis (triphenylphosphine)palladium (0) (0.025 g) in ethanol (3 ml). The reaction mixture was heated at 90° C. for 4 hours. After cooling, the solution was concentrated under reduced pressure, taken up in ethanol and concentrated again (twice). The residue was triturated with acetone and then filtered through silica gel. The filtrate was concentrated under reduced pressure, dissolved in dichloromethane, filtered and purified by normal-phase HPLC eluting with a gradient of 0–25% ethanol in dichloromethane to give an oil which crystallised under high vacuum over 24 hours. Trituration with diethyl ether resulted in isolation of the title compound as a solid (0.11 g).

m.p. 93.5–94.5° C.

MS (APCI) 373.2 (M+H)$^+$ $^1$H NMR (DMSO) 8.44 (1H, m), 8.38 (1H, m), 7.79 (1H, d), 7.34 (1H, s), 7.68–7.60 (4H, m), 7.31 (1H, m), 7.02 (2H, d), 5.01 (1H, d), 4.36 (1H, m), 3.55 (1H, m), 2.80 (1H, m), 2.65 (1H, m), 2.53 (3H, s), 1.86 (1H, m), 1.64 (1H, m), 1.24 (3H, d).

EXAMPLE 35

(1S, 2R)-4-Fluoro-4'-(2-hydroxy-1-methyl-4-pyridin-3-yl-butoxy)biphenyl-3-sulfonic acid amide, and (1S, 2S)-4-Fluoro-4'-(2-hydroxy-1-methyl-4-pyridin-3-yl-butoxy)biphenyl-3-sulfonic acid amide

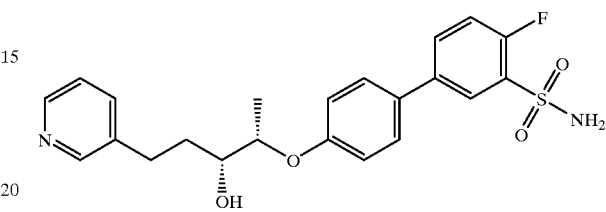

a) 5-Bromo-2-fluorophenylsulphonic acid amide

A mixture of 5-Bromo-2-fluoronitrobenzene (11 g), iron (20 g) and ammonium chloride (20 g) was refluxed in ethanol (200 ml) and water (150 ml) for 1 hour. The reaction was cooled, filtered and concentrated to (200 ml). The filtrate was extracted with ether, dried over anhydrous magnesium sulfate and concentrated. The residue was added to concentrated hydrochloric acid (20 ml) and cooled to −5° C. A saturated solution of sodium nitrite (3.88 g) in water (6 ml) was dropwise added at such a rate to maintain the temperature below 0° C. Magnesium chloride (8 g) was added (CARE:exotherm) and the resulting mixture added with stirring to a saturated solution of sulfur dioxide in acetic acid (40 ml) and toluene (20 ml), containing cupric chloride (2.75 g) at room temperature. The mixture was stirred for 60 minutes, poured into water and extracted into toluene. The combined toluene extracts were washed with water, dilute sodium hydrogen carbonate, dried over anhydrous magnesium sulfate and concentrated. The residue was dissolved in tetrahydrofuran (50 ml) and ammonia (0.880, 10 ml) was added. The resulting mixture was stirred for 30 minutes and concentrated to afford an aqueous residue that was partitioned between ethyl acetate (30 ml) and water (30 ml). The aqueous residue was extracted with ethyl acetate (3×30 ml) and the combined extracts dried over anhydrous magnesium sulfate and concentrated. The residue was triturated with 1:4 ether:hexane and filtered to afford the sub-title compound as a solid (6.37 g).

m.p. 153–154° C.

MS (APCI) 254 (M−H)$^−$ $^1$H NMR (CDCl$_3$) 8.05 (1H, dd); 7.71–7.66 (1H, m); 7.13 (1H, dd); 5.11 (2H, s).

b) (1S, 2R)-4-Fluoro-4'-(2-hydroxy-1-methyl-4-pyridin-3-y-butoxy)biphenyl-3-sulfonic acid amide, and (1S, 2S)-4-Fluoro-4'-(2-hydroxy-1-methyl-4-pyridin-3-yl-butoxy) biphenyl-3-sulfonic acid amide Prepared according to the method described in Example 12b) from 5-bromo-2-fluorophenylsulphonic acid amide (0.191 g, Example 34a)), ethanol (2 ml), toluene (5 ml), 2M aqueous sodium carbonate (0.5 ml), (1S,2R)-4-[2-(tert-butyldimethylsilanyloxy)-methyl-4-pyridin-3-ylbutoxy] benzeneboronic acid (0.2 g, Example 11)), and tetrakis (triphenylphosphine)palladium (0) (0.025 g) with heating at 80° C. for 2 hours. After work-up, the residue was purified by normal-phase HPLC eluting a gradient of 0–25% ethanol in dichloromethane to give the minor diastereomer (1S, 2S)-4-fluoro-4'-(2-hydroxy-1-methyl-4-pyridin-3-yl-butoxy)biphenyl-3-sulfonic acid amide as a foam, and with further elution the major product (1S, 2R)-4-fluoro-4'-(2-hydroxy-1-methyl-4-pyridin-3-yl-butoxy)biphenyl-3-sulfonic acid amide (0.15 g)

(1S, 2S)-4-Fluoro-4'-(2-hydroxy-1-methyl-4-pyridin-3-yl-butoxy)biphenyl-3-sulfonic acid amide
MS(APCI) 431 (M+H)+
$^1$H NMR(DMSO); 8.43(1H, d); 8.37(1H, dd); 7.94(1H, dd); 7.89–7.85(1H, m); 7.71(2H, s); 7.64–7.61(1H, m); 7.56(2H, d); 7.50–7.44(1H, m); 7.30–7.26(1H, m); 7.04(2H, d); 4.97(1H, d); 4.43–4.40(1H, m); 3.60–3.50(1H, m); 2.85–2.58(2H, m); 1.82–1.60(2H, m); 1.21(3H, d).

(1S, 2R)-4-Fluoro-4'-(2-hydroxy-1-methyl-4-pyridin-3-yl-butoxy)biphenyl-3-sulfonic acid amide
MS (APCI) 431 (M+H)+
$^1$H NMR (CDCl$_3$) 8.46 (1H, d); 8.43 (1H, d); 8.04 (1H, dd); 7.71–7.68 (1H, m); 7.54 (1H, dt); 7.55 (2H, d); 7.28–7.21 (2H, m); 6.95 (2H, d); 5.32 (2H, s); 4.40–4.30 (1H, m); 3.87–3.83 (1H, m); 2.98–2.93 (1H, m); 2.79–2.70 (1H, m); 2.34 (1H, br); 1.92–1.80 (2H, m); 1:31(3H, d).

EXAMPLE 36

(1S,2R)-4-Fluoro-4'-(2-hydroxy-1-methyl-4-pyridin-3-yl-butoxy)biphenyl-3-carbonitrile

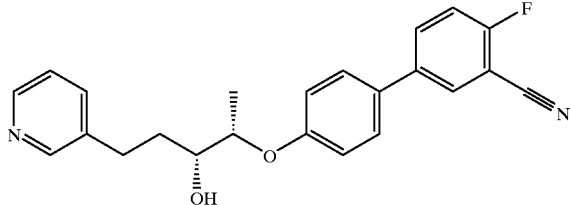

Prepared according to the method described in Example 12 from (1S,2R)-4-(2-hydroxy-1-methyl-4-pyridin-3-ylbutoxy)benzeneboronic acid (0.4 g, Example 33), 3-cyano-4-flurobromobenzene (0.399 g), ethanol (10 ml), 2M aqueous sodium carbonate (1.66 ml) and tetrakis(triphenylphosphine)palladium (0) (0.3 g) with heating at 80° C. for 3 hours. After work-up, the residue was purified by normal-phase HPLC eluting a gradient of 0–10% ethanol in dichloromethane to give the title compound as a solid. (0.24 g).

m.p. 108–109° C.

MS (APCI) 377 (M+H)+

$^1$H NMR (CDCl$_3$) 8.55 (1H, s); 8.45 (1H, d); 7.75–7.70 (2H, m); 7.60–7.50 (1H, m); 7.45–7.40 (2H, m); 7.25–7.20 (2H, m); 6.95 (2H, d); 4.45–4.35 (1H, m); 3.90–3.80 (1H, m); 3.00–2.90 (1H, m); 2.80–2.70 (1H, m); 2.15 (1H, d); 1.90–1.80 (2H, m); 1.30 (3H, d).

EXAMPLE 37

(1S, 2R)-2,5-Difluoro-4'-(2-hydroxy-1-methyl-4-pyridin-3-yl-butoxy)biphenyl-4-sulfonic acid amide

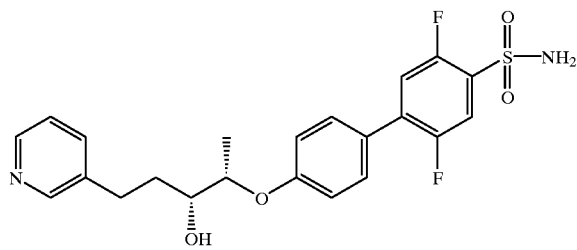

a) 4-Bromo-2,5-difluorobenzenesulfonamide
Ammonium hydroxide (5 ml) was added to a solution of 2,5-difluoro-4-bromophenylsulfonyl chloride (4.3 g) in tetrahydrofuran (20 ml) at room temperature (CARE:exotherm) and stirred for 10 min. The reaction mixture was poured into water and extracted with ethyl acetate. The ethyl acetate was dried over anhydrous magnesium sulfate and filtered. The filtrate was evaporated and the residue triturated with 20% diethyl ether in isohexane to give the sub-title compound as a solid (4.3 g).
m.p. 161–163° C.
MS (EI) 271/273 (M+)
$^1$H NMR (CDCl$_3$) 7.69(1H, t); 7.50(1H, dd); 5.17(2H, s);
b) (1S, 2R)-2,5-Difluoro-4'-(2-hydroxy-1-methyl-4-pyridin-3-yl-butoxy)biphenyl-4-sulfonic acid amide
Prepared according to the method described in Example 12) from (1S,2R)-4-(2-hydroxy-1-methyl-4-pyridin-3-ylbutoxy)benzeneboronic acid (0.2 g, Example 33), 4-bromo-2,5-difluorobenzenesulfonamide (0.19 g, Example 37a)), ethanol (3 ml), 2M aqueous sodium carbonate (0.7 ml) and tetrakis(triphenylphosphine)palladium (0) (0.03 g) with heating at 80° C. for 3 hours. After work-up, the residue was purified by normal-phase HPLC eluting with a gradient of 0–25% ethanol in dichloromethane to give the title compound as a foam (0.11 g).
MS (APCI) 449 (M+H)+
NMR (CDCl$_3$) 8.51(1H, d); 8.46(1H, d); 7.69(1H, dd); 7.54(1H, dd); 7.48(2H, dd); 7.31–7.02(2H, m); 6.97(2H, dd); 5.16(2H, s); 4.44–4.39(1H, m); 3.88–3.85(1H, m); 2.99–2.92(1H, m);2.80–2.74(1H, m); 2.12(1H, d); 1.92–1.80(2H, m); 1.32(3H, d).

EXAMPLE 38

(1S,2R)-3-Chloro-4'-(2-hydroxy-1-methyl-4-pyridin-3-ylbutoxy)biphenyl-4-carbonitrile

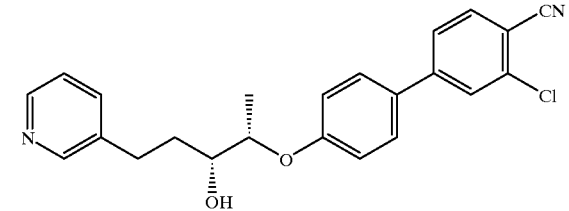

Prepared according to the method described in Example 12b) from (1S,2R)-4-(2-hydroxy-1-methyl-4-pyridin-3-ylbutoxy)benzeneboronic acid (0.20 g, Example 33), 4-bromo-2-chlorobenzonitrile (0.288 g), 2M aqueous sodium carbonate (0.76 ml) and tetrakis (triphenylphosphine)palladium (0) (0.075 g) in ethanol (5 ml) with heating at 90° C. for 4 hours. After work up, the residue was purified by normal-phase HPLC eluting with a gradient of 0–10% ethanol in dichloromethane to give the title compound as an oil (0.18 g).

MS(APCI) 393 (M+H)+

1H NMR (CDCl3) 8.51(1H, d); 8.46(1H, dd); 7.69–7.67 (2H, m);7.56–7.54(1H, m); 7.52(1H, m); 7.51(2H, d); 7.49–7.22(1H, m); 6.98(2H, d); 4.41–4.39(1H, m); 3.86–3.85(1H, m); 2.95–2.94(1H, m); 2.76–2.73(1H, m); 2.25–2.24(1H, m); 1.89–1.84(2H, m); 1.32(3H, d).

EXAMPLE 40

(1S,2R)-3-[6-(2-Hydroxy-1-methyl-4-pyridin-3-ylbutoxy)naphthalen-2-yl]-N,N-dimethylacrylamide

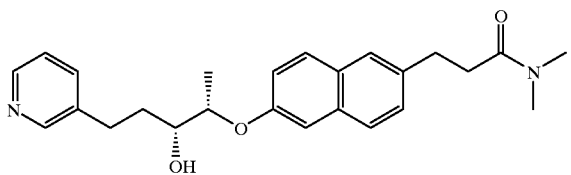

a) (1S,2R)-3-[6-(2-Hydroxy-1-methyl-4-pyridin-3-ylbutoxy)naphthalen-2-yl]-N,N-dimethylacrylamide (2S,3R)-4-(6-Bromonaphthalen-2-yloxy)-1-pyridin-3-yl-pentan-3-ol (0.25 g Example 10), N,N-dimethylacrylamide (0.64 g), tri-o-tolylphosphine (0.04 g), triethylamine (2ml) and palladium acetate (0.01 g) were added to acetonitrile (10 ml) and the mixture heated at 70° C. in a sealed tube for 16 hours. The reaction mixture was allowed to cool to room temperature and then concentrated under reduced pressure. The residue was purified by flash column chromatography over silica gel eluting with 20% acetone in isohexane followed by 50% acetone in isohexane and finally 5% methanol in dichloromethane, to afford the sub-title compound as an oil (0.27 g).

MS (APCI) 405 (M+H)+

NMR (CDCl3) 8.52(1H, s); 8.46(1H, d); 7.84(1H, s); 7.80(1H, d); 7.75(1H, s); 7.66(2H, d); 7.56(1H, d); 7.25–7.20(1H, m); 7.14(2H, d); 6.96(1H, d); 4.55–4.47(1H, m); 3.94–3.88(1H, m); 3.21(3H, s); 3.09(3H, s); 3.02–2.92 (1H, m); 2.80–2.70(1H, m); 1.93–1.85(2H, m); 1.36(3H, d).

b) (2S,3R)-3-[6-(3-Hydroxy)-5-pyridin-3-ylpent-2-yloxy)naphth-2-yl]propionic acid, dimethylamide A slurry of 10% palladium on carbon (0.1 g) in ethanol (20ml) was added to (2S,3R)-3-[6-(3-Hydroxy)-5-pyridin-3-ylpent-2-yloxy)naphth-2-yl]propenoic acid, dimethyl amide (0.27 g, Example 40a) in ethanol (30ml) and the mixture was hydrogenated at a pressure of 1.5 atmospheres for 2 hours. The reaction mixture was filtered through Celiteo to remove catalyst and the filter cake washed with ethanol (2×50 ml). The combined filtrate and washings were concentrated under reduced pressure and the residue purified by normal phase HPLC eluting with a gradient of 0–25% ethanol in dichloromethane to give the title compound as an oil (0.11 g).

MS (APCI) 407 (M+H)+

NMR (CDCl3) 8.52(1H, s); 8.46(1H, d); 7.69(1H, d); 7.63(1H, d); 7.59–7.55(2H, m); 7.33(1H, dd); 7.24–7.22 (1H, m); 7.11–7.09(2H, m); 4.52–4.45(1H, m); 3.97–3.90 (1H, m); 3.10(1H, t); 2.94(6H, m); 2.76–2.66(4H, m); 2.35–2.15(2H, m); 1.95–1.85(2H, d).

EXAMPLE 41

(1S, 2R)-4'-(2-Hydroxy-1-methyl-4-pyridin-3-ylbutoxy)biphenyl-3-N-sulfonamido-N'-isopropyl-urea

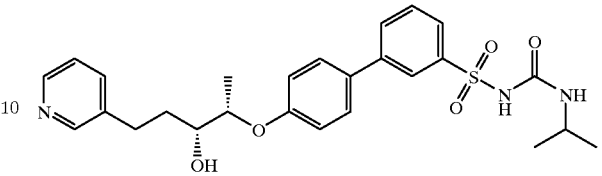

a) N-[(Methylamino)carbonyl],3-bromobenzenesulfonamide

Isopropylisocyanate (0.6 ml) was added to a solution of 3-bromobenzenesulphonamide (1.18 g) and copper (I) chloride (0.025 g) in anhydrousdimethylformamide (3 ml). The resulting solution was stirred for 20 hours and poured into 2N hydrochloric acid solution (50 ml) and the resulting precipitate filtered. The resulting solid was dissolved in dichloromethane (40 ml) and dried over anhydrous magnesium sulfate, filtered and concentrated. The residue was triturated with hexane and filtered to afford the sub-title compound as a solid (1.34 g).

m.p. 136.5–137° C.

MS (APCI) 321, 323 (M+H)+

1H NMR (CDCl3) 8.18 (1H, br); 8.04 (1H, t); 7.82 (1H, dt); 7.76 (1H, dt); 7.42 (1H, t); 6.38 (1H, d); 4.01–3.88 (1H, m); 1.18 (6H, d).

b) (1S, 2R)-4 '-(2-Hydroxy-1-methyl-4-pyridin-3-ylbutoxy)biphenyl-3-N-sulfonamido-N'-isopropyl-urea Prepared according to the method described in Example 4e) from (1S,2R)-4-[2-(tert-butyldimethylsilanyloxy)-1-methyl-4-pyridin-3-ylbutoxy],enzeneboronic acid (0.20 g, Example 11), N-[(methylamino)carbonyl],3-bromobenzenesulfonamide (0.28 g), 2M aqueous sodium carbonate (0.5 ml) and tetrakis(triphenylphosphine) palladium (0) (0.05 g) in toluene (5 ml) and ethanol (2 ml). The reaction was heated at 120° C. for 4 hours. After cooling 2M hydrochloric acid (10 ml) and methanol were added. The mixture was stirred for 30 minutes then extracted with ether (30 ml). The residual aqueous phase was adjusted to pH 7 and was extracted with ethyl acetate. The combined organic extracts were dried over anhydrous magnesium sulfate, filtered and concentrated under reduced pressure. The residue was dissolved in tetrahydrofuran (20 ml) and a solution of tetrabutylammonium fluoride in tetrahydrofuran (1M, 10 ml) added. The solution was stirred for 18 hours and then concentrated under reduced pressure. The residue was partitioned between pH 7 buffer and ethyl acetate. The combined organic extracts were dried over anhydrous magnesium sulfate, filtered and concentrated under reduced pressure. The residue was purified by lo normal-phase HPLC eluting with a gradient of 0–25% ethanol in dichloromethane to give a gum (0.07 g). This was triturated with isohexane:ether (9:1) to give a solid.

MS (APCI) 498 (M+H)+

1H NMR (DMSO) 8.45(1H, s); 8.39(1H, d); 8.07(1H, s); 7.87(1H, d); 7.79(1H, d); 7.7–7.5(4H, m); 7.35–7.25(1H, m); 7.05(2H, d); 6.33(1H, br s); 5.05–4.95(1H, m); 4.4–4.3 (1H, m); 3.7–3.5(2H, m); 2.9–2.55(3H, m); 1.95–1.8(1H, m); 1.8–1.55(1H, m); 1.25(3H, d); 0.98(6H, d).

EXAMPLE 42

(1S,2R)-3-[6-(2-Hydroxy-1-methyl-4-pyridin-3-yl-butoxy)-naphthalen-2-yl]-1-morpholin-4-yl-propan-1-one, oxalic acid salt

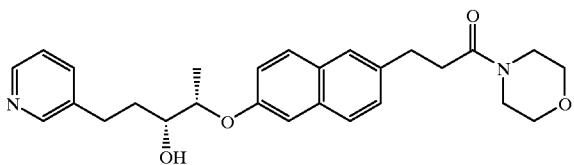

a) 1-Morpholin-4-yl-propenone

Acrylolyl chloride (8 g), morpholine (7.7 g) and triethylamine (8.94 g) were added to tetrahydrofuran (100 ml) at −30° C. The reaction mixture was stirred and slowly allowed to reach room temperature overnight. Precipitated triethylamine hydrochloride was removed by filtration and the filtrate was concentrated under reduced pressure. The residue thus obtained was stirred in a 1:1 mixture of isohexane:diethyl ether (500 ml) to precipitate more triethylamine hydrochloride. The salt was removed by filtration and the filtrate concentrated under reduced pressure to give the sub-title compound as an oil (11 g).

GC/MS 141 (M)+

NMR (CDCl$_3$) 6.55(1H, dd); 6.32(1H, dd); 5.72(1H, dd); 3.70(8H, br.s).

b) (1S,2R)-3-[6-(2-Hydroxy-1-methyl-4-pyridin-3-yl-butoxy)-naphthalen-2-yl]-1-morpholin-4-yl-propenone Prepared according to the method described in Example 40a) from (2S, 3R)-4-(6-bromonaphthalen-2-yloxy)-1-pyridin-3-yl-pentan-3-ol ( 0.60 g Example 10), 1-morpholin-4-yl-propenone (1.09 g, Example 42a)), palladium acetate (0.03 g), tri-o-tolylphosphine (0.09 g) and triethylamine (2 ml) in acetonitrile (10 ml). After work up crude material was purified by flash column chromatography over silica eluting with 20% acetone in isohexane followed by 50% acetone in isohexane and finally 5% methanol in dichloromethane to give the sub-title compound as a foam (0.52 g).

MS (APCI) 447 (M+H)+

NMR (CDCl$_3$) 8.52(1H, d); 8.46(1H, dd); 7.85(1H, d); 7.79(1H, d); 7.72(1H, d); 7.66(1H, s); 7.64(1H, dd); 7.56 (1H, dd); 7.26–7.20(1H, m); 7.15(1H, dd); 7.12(1H, dd); 6.91(1H, d); 4.53–4.49(1H, m); 3.91(1H, br.s); 3.74(8H, br.s); 2.99–2.92(1H, m); 2.80–2.73(1H, m); 2.30(1H, br.s); 1.93–1.85(2H, m); 1.36(3H, d).

c) (1S,2R)-3-[6-(2-Hydroxy-1-methyl-4-pyridin-3-yl-butoxy)-naphthalen-2-yl]-1-morpholin-4-yl-propan-1-one, oxalic acid salt Prepared according to the method described in Example 40b) from (1S,2R)-3-[6-(2-Hydroxy-1-methyl-4-pyridin-3-yl-butoxy)-naphthalen-2-yl]-1-morpholin-4-yl-propenone (0.52 g, Example 42b)), 10% palladium on carbon (0.2 g) and ethanol (50 ml). After work up, crude material was purified by flash column chromatography over silica eluting with 5% ethanol in dichloromethane to give an oil (0.5 g). A portion (0.15 g) of this was treated with ethereal oxalic acid to give the title compound as a solid (0.14 g).

m.p. 156–159° C.

MS (APCI) 449 (M+H)+

NMR (DMSO) 8.47(1H, d); 8.41(1H, dd); 7.72–7.67(3H, m); 7.62(1H, s); 7.36–7.32(2H, m); 7.24(1H, d); 7.11(1H, dd); 4.45–4.39(1H, m); 3.62–3.56(1H, m); 3.50–3.37(8H, m); 2.93(2H, t); 2.83–2.79(1H, m); 2.73–2.69(3H, m); 1.92–1.88(1H, m); 1.71–1.66(1H, m); 1.28(3H, d).

EXAMPLE 43

(3R,4S)-4-[6-(3-Morpholin-4-yl-propyl)naphthalen-2-yloxy]-1-pyridin-3-yl-pentan -3ol, oxalic acid salt

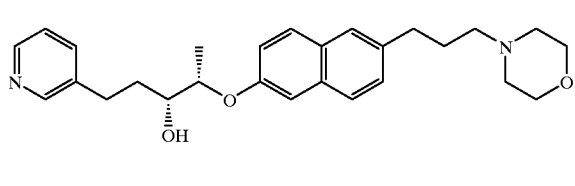

Diborane (10 ml, 1.0M solution in tetrahydrofuran) was cooled to 0° C. and stirred under a nitrogen atmosphere. (1S,2R)-3-[6-(2-Hydroxy-1-methyl-4-pyridin-3-yl-butoxy)-naphthalen-2-yl]-1-morpholin-4-yl-propan-1-one, oxalic acid salt (0.35 g, Example 42c)) in tetrahydrofuran (10 ml) was added to this, dropwise, over a period of 15 minutes. The resultant colourless solution was brought up to reflux temperature and heated under reflux for 1 hour. The reaction was allowed to cool to room temperature and acidified with 6M hydrochloric acid (2 ml) then heated at reflux temperature for 0.5 hour. The solution was cooled and partitioned between ether and water. The aqueous layer was made basic with 2M sodium hydroxide and extracted with ethyl acetate. The ethyl acetate was washed with brine and dried over anhydrous magnesium sulfate. After filtration, solvent was removed by evaporation under reduced pressure and the residue purified by flash column chromatography over silica eluting with dichloromethane containing 2% triethylamine and 1% ethanol to give the free base of the title compound as an oil (0.25 g). This was treated with ethereal oxalic acid to give the title compound as a solid (0.15 g).

MS (APCI) 435 (M+H)+

NMR (DMSO) 8.44(1H, d); 8.38(1H, dd); 7.73(2H, dd); 7.64(2H, dd); 7.35–7.26(3H, m); 7.12(1H, dd); 4.43–4.39 (1H, m); 3.78(4H, br.s); 3.60–3.58(1H, m); 3.42–3.35(2H, m); 3.13(4H, br.s); 3.02(1H, t); 2.82–2.66(3H, m); 2.09–1.95(2H, m); 1.95–1.82(1H, m); 1.76–1.62(1H, m); 1.28(3H, d).

EXAMPLE 44

(3R,4S)-4-[6-(3-Methylaminopropyl)naphthalen-2-yloxy]-1-pyridin-3-yl-pentan-3-ol, oxalic acid salt

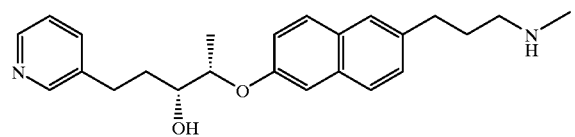

Prepared according to the method described in Example 43 from (1S,2R)-3-[6-(2-hydroxy-1-methyl-4-pyridin-3-yl-butoxy)naphthalen-2-yl]-N-methylpropionamide (0.12 g, Example 85c)) and diborane (10 ml, 1.0M solution in tetrahydrofuran) in tetrahydrofuran (30 ml). After work up solvent was removed by evaporation under reduced pressure and the residue treated with ethereal oxalic acid to give the title compound as a hygroscopic solid (0.017 g).

MS (APCI) 379 (M+H)+

NMR (DMSO) 8.67(1H, br.s); 8.44(1H, d); 8.38(1H, dd); 7.73(2H, dd); 7.63(2H, m); 7.33–7.26(3H, m); 7.12(1H, dd); 4.43–4.40(1H, m); 3.62–3.57(1H, m); 2.95–2.60(6H, m); 2.54(3H, s); 2.00–1.85(3H,m); 1.72–1.63(1H, m); 1.28(3H, d).

EXAMPLE 45

(1S,2R)-4'-(2-Hydroxy-1-isopropyl-4-pyridin-3-yl-butoxy)biphenyl-3-carbonitrile

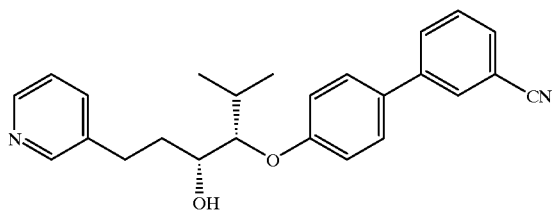

Prepared according to the method described in Example 12b) from 3-cyanobenzeneboronic acid (0.40 g), (3S,4R)-3-(4-bromophenyloxy)-2-methyl-6-(3-pyridyl)hexan-4-ol (0.90 g, Example 61d)), 2M aqueous sodium carbonate (2.72 ml) and tetrakis(triphenylphosphine)palladium(0) (0.160 g) in ethanol (4 ml). The reaction mixture was heated at 90° C. for 4 hours. After cooling, the solution was poured onto water, and extracted with ethyl acetate. The combined extracts were washed with brine, dried over magnesium sulfate, and filtered. The filtrate was concentrated under reduced pressure, dissolved in dichloromethane, filtered and purified by normal-phase HPLC eluting with a gradient of 0–25% ethanol in dichloromethane to give the title compound as a gum (0.54 g).

MS (APCI) 387(M+H)$^+$ $^1$H NMR (DMSO) 8.35(2H, s); 8.07(1H, s); 7.95(1H, d); 7.75(1H, d); 7.69–7.5(4H, m); 7.25(1H, t); 7.1(2H, d); 5.0(1H, d); 4.2–4.12(1H, m); 3.7–3.6(1H, m); 2.85–2.72 (1H, m); 2.7–2.65(1H, m); 2.2–2.05(1H; m); 1.85–1.55(2H, m); 0.9(6H, dd).

EXAMPLE 46

Comparative (3R,4S)-1-Pyridin-3-yl-4-[4'-(2-pyrrolidin-1-yl-ethoxy)biphenyl-4-yloxy]pentan-3-ol

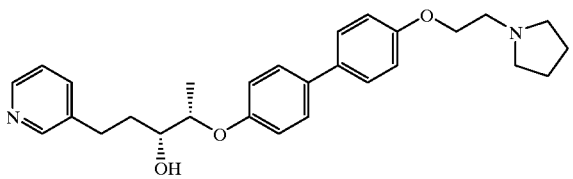

Prepared according to the method described in Example 12b) from (1S,2R)-4-(2-hydroxy-1-methyl-4-pyridin-3-ylbutoxy)benzeneboronic acid (0.190 g, Example 33), 1-[2-(4-bromophenoxy)ethyl]pyrrolidine (0.27 g), 2M aqueous sodium carbonate (0.75 ml) and tetrakis (triphenylphosphine)palladium (0) (0.025 g) in ethanol (2 ml). The reaction mixture was heated at 90° C. for 4 hours. After cooling, the solution was concentrated under reduced pressure, taken up in ethanol and concentrated again (twice). The residue was triturated with acetone and then filtered through silica gel. The filtrate was concentrated under reduced pressure, dissolved in dichloromethane, filtered and purified by normal-phase HPLC eluting with a gradient of 0–25% ethanol in dichloromethane to give an oil which crystallised under high vacuum over 24 hours. Trituration with diethyl ether resulted in isolation of the title compound as a foam (0.194 g).

MS (APCI) 447.2 (M+H)$^+$ $^1$H NMR (CDCl$_3$) 8.51 (1H, d); 8.46 (1H, dd); 7.55 (1H, dt); 7.46 (4H, d); 7.22 (1H, dd); 6.98 (2H, d); 6.92 (2H, d); 4.37 (1H, dt); 4.15 (2H, t); 3.88–3.85 (1H, m); 2.83 (3H, t); 2.78–2.67 (1H, m); 2.73–2.63 (4H, m); 2.2 (1H, br); 1.89–1.80 (6H, m); 1.30 (3H, d).

EXAMPLE 47

Comparative (1S,2R)-4'-(2-Hydroxy-1-methyl-4-pyridin-3-ylbutoxy)-4-(2-morpholin-4-yl-ethoxy)biphenyl-3-carbonitrile

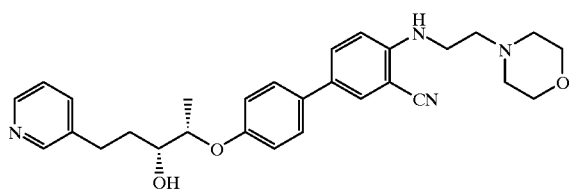

a) 5-Bromo-2-(2-morpholin-4-yl-ethylamino)benzonitrile

5-Bromo-2-fluorobenzonitrile (1.0 g) and 4-(2-aminoethyl)morpholine (0.65 g) were mixed together in acetonitrile (5 ml) at 70° C. for 4 hours, cooled and poured into a solution of aqueous sodium hydrogen carbonate and was extracted into ethyl acetate, dried over anhydrous magnesium sulfate and concentrated. The residue was purified by chromatography on silica gel eluting with 2.5% methanol in dichloromethane containing 1% triethylamine to afford the sub-titled compound as an oil (0.77 g).

MS (APCI) 310, 312 (M+H)$^+$ b) (1S ,2R)-4'-(2-Hydroxy-1-methyl-4-pyridin-3-ylbutoxy)-4-(2-morpholin-4-yl-ethoxy)biphenyl-3-carbonitrile Prepared according to the method described in Example 12b) from (1S,2R)-4-(2-hydroxy-1-methyl-4-pyridin-3-ylbutoxy)benzeneboronic acid (0.190 g, Example 33), 5-bromo-2-(2 -morpholin-4-yl-ethylamino)benzonitrile (0.31 g, Example 47a)), 2M aqueous sodium carbonate (0.75 ml) and tetrakis(triphenylphosphine)palladium (0) (0.025 g) in ethanol (2 ml). The reaction mixture was heated at 90° C. for 4 hours. After cooling, the solution was concentrated under reduced pressure, taken up in ethanol and concentrated again (twice). The residue was triturated with acetone and then filtered through silica gel. The filtrate was concentrated under reduced pressure, dissolved in dichloromethane, filtered and purified by normal-phase HPLC eluting with a gradient of 0–25% ethanol in dichloromethane to give an oil which crystallised under high vacuum over 24 hours. Trituration with diethyl ether resulted in isolation of the title compound as a foam (0.19 g).

MS (APCI) 487.2 (M+H)$^+$ $^1$H NMR (CDCl$_3$) 8.50 (1H, d); 8.45 (1H, dd); 7.60–7.54 (3H, m); 7.40 (2H, dd); 7.24–7.22 (1H, dd); 6.93 (2H, dd); 6.70 (1H, d), 5.40 (1H, t); 4.38–4.35 (1H, m); 3.87–3.83 (1H, m); 3.76 (4H, dd); 3.27 (2H, q); 2.95–2.90 (1H, m); 2.80–2.75 (1H, m); 2.70 (2H, t); 2.54–2.49 (4H, m); 2.20 (1H, d); 1.89–1.80 (2H, m); 1.30 (3H, d).

EXAMPLE 48

(3R,4S)-4-(3'-Methanesulfonylbiphenyl-4-yloxy)-1-pyridin-3-yl-pentan-3-ol

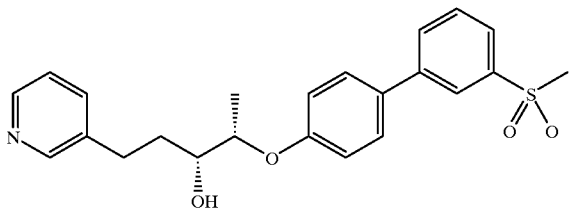

a) 1-Bromo-3-methanesulfonylbenzene

3-Bromothioanisole was dissolved in methanol (20 ml) and cooled to 0° C. (ice/water bath). A solution of Oxone® (9.22 g) in water (30 ml) was added to this and the resultant cloudy slurry was stirred at room temperature for 3 hours. The reaction mixture was diluted with water and product extracted with dichloromethane. The combined fractions of dichloromethane were washed with brine and dried over anhydrous magnesium sulfate. After filtration, solvent was removed by evaporation under reduced pressure to give the sub-title compound as a solid (1.02 g).

m.p. 63–64° C.

GClMS 236/238 (M)$^+$ $^1$H NMR (CDCl$_3$) 8.10(1H, s); 7.89(1H, dd); 7.80(1H, dd); 7.47(1H, t); 3.08(3H, s).

b) (2S,3R)-2-[4-(3'-Methylsulfonyl)biphenyloxy]-5-(pyridin-3-yl)pentan-3-ol

Prepared according to the method described in Example 12b) from (1S,2R)-4-[2-(tert-butyldimethylsilanyloxy)-1-methyl-4-pyridin-3-ylbutoxy]benzeneboronic acid (0.2 g, Example 11), 1-bromo-3-methanesulfonylbenzene (0.23 g, Example 48a)), ethanol (2 ml), toluene (5 ml), 2M aqueous sodium carbonate (0.5 ml) and tetrakis(triphenylphosphine)palladium (0) (0.03 g) with heating at reflux temperature 4 hours. After cooling, the solution was concentrated under reduced pressure. Concentrated hydrochloric acid (1 ml) was added to a solution of the residue in methanol (5 ml) and the suspension was stirred at room temperature for 1 hour. After work-up, the residue was purified by normal-phase HPLC eluting with a gradient of 0–25% ethanol in dichloromethane to give the title compound as an oil (0.17 g).

MS (APCI) 412 (M+H)$^+$ $^1$H NMR (CDCl$_3$) 8.52(1H, br.s); 8.47(1H, br.s); 8.11(1H, t); 7.89–7.80(2H, m); 7.63(1H, d); 7.59–7.52(3H, m); 7.26–7,21(1H, m); 6.98( 2H, dd); 4.43–4.39(1H, m); 3.92–3.83(1H, m); 3.09(3H, s); 2.96(1H, m); 2.77–2.70(1H, m); 2.25(1H, br.s); 1.90–1.82(2H, m); 1.32(3H, d).

EXAMPLE 49

(1S,2R)-4'-(2Hydroxy-1-methyl-4-pyridin-3-yl-butoxy)biphenyl-3-carboxylic acid amide

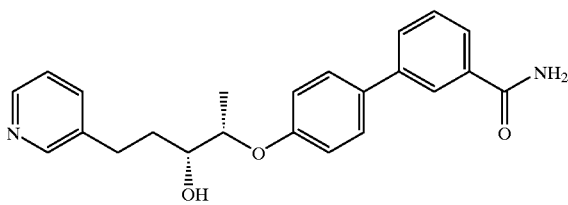

Prepared according to the method described in Example 12b) from (1S,2R)-4-(2-hydroxy-1-methyl-4-pyridin-3-ylbutoxy)benzeneboronic acid (0.150 g, Example 33), 3-bromo-2-benzamide (0.20 g), 2M aqueous sodium carbonate (0.50 ml) and tetrakis(triphenylphosphine)palladium (0) (0.020 g) in ethanol (3 ml) with heating at 90° C. for 2 hours. After work up, the residue was purified by normal-phase HPLC eluting with a gradient of 0–25% ethanol in dichloromethane to give the title compound as a solid (0.107 g).

m.p. 74–76° C.

MS(APCI) 377 (M+H)$^+$ $^1$H NMR (DMSO) 8.45(1H, s); 8.40(1H, d); 8.11(2H, s); 7.80(1H, d); 7.75(1H, d); 7.64(3H, d); 7.50(1H, t); 7.42(1H, s); 7.30(1H, t); 7.02(2H, d); 5.31(1H, d); 5.02(1H, t); 3.57(1H, bs); 2.85–2.79(1H, m); 2.70–2.62(1H, m); 1.89–1.85(1H, m); 1.70–1.65(1H, m); 1.25(3H, d).

EXAMPLE 50

(1S,2R)-2-[4'-(2-Hydroxy-1-methyl-4-pyridin-3-yl-butoxy)-biphenyl-3-yloxy]-acetamide

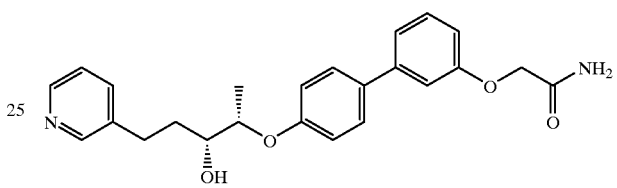

a) 2-(3-Bromophenoxy)-acetamide

A mixture of 2-chloroacetamide (5.6 g), 3-bromophenol (10 g), potassium carbonate (8.3 g) and potassium iodide (1 g) in acetonitrile was stirred at room temperature for 72 hours. The resulting mixture was filtered, and the solids washed with ethyl acetate, and then water. The dried solids were recrystallised from boiling ethanol: water(8:2) to give the sub-title compound as a solid (13.8 g).

m.p. 96–98° C.

MS (APCI) 228(M–H)$^+$ $^1$H NMR (DMSO) 7.55(1H, br,s); 7.4(1H, br,s); 7.25(1H, t); 7.13–7.18(2H, m); 6.96(1H, dd); 4.45(2H, s).

b) (2S,3R)-3-{4-[3-hydroxy-5-(3-pyridyl)pentan-2-yloxy]phenyl}phenyloxyacetic acid, amide Prepared according to the method described in Example 12b) from (1S,2R)-4-(2-hydroxy-1-methyl-4-pyridin-3-ylbutoxy)benzeneboronic acid (0.150 g, Example 33), 2-(3-bromophenoxy)acetamide (0.230 g), 2M aqueous sodium carbonate (0.50 ml) and tetrakis(triphenylphosphine) palladium(0) (0.025 g) in ethanol (3 ml). The reaction mixture was heated at 90° C. for 4 hours. After cooling, the solution was concentrated under reduced pressure, taken up in ethanol and concentrated again (twice). The residue was triturated with acetone and then filtered through silica gel. The filtrate was concentrated under reduced pressure, dissolved in dichloromethane, filtered and purified by normal-phase HPLC eluting with a gradient of 0–25% ethanol in dichloromethane to give a colourless solid, which was recrystallised from boiling ethyl acetate:isohexane (1:1) to give the title compound as a solid (0.138 g).

m.p. 120–122° C.

MS (APCI) 407 (M+H)$^+$ $^1$H NMR (DMSO) 8.15(1H, s); 8.46(1H, d); 7.56(1H, d); 7.49(2H, d); 7.37(1H, t); 7.3–7.19(2H, m); 7.1(1H, s); 6.95(2H, d); 6.86(1H, dd); 6.58(1H, br,s); 5.69(1H, br,s); 4.56(2H, s); 4.45–4.35(1H, m); 3.9–3.85(1H, m); 3.0–2.9 (1H, m); 2.8–2.7(1H, m); 2.26(1H, br,s); 1.9–1.8(2H, m); 1.31(3H, d).

EXAMPLE 51

(2S,3R)-1-Pyridin-3-yl-4-(2'-trifluoromethoxybiphenyl-4-yloxy)pentan-3-ol

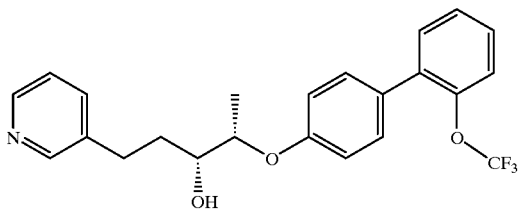

Prepared according to the method described in Example 12b) from (1S,2R)-4-(2-hydroxy-1-methyl-4-pyridin-3-ylbutoxy)benzeneboronic acid (0.150 g, Example 33), 2-bromo(trifluoromethyloxy)benzene (0.26 g), 2M aqueous sodium carbonate (0.50 ml) and tetrakis (triphenylphosphine)palladium (0) (0.025 g) in ethanol (3 ml). The reaction mixture was heated in a sealed vial at 80° C. for 2 hours. After cooling, the solution was is concentrated under reduced pressure and taken up in acetone and filtered through a small plug of silica. The filtrate was concentrated under reduced pressure, dissolved in dichloromethane, filtered and purified by normal-phase HPLC eluting with a gradient of 0–25% ethanol in dichloromethane to give an oil (0.145 g).

MS (APCI) 418 (M+H)$^+$ $^1$H NMR (CDCl$_3$) 8.52 (1H, d); 8.46(1H, dd); 7.56(1H, dd); 7.43–7.30(6H, m); 7.25–7.20(1H, m); 6.93(2H, d); 4.45–4.35(1H, m); 3.93–3.85(1H, m); 3.0–2.9(1H, m); 2.8–2.7(1H, m); 2.20(1H, br.s); 1.95–1.8(2H, m); 1.32(3H, d).

EXAMPLE 52

(1S,2R)-4'-(2-Hydroxy-1-methyl-4-pyridin-3-yl-butoxy)-6-methoxybiphenyl-3-carbonitrile

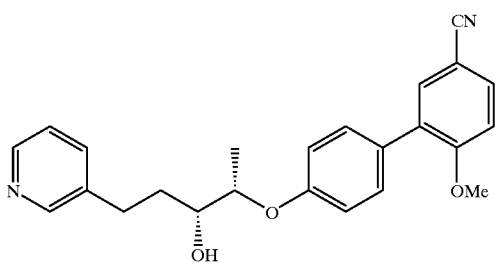

Prepared according to the method described in Example 12b) from (1S,2R)-4-(2-hydroxy-1-methyl-4-pyridin-3-ylbutoxy)benzeneboronic acid (0.20 g, Example 33), 3-bromo-4-methoxybenzonitrile (0.20 g), 2M aqueous sodium carbonate (0.5 ml) and tetrakis(triphenylphosphine) palladium (0) (0.03 g) in toluene (5 ml) and ethanol (2 ml), with heating at 90° C. for 4 hours. After work up, the residue was purified by normal-phase HPLC eluting with a gradient of 0–10% ethanol in dichloromethane to give the title compound as an oil (0.17 g).

MS(APCI) 389/390 (M+H)$^+$ $^1$HNMR(CDCl$_3$); 8.52(1H, s); 8.46(1H, d); 7.60(1H, d); 7.56(2H, m); 7.40(2H, d); 7.23(1H, dd); 7.00(1H, d); 6.93 (2H, d); 4.39(1H, m); 3.87(4H, m); 2.95(1H, m); 2.74(1H, m); 2.29(1H, br.s); 1.86(2H, m); 1.32(3H, d).

EXAMPLE 53

(3R,4S)-4-(4'-Chloro-2'-methoxy-5'-methylbiphenyl-4-yloxy)-1-pyridin-3-yl-pentan-3-ol

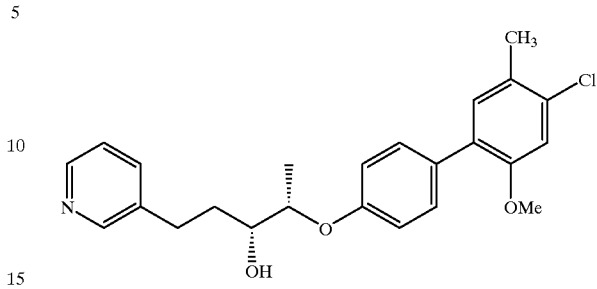

Prepared according to the method described in Example 12b) from (1S,2R)-4-(2-hydroxy-1-methyl-4-pyridin-3-ylbutoxy)benzeneboronic acid (0.15 g, Example 33), 5-bromo-2-chloro-4-methoxytoluene (0.12 g), 2M aqueous sodium carbonate (0.57 ml) and tetrakis (triphenylphosphine)palladium (0) (0.014 g) in ethanol (5 ml) with heating at 90° C. for 4 hours. After work up, the residue was purified by normal-phase HPLC eluting with a gradient of 0–10% ethanol in dichloromethane to give the title compound as an oil (0.13 g).

MS(APCI) 412 (M+H)$^+$ $^1$H NMR(CDCl$_3$) 8.51(1H, d); 8.45(1H, dd); 7.57–7.54 (1H, m); 7.46(2H, d); 7.24–7.21(1H, m); 7.12(1H, s); 6.95 (1H, s); 6.90(2H, d); 4.38–4.36(1H, m); 3.87–3.85(1H, m); 3.78(3H, s); 2.98–2.91(1H, m); 2.77–2.69(1H, m); 2.33(3H, s); 2.19(1H, d); 1.87–1.81(2H, m); 1.31(3H, d).

EXAMPLE 54

(1S,2R)-4'-(2-Hydroxy-1-methyl-4-pyridin-3-yl-butoxy)-biphenyl-3-carboxylic acid methylamide

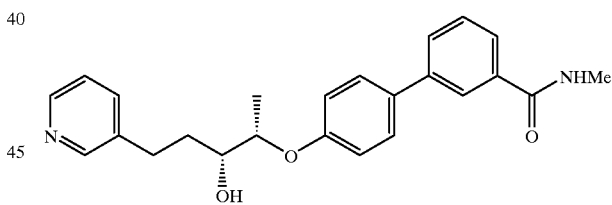

Prepared according to the method described in Example 12b) from (1S,2R)-4-(2-hydroxy-1-methyl-4-pyridin-3-ylbutoxy)benzeneboronic acid (0.150 g, Example 33), 3-bromo-N-methylbenzamnide (*J. of Org. Chem.;* 1963, 28, 3147–3149) (0.214 g), 2M aqueous sodium carbonate (0.25 ml) and tetrakis(triphenylphosphine)palladium (0) (0.05 g) in ethanol (3 ml). The reaction mixture was heated at 80° C. for 3 hours. After cooling, the solution was concentrated under reduced pressure. The residue was triturated with acetone and then filtered through silica gel. The filtrate was concentrated under reduced pressure, dissolved in dichloromethane, filtered and purified by normal-phase HPLC eluting with a gradient of 0–10% ethanol in dichloromethane. The product was further purified by flash column chromatography eluting with ethyl acetate to give the title compound as a solid (0.12 g).

m.p. 54–55° C.

MS (APCI) 391 (M+H)$^+$

¹H NMR (CDCl₃) 8.50(1H, d); 8.45 (1H, dd); 7.96–7.95 (1H, m); 7.65 (2H, dd); 7.57–7.51 (3H, m); 7.46 (1H, t); 7.24–7.21 (1H, m); 6.95 (2H, dd); 6.26(1H, bs); 4.40–4.38 (1H, m); 3.88–3.85 (1H, m); 3.05(3H, d); 2.95–2.92(1H, m); 2.78–2.72(1H, m); 2.32 (1H, d); 1.89–1.83(2H, m); 1.32 (3H, d).

EXAMPLE 55

(1S,2R)-[4'-(2-Hydroxy-1-methyl-4-pyridin-3-yl-butoxy)-biphenyl-4-yl]acetic acid

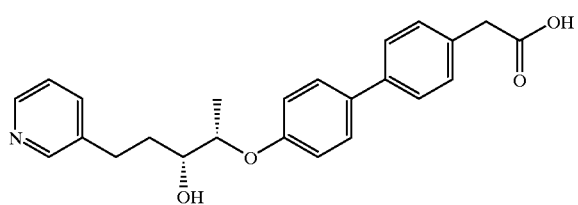

Prepared according to the method described in Example 12b) from (1S,2R)-4-(2-hydroxy-1-methyl-4-pyridin-3-ylbutoxy)benzeneboronic acid (0.6 g, Example 33), 4-bromophenylacetic acid (0.624 g), 2M aqueous sodium carbonate (2.5 ml) and tetrakis(triphenylphosphine) palladium (0) (0.5 g) in ethanol (15 ml). The reaction mixture was heated at 100° C. for 3 hours. After cooling, the solution was concentrated under reduced pressure. Water was added to the residue then washed with diethyl ether. The aqueous layer was acidified with 2M hydrochloric acid and washed with diethyl ether. The aqueous layer was neutralised to pH 7.11 and the solid filtered off washing with diethyl ether to give the title compound as a solid (0.431 g).

m.p. 196–197° C.

MS (APCI) 392 (M+H)⁺

¹H NMR (DMSO) 8.45(1H, d); 8.40 (1H, d); 7.63(1H, dt); 7.55–7.52(4H, m); 7.31–7.28(3H, m); 6.99 (2H, dd); 5.0(1H, bs); 4.33–4.30 (1H, m); 3.58–3.37 (3H, m); 2.80–2.77(1H, m); 2.67–2.63(1H, m); 1.88–1.85(1H, m); 1.66–1.62(1H, m); 1.24(3H, d).

EXAMPLE 56

(1S,2R)-N-[4'-(2-Hydroxy-1-methyl-4-pyridin-3-yl-butoxy)-5-trifluoromethyl-biphenyl-2-yl]acetamide

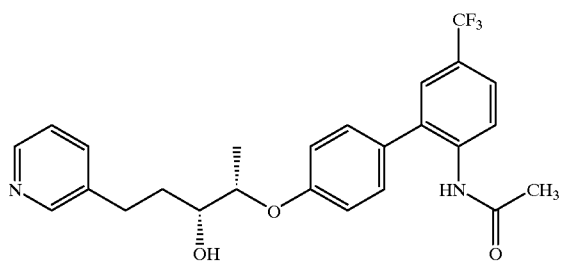

Prepared according to the method described in Example 12b) from (1S,2R)-4-(2-hydroxy-1-methyl-4-pyridin-3-ylbutoxy)benzeneboronic acid (0.15 g, Example 33), 2-bromo-4-(trifluoromethyl)acetanilide (0.28 g), 2M aqueous sodium carbonate (0.57 ml) and tetrakis (triphenylphosphine)palladium (0) (0.014 g) in ethanol (5 ml) with heating at reflux for 2 hours. After work up, the residue was purified by normal-phase HPLC eluting with a gradient of 0–5% ethanol in dichloromethane to give the title compound as a solid (0.16 g).

m.p.44–47° C.

MS(APCI) 459(M+H)⁺

¹H NMR(CDCl₃) 8.47(1H, d); 8.44(1H, dd); 7.60–7.56 (2H, m); 7.45–7.41(2H, m); 7.29–7.21(3H, m); 6.99(2H, d); 4.40–4.39(1H, m); 3.90–3.86(1H, m); 2.98–2.81(1H, m); 2.78–2.71(1H, m); 2.64(1H, br.s); 2.06(3H, s); 1.89–1.87 (3H, m); 1.35(3H, d).

EXAMPLE 57

(1S,2R)-2-[4'-(2-Hydroxy-1-methyl-4-pyridin-3-yl-butoxy)-biphenyl-2-yl]-N-methylacetamide

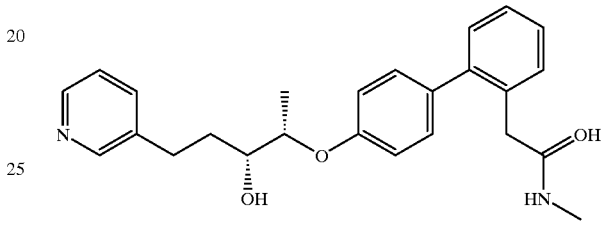

a) 2-(2-Bromo-phenyl)-N-methylacetamide

To a solution of 2-bromophenyl acetic acid (2.15 g) in dichloromethane (100 ml) was added methylamine (2M solution in tetrahydrofuran, 6 ml), 4-dimethylaminopyridine (1.32 g) and 1-(3-dimethylaminopropyl)-3-ethylcarbodiimide hydrochloride (2.055 g). The mixture was left to stir at room temperature for 16 hours, after which the organic portion was washed with 2M aqueous hydrogen chloride, dried over magnesium sulfate and filtered. The filtrate was concentrated to give a solid (2.04 g)

MS (APCI) 228/230 (M+H)⁺

¹H NMR (CDCl₃) 7.60(1H, d); 7.33(2H, m); 7.17(1H, t); 5.40(1H, s); 3.72(2H, s); 2.79(3H, d).

b) (2S,3R)-5-(3-pyridyl)-2-[4-(2(2-N-methylethanamide) phenyl)henoxy]pentan-3-ol Prepared according to the method described in Example 12b) from (1S,2R)-4-(2-hydroxy-1-methyl-4-pyridin-3-ylbutoxy)benzeneboronic acid (0.150 g, Example 33), 2-(2-bromophenyl)-N-methylacetamide (0.228 g), 2M aqueous sodium carbonate (0.5 ml) and tetrakis(triphenylphosphine) palladium(0) (0.025 g) were dissolved in ethanol (3 ml) and heated at 90° C. for 90 minutes. After cooling, the solution was concentrated and azeotroped with ethanol twice more. The residue was triturated with acetone and filtered through silica gel. The filtrate was concentrated, dissolved in dichloromethane and purified by normal-phase HPLC, eluting with a gradient of 0–25% ethanol in dichloromethane to give a solid (0.055 g).

m.p. 85–86° C.

MS (APCI) 405 (M+H)⁺

¹HNMR (CDCl₃) 8.45(2H, d); 7.58(1H, d); 7.34–7.15 (7H, m); 6.92(2H, d); 5.37(1H, s); 4.35 (1H, t); 3.84(1H, t); 3.54(2H, s); 2.93(1H, m); 2.76(4H, m); 1.87(3H, m); 1.33 (3H, d).

EXAMPLE 58

(1S,2R)-N-[4'-(2-Hydroxy-1-methyl-4-pyridin-3-yl-butoxy)-2-methylbiphenyl-4-yl]acetamide

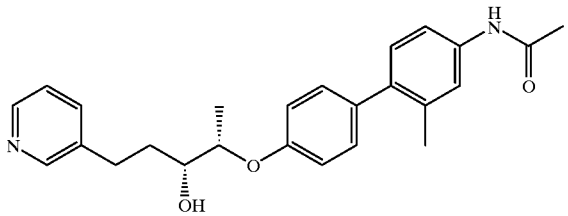

Prepared according to the method described in Example 12b) from (1S,2R)-4-(2-hydroxy-1-methyl-4-pyridin-3-ylbutoxy)benzeneboronic acid (0.150 g, Example 33), 4-bromo-3-methylacetanilide (0.228 g), 2M aqueous sodium carbonate (0.50 ml) and tetrakis(triphenylphosphine)palladium (0) (0.020 g) in ethanol (3 ml) with heating at 90° C. for 2 hours. After work up, the residue was purified by normal-phase HPLC eluting with a gradient of 0–25% ethanol in dichloromethane, then by reverse-phase HPLC eluting a gradient of 25–100% acetonitrile in 0.1 w/v aqueous ammonium acetate solution to give the title compound as an oil (0.041 g).

MS(APCI) 405 (M+H)$^+$ $^1$H NMR (DMSO) 9.9(1H, s); 8.45(1H, br.s); 8.39(1H, br.s); 7.64(1H, d); 7.46–7.43(2H, m); 7.32–7.29(1H, t); 7.19(2H, d); 7.08(1H, d); 6.94(2H, d); 5.01(1H, d); 4.30(1H, t); 3.60–3.52(1H, m); 2.85–2.79(1H, m); 2.71–2.63(1H, m); 2.20(3H, s); 1.89–1.85(1H, m); 1.71–1.66(1H, m); 1.24(3H, d).

EXAMPLE 59

(1S,2R)-N-[4'-(2-Hydroxy-1-methyl-4-pyridin-3-yl-butoxy)biphenyl-3-yl]-methanesulfonamide

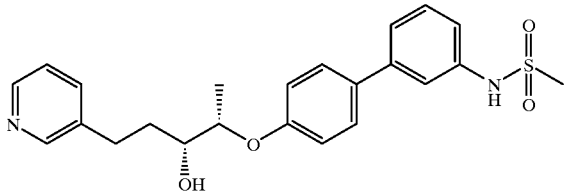

a) 3-Bromomethanesulfonanilide

Triethylamine (0.6 ml) was added to a stirred solution of 3-bromoaniline (0.5 ml) in dichloromethane (10 ml). The resulting mixture was stirred at room temperature for 15 minutes and then methanesulfonylchloride (0.36 ml) in dichloromethane (5 ml) was added dropwise. The reaction mixture was stirred 3 hours at room temperature. Water was added and the product was extracted with dichloromethane. The combined extracts were dried over anhydrous magnesium sulfate, filtered and concentrated under reduced pressure. The residue was purified by column chromatography over silica gel eluting with dichloromethane, then methanol to give the sub-title compound as a solid (0.662 g).

m.p. 109° C.

$^1$H NMR (DMSO) 9.99(1H, br.s); 7.37(1H, s); 7.31–7.26 (2H, m); 7.24–7.15(1H, m); 3.04(3H, s).

b) (1S,2R)-N-[4'-(2-Hydroxy-1-methyl-4-pyridin-3-yl-butoxy)biphenyl-3-yl]-methanesulfonamide Prepared according to the method described in Example 12b) from (1S,2R)-4-(2-hydroxy-1-methyl-4-pyridin-3-ylbutoxy)benzeneboronic acid (0.150 g, Example 33), 3-bromomethane sulfonanilide (0.250 g), 2M aqueous sodium carbonate (0.50 ml) and tetrakis(triphenylphosphine)palladium (0) (0.020 g) in ethanol (3 ml) with heating at 90° C. for 2 hours. After work up, the residue was purified by normal-phase HPLC eluting with a gradient of 0–25% ethanol in dichloromethane, then by reverse-phase HPLC eluting a gradient of 25–100% acetonitrile in 0.1 w/v aqueous ammonium acetate solution to give the title compound as an oil (0.060 g).

MS(APCI) 427 (M+H)$^+$ $^1$H NMR (DMSO) 9.82(1H, br.s); 8.45(1H, s); 8.40(1H, d); 7.64(1H, d); 7.50(2H, d); 7.41–7.31(4H, m); 7.14(1H, d); 7.01(2H, d); 5.01(1H, d); 4.37–4.31(1H, m); 3.61–3.02(3H, s); 2.87–2.78(1H, m); 2.70–2.62(1H, m); 1.91–1.82(1H, m); 1.71–1.62(1H, m); 1.24(3H, d).

EXAMPLE 60

(1S,2R)-4'-(2-Hydroxy-1-methyl-4-pyridin-3-yl-butoxy)biphenyl-4-sulfonic acid amide

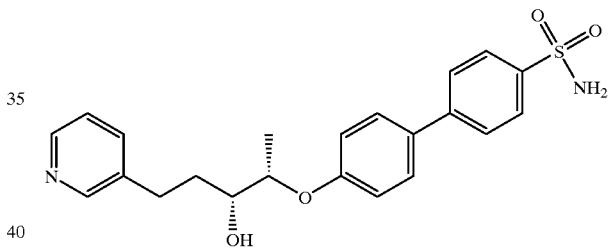

Prepared according to the method described in Example 12b) from (1S,2R)-4-(2-hydroxy-1-methyl-4-pyridin-3-ylbutoxy)benzeneboronic acid (0.30 g, Example 33), 4-bromophenylsulfonic acid amide (0.26 g), ethanol (6 ml), 2M aqueous sodium carbonate (1.0 ml) and tetrakis(triphenylphosphine)palladium (0) (0.03 g) with heating at 90° C. for 6 hours. After work-up, the residue was purified by column chromatography on silica gel eluting with 5:95 methanol:ethyl acetate to give the title compound as a solid (0.04 g).

m.p. 222–223° C.

MS (APCI) 413/414 (M–H)$^-$ $^1$NMR (DMSO) 8.44(1H, s); 8.39(1H, d); 7.81(4H, q); 7.64(2H, d); 7.36(2H, br.s); 7.30(1H, dd); 7.04(2H, d); 5.01(1H, d); 4.36(1H, m); 3.55(1H, m); 2.82(1H, m); 2.65 (1H, m); 1.88(1H, m); 1.66(1H, m); 1.24(3H, d).

EXAMPLE 61

(1S,2R)-4'-(2-Hydroxy-1-isopropyl-4-pyridin-3-yl-butoxy)biphenyl-3-sulfonic acid amide

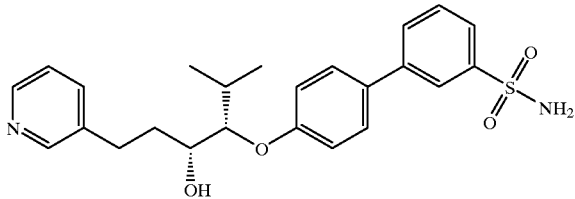

a) (2S)-2-(4-Bromophenoxy)-3-methylbutanoic acid, methyl ester

Diethylazodicarboxylate (17.5 ml) in dry toluene (60 ml) was added dropwise over 30 minutes to a cooled, stirred solution of triphenylphosphine (34 g), methyl (R)-2-hydroxy-3-methylbutanoate (17 g, *J.Am. Chem. Soc., (1990),* 112, 21, 7659) and 4-bromophenol (24 g) in dry toluene (180 ml). The resulting solution was stirred at room temperature for 30 minutes and was then concentrated under reduced pressure to approximately half the original volume. A mixture of isohexane (700 ml) was added and the mixture stirred at room temperature for 20 minutes. The solution was filtered to remove triphenylphosphine oxide and the filtrate concentrated under reduced pressure. The residue was purified by column chromatography over silica eluting with isohexane: dichloromethane (1:4) then (2:3) to give the sub-title compound as an oil (28 g).

$^1$H NMR (CDCl$_3$) 7.36(2H, d); 6.76(2H, d); 4.33 (1H, d); 3.74(3H, s); 2.35–2.2(1H, m); 1.06(6H, t).

b) (2S)-2-(4-Bromophenoxy)-3-methyl-1-butanol

Solid sodium borohydride (11.8 g) was added with cooling in three portions over 3 days to a stirred solution of (2S)-2-(4-bromophenoxy)-3-methylbutanoic acid, methyl ester (27.7 g) in ethanol (400 ml). The reaction was concentrated under reduced pressure and the residue partitioned between 2M hydrochloric acid (400 ml) and ether. The organic layer was dried over anhydrous magnesium sulfate filtered and concentrated under reduced pressure. The residue was purified by column chromatography over silica gel eluting with dichloromethane:isohexane (1:1) to give the sub-title compound as an oil (13.7 g).

$^1$H NMR (CDCl$_3$) 7.37(2H, d); 6.86(2H, d); 4.15–4.05 (1H, m); 3.85–3.75(2H, m); 2.15–2.0(1H, m); 0.99(3H, d); 0.96(3H, d).

c) (3RS, 4S)-4-(4-Bromophenoxy)-5-(methyl)-1-(pyridin-3-yl)-hex-1-yn-3-ol

Oxalyl chloride (6.0 ml) was added dropwise to a solution of dimethylsulfoxide (7.5 ml) in dry dichloromethane (300 ml) at −70° C. The resulting solution was stirred for 15 minutes and then a solution of (2S)-2-(4-bromophenoxy)-3-methyl-1-butanol (13 g) in dry dichloromethane (100 ml) was added dropwise at −70° C. The mixture was stirred for a further 15 minutes and then triethylamine (45 ml) was added. The mixture was allowed to warm to 10° C. with stirring. The mixture was then diluted with isohexane (600 ml), stirred for 10 minutes, filtered and concentrated under reduced pressure. The residue was dissolved in isohexane (500 ml) and ether (50 ml) and then refiltered and concentrated under reduced pressure. The residue was dissolved in dry tetrahydrofuran (100 ml) and added at −78° C. to a solution of 1-lithio-2-pyridin-3-ylacetylene [generated by the addition of n-butyllithium (2.5 M in hexanes, 30 ml) to a solution of pyridin-3-ylacetylene (8.0 g) (*J. Amer. Chem. Soc.* 1935, 57, 1284) in tetrahydrofuran (150 ml) at −78° C. with stirring for 15 minutes]. The mixture was allowed to room temperature over 30 minutes and was poured into saturated aqueous ammonium chloride (200 ml). The layers were separated and the organic layer dried over anhydrous magnesium sulfate, filtered and concentrated under reduced pressure. The residue (20 g) was purified by column chromatography over silica eluting with dichloromethane then dichloromethane:ethyl acetate (4:1) to give the sub-title compound as an oil and as a 3:1 mixture of diastereomers (15.9 g).

MS (APCI) 360,362 (M+H)$^+$ d) (3RS, 4S)-4-(4-Bromophenoxy)-5-(methyl)-1-pyridin-3-yl-3-hexanol (3RS, 4S)-4-(4-Bromophenoxy)-5-(methyl)-1-pyridin-3-yl-hex-1-yn-3-ol (13.6 g) was dissolved in ethyl acetate (350 ml) and hydrogenated at 3 atmospheres for 6 days using 10% rhodium on charcoal (2.1 g) as catalyst. The catalyst and solvent were replaced 5 times during this period. The mixture was filtered through Celite® and the filtrate concentrated under reduced pressure to give a. The mixture was purified by HPLC eluting with dichoromethane:2-propanol (97:3) to give a mixed fraction containing reduced and unreduced (6.0 g), pure (3S, 4S)-4-(4-bromophenoxy)-5-(methyl)-1-pyridin-3-yl-3-hexanol (1.73 g) and pure (3R, 4S)-4-(4-bromophenoxy)-5-(methyl)-1-pyridin-3-yl-3-hexanol (2.73 g).

(3S,4S)-4-(4-Bromophenoxy)-5-methyl-1-pyridin-3-yl-3-hexanol $^1$H NMR (CDCl$_3$) 8.46–8.43(2H, m); 7.48(1H, dt); 7.35 (2H, d); 7.20(1H, dd); 6.84(2H, d); 3.93(1H, dd); 3.85–3.75 (1H, m); 2.95–2.83(1H, m); 2.78–2.65(1H, m); 2.15–2.05 (2H, m); 1.9–1.65(2H, m); 0.95(3H, d); 0.92(3H, d).

(3R,4S)-4-(4-Bromophenoxy)-5-methyl-1-pyridin-3-yl-3-hexanol $^1$H NMR (CDCl$_3$) 8.48–8.43(2H, m); 7.50(1H, dt); 7.35 (2H, d); 7.21(1H, dd); 6.86(2H, d); 4.06(1H, dd); 3.9–3.75 (1H, m); 2.95–2.85(1H, m); 2.75–2.63(1H, m); 2.1–1.95 (1H, m); 1.95–1.75(2H, m); 1.71(1H, d); 0.97(3H, d); 0.89 (3H, d).

e) 3-[4-(4-Bromophenoxy)-3-(tert-butyldimethylsilanyloxy)-5-methylhexyl]pyridine Solid tert-butyldimethylsilyl chloride (0.46 g) was added to a solution of (3R, 4S)-4-(4-bromophenoxy)-5-methyl-1-pyridin-3-yl-3-hexanol (0.93 g) andimidazole (0.26 g) in dry dimethylformamide (12 ml) and the resulting solution stirred at room temperature for 3 days. Water (100 ml) and ether (100 ml) were added. The organic phase was separated, dried over anhydrous magnesium sulfate, filtered and concentrated under reduced pressure. The residue was purified by column chromatography over silica gel eluting with dichloromethane then dichloromethane: hexane (1:1) to give the sub-title compound as an oil (0.70 g).

$^1$H NMR (CDCl$_3$) 8.43–8.40(1H, m); 8.33(IEH, d); 7.34 (2H, d); 7.32–7.28(1H, m); 7.16(1H, dd); 6.86(2H, d); 4.03(1H, t); 4.0–3.9(1H, m); 2.7–2.55(2H, m); 2.15–2.05 (1H, m); 1.95–1.75(2H, m); 1.01(3H, d); 0.99(3H, d); 0.89 (9H, s); 0.08(3H, s); 0.09(3H, s).

f) (1S,2R)-4'-(2-Hydroxy-1-isopropyl-4-pyridin-3-yl-butoxy)-biphenyl-3-sulfonic acid amide A solution of tert-butyllithium (1.7M in pentane, 1.7 ml) was added dropwise over 5 minutes to a solution of 3-[4-(4-Bromophenoxy)-3-(tert-butyldimethylsilanyloxy)-5-methylhexyl]pyridine (0.7 g, Example 61e)) andtri-isopropyl borate (0.75 ml) in tetrahydrofuran (20 ml) at −78° C. The solution was stirred for 30 minutes and then tert-butyllithium (0.5 ml) was added. The solution was stirred for a further 30 minutes and then tert-butyllithium (0.5 ml) was added. After stirring for 30 minutes a saturated solution of aqueous ammonium chloride (50 ml) was added followed by ethyl acetate (50 ml). The layers were separated, the organic layer separated, dried over anhydrous magnesium sulfate, filtered and concentrated under reduced pressure. The residue was purified by column chromatography over silica gel eluting with ether to give recovered starting material (0.29 g) and then with ethyl acetate:methanol (4:1) to give (1S,2R)-4'-[2-(tert-butyldimethylsilanyloxy)-1-isopropyl-4-pyridin-3-ylbutoxy]benzeneboronic acid. This was dissolved in toluene (5 ml) and ethanol (3.5 ml) and 3-bromobenzenesulfonamide (0.37 g), 2M aqueous sodium carbonate (2 ml) and tetrakis(triphenylphosphine)palladium (0) were added. The mixture was heated at 100° C. for 2 hours and then left to stir at room temperature overnight. The reaction mixture was concentrated under reduced pressure and methanol (10 ml) and concentrated hydrochloric acid (2 ml) were added to the residue. After stirring at room temperature for 2 hours the reaction mixture was concentrated under reduced pressure. Water (50 ml) was added to the residue and was neutralised by the to addition of solid sodium hydrogen carbonate. The aqueous phase was extracted with ethyl acetate, the combined extracts dried over anhydrous magnesium sulfate, filtered and concentrated under reduced pressure. The residue (0.60 g) was purified by column chromatography over silica gel eluting with dichloromethane then ether then ethyl acetate to give an oil (0.34 g). This was purified further by column chromatography over silica eluting with dichloromethane:ethanol (19:1). This material was then purified twice by reverse-phase HPLC eluting a gradient of 25–100% acetonitrile in 0.1 w/v aqueous ammonium acetate solution. The material recovered from this purification was triturated with isohexane to give a solid (0.20 g).

MS (APCI) 441 (M+H)+

1H NMR 8.37(2H, s); 8.04(1H, t); 7.83(1H, d); 7.73(1H, d); 7.65–7.5(4H, m); 7.37(2H, s); 7.26(1H, dd); 7.12(2H, d); 5.02(1H, d); 4.17(1H, dd); 3.7–3.55(1H, m); 2.85–2.7(1H, m); 2.7–2.55(1H, m); 2.25–2.05(1H, m); 1.9–1.7(1H, m); 1.7–1.5(1H, m); 0.95(3H, d).

EXAMPLE 62

(1S,2R)-[4'-(2-Hydroxy-1-methyl-4-pyridin-3-ylbutoxy)biphenyl-4-yl]urea

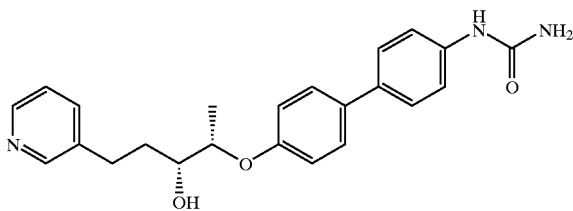

Prepared according to the method described in Example 12b) from (1S,2R)-4-(2-hydroxy-1-methyl-4-pyridin-3-ylbutoxy)benzeneboronic acid (0.15 g, Example 33), 4-bromophenylurea (0.16 g), 2M aqueous sodium carbonate (0.25 ml) and tetrakis(triphenylphosphine)palladium (0) (0.1 g) in ethanol (3 ml). The reaction mixture was heated at 100° C. for 3 hours. After cooling, the solution was concentrated under reduced pressure. The residue was triturated with acetone and then filtered through silica gel. The filtrate was concentrated under reduced pressure and purified by flash column chromatography eluting with 10% methanol in dichloromethane give the title compound as a solid (0.046 g).

m.p. 181–182° C.

MS (APCI) 392 (M+H)+

1H NMR (DMSO) 8.53(1H, s); 8.44 (1H, s); 8.38(1H, d); 7.63(1H, d); 7.49–7.42(6H, m); 7.31–7.27(1H, m); 6.95 (2H, d); 5.84(2H, s); 5.0(1H, s); 4.31–4.27(1H, m); 3.55–3.53 (1H, 2.86–2.59(2H, m); 1.90–1.80(1H, m); 1.67–1.57(1H, m); 1.23(3H, d).

EXAMPLE 63

(1S,2R)-4'-(2-Hydroxy-1-methyl-4-pyridin-3-ylbutoxy)-2-methyl-biphenyl-4-carboxylic acid (2-pyrrolidin-1-yl-ethyl)amide

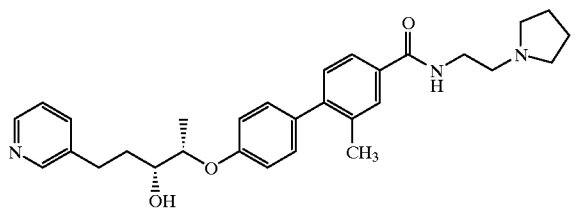

a) 4-Bromo-3-methyl-N-(2-pyrrolidin-1-yl-ethyl)benzamide

1-Ethyl-3-(3'-dimethylaminopropyl)carbodiimide hydrochloride (2.68 g) was added to a solution of 4-bromo-3-methyl benzoic acid (3.0 g), 1-(2-aminoethyl)pyrrolidine (1.78 ml) and 1-hydroxybenzotriazole hydrate (1.89 g) in dry N,N-dimethylformamide (30 ml). The reaction was stirred at room temperature for 24 hours. The solution was concentrated under reduced pressure. The residue was dissolved in ethyl acetate and washed with brine. The organic layer was dried over magnesium sulfate, filtered and concentrated under reduced pressure. The residue was purified by column chromatography over silica gel eluting with dichloromethane:methanol (9:1) to give the sub-title compound as an oil. (3.55 g).

MS(APCI) 313/315 (M+H)+

1H NMR(CDCl3) 8.51(1H, br.s); 7.73(1H, dd); 7.44(1H, d); 7.30–7.22(1H, m); 3.86(2H, q); 3.29(2H, t); 3.27–3.23 (4H, m); 2.30(3H, s); 2.05–1.98(4H, m).

b) (1S,2R)-4'-(2-Hydroxy-1-methyl-4-pyridin-3-yl-butoxy)-2-methyl-biphenyl-4-carboxylic acid (2-pyrrolidin-1-yl-ethyl)-amide Prepared according to the method described in Example 12b) from (1S,2R)-4-(2-hydroxy-1-methyl-4-pyridin-3-ylbutoxy)benzeneboronic acid (0.15 g, Example 33), 4-bromo-3-methyl-N-(2-pyrrolidin-1-yl-ethyl)benzamide (0.31 g, Example 63a)), 2M aqueous sodium carbonate (0.57 ml) and tetrakis(triphenylphosphine)palladium(0) (0.012 g) in ethanol(5 ml) with heating at reflux for 4 hours. After work up, the residue was purified by normal-phase HPLC eluting with a gradient of 0–10% ethanol in dichloromethane to give the title compound as an oil. (0.14 g).

MS(APCI) 488(M+H)+

1H NMR(CDCl3) 8.82(1H, br.t); 8.51(1H, d); 8.45(1H, dd); 8.0(1H, s); 7.92(1H, d); 7.56(1H, d); 7.27(1H, s); 7.25–7.22(1H, m); 7.21(2H, d); 6.92(2H, d); 4.42–4.39(1H, m); 3.93(2H, q); 3.91–3.87(1H, m); 3.60(4H, m); 3.41(2H, t); 3.01–2.93(1H, m); 2.78–2.70(1H, m); 2.50(1H, br.s); 2.27(3H, s); 2.16(4H, br.s); 1.91–1.83(2H, m); 1.32(3H, d).

EXAMPLE 64

(1S,2R)-4'-(2-Hydroxy-1-methyl-4-pyridin-3-yl-butoxy)biphenyl-3-sulfonic acid 2,2,2-trifluoroethyl) amide

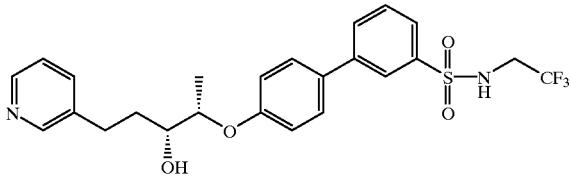

a) (N-2,2,2-Trifluoroethyl)-3-bromobenzenesulfonic acid amide

3-Bromobenzenesulfonyl chloride (1.27 g) was added to a stirred solution of 2,2,2-trifluoroethylamine hydrochloride (0.8 g) and triethylamine (1.7 ml) in tetrahydrofuran (30 ml) and the resulting mixture was stirred for 20 hours at room temperature. The reaction mixture was concentrated and the residue partitioned between ether (20 ml) and 2M hydrochloric acid (30 ml). The mixture was separated and the aqueous layer extracted with ether and the combined extracts were dried over anhydrous magnesium sulfate and concentrated. The residue was recrystallised from hexane to afford the sub-title compound as a solid (0.60 g).

m.p. 98–99° C.
MS (GC) 317, 319 (M)+
$^1$H NMR (CDCl$_3$) 8.02 (1H, t); 7.81 (1H, ddd); 7.74 (1H, ddd); 7.42 (1H, t); 4.95 (1H, t); 3.71 (2H, m).

b) (1S,2R)-4'-(2-Hydroxy-1-methyl-4-pyridin-3-yl-butoxy)biphenyl-3-sulfonic acid (2,2,2-trifluoroethyl)amide Prepared according to the method described in Example 12b) from (1S,2R)-4-(2-hydroxy-1-methyl-4-pyridin-3-ylbutoxy)benzeneboronic acid (0.15 g, Example 33), (N-2,2,2-trifluoroethyl)-3-bromobenzenesulfonic acid amide (0.25 g, Example 64a)), 2M aqueous sodium carbonate (0.57 ml) and tetrakis(triphenylphosphine)palladium (0) (0.014 g) in ethanol (5 ml) with heating at 90° C. for 2 hours. After work up, the residue was purified by normal-phase HPLC eluting with a gradient of 0–10% ethanol in dichloromethane to give the title compound as a solid (0.17 g).

m.p. 47–48° C.
MS(APCI) 495(M+H)+
$^1$H NMR(CDCl$_3$) 8.46(1H, d); 8.42(1H, dd); 8.01(1H, s); 7.78–7.70(2H, m); 7.58–7.49(2H, m); 7.45(2H, d); 7.26–7.22(1H, m); 6.93(2H, d); 4.41–4.29(1H, m); 3.86–3.80(1H, m); 3.70(2H, q); 2.97–2.91(1H, m); 2.77–2.67(1H, m); 1.88–1.81(2H, m); 1.30(3H, d).

EXAMPLE 65

(1S,2R)-1-[4'-(2-Hydroxy-1-methyl-4-pyridin-3-ylbutoxy)-biphenyl-4-yl]-3methylurea

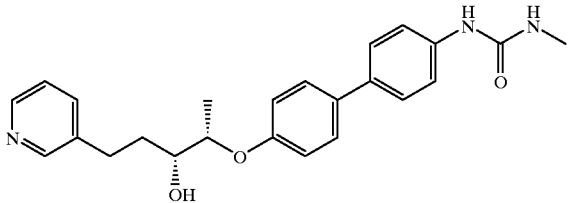

a) N-(4-Bromophenyl)-N'-methyl urea

A solution of methylamine in tetrahydrofuran (2M, 4 ml) was added to a solution of phenylisocyanate (1.06 g). An immediate precipitate of the product formed. The reaction mixture was diluted with hexane (100 ml) and then filtered to give the sub-title compound as a foam (0.90 g).

MS (APCI) 229 (M–H)−
$^1$H NMR (DMSO) 8.63(1H, s); 7.37(4H, s); 6.03(1H, q); 2.62(3H, d).

b) (1S,2R)-1-[4'-(2-Hydroxy-1-methyl-4-pyridin-3-ylbutoxy)-biphenyl-4-yl]-3-methylurea Prepared according to the method described in Example 12b) from (1S,2R)-4-(2-hydroxy-1-methyl-4-pyridin-3-ylbutoxy)benzeneboronic acid (0.149 g, Example 33), N-(4-bromophenyl)-N'-methyl urea (0.225 g) 2M aqueous sodium carbonate (1.0 ml) and tetrakis(triphenylphosphine) palladium (0) (0.028 g) in ethanol (3 ml). The reaction mixture was heated in a sealed vial at 100° C. for 2 hours. After cooling, the solution was concentrated under reduced pressure. The residue was purified by chromatography over silica eluting with tetrahydrofuran:hexane (1:1). The residue was further purified by chromatography over silica gel eluting dichloromethane:ethanol (9:1). The residue was then further purified by reverse-phase HPLC eluting a gradient of 25–100% acetonitrile in 0.1 w/v aqueous ammonium acetate solution. The HPLC fractions were concentrated under reduced pressure, the residue dissolved in ethanol, filtered and concentrated under reduced pressure to give the title compound as a solid (0.050 g).

m.p. 139–141° C.
MS (APCI) 406 (M+H)+
$^1$H NMR (DMSO) 8.54(1H, s); 8.44(1H, s); 8.39(1H, d); 7.63(1H, d); 7.49(2H, d); 7.45(4H, s); 7.30(1H, t); 6.95(2H, d); 6.01(1H, d); 4.98(1H, d); 4.29(1H, quintet); 3.6–3.5(1H, m); 2.85–2.75(1H, m); 2.7–2.6(4H, m); 1.9–1.8(1H, m); 1.7–1.6(1H, m); 1.24 (3H, s).

EXAMPLE 66

(1S,2R)-2-[4'-(2-Hydroxy-1-methyl-4-pyridin-3-yl-butoxy)-biphenyl-4-yl]-N-isopropylactamide

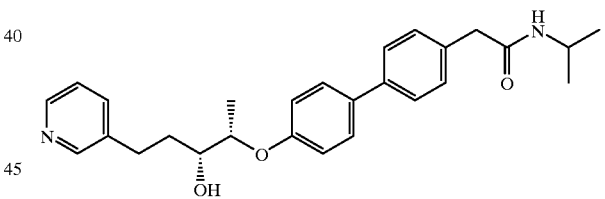

(1S,2R)-[4'-(2-Hydroxy-1-methyl-4-pyridin-3-yl-butoxy)-biphenyl-4-yl]-acetic acid (Example 55, 0.07 g), isopropylamine (0.012 g), 1-(3-dimethylaminopropyl)-3-ethylcarboiimide hydrochloride (0.038 g) and 1-hydroxybenzotriazole (0.027 g) were dissolved in dimethylformamide (2 ml) and stirred for 16 hours at room temperature. The dimethylformamide was removed by vacuum distillation, the residue dissolved in dichloromethane, filtered and purified by normal-phase HPLC eluting with a gradient of 0–10% ethanol in dichloromethane to give the title compound as a solid (0.061 g).

m.p. 103–104° C.
MS (APCI) 433 (M+H)+
$^1$H NMR (CDCl$_3$) 8.51(1H, d); 8.47 (1H, dd); 7.58–7.49 (5H, m); 7.30–7.26(2H, m); 7.25–7.20(1H, m); 6.95(2H, dd); 5.2(1H, br.s); 4.40–4.37(1H, m); 4.12–4.05(1H, m); 3.89– 3.85(1H, m); 3.56(2H, S); 2.96–2.91(1H, m); 2.76–2.71(1H, m); 2.13(1H, m); 1.90–1.81(2H, m); 1.30(3H, d); 1.10(6H, d).

EXAMPLE 67

Comparative (1S,2R)-N-Cyclopropyl-2-[4'-(2-hydroxy-1-methyl-4-pyridin-3-yl-butoxy)-biphenyl-4-yl]-acetamide

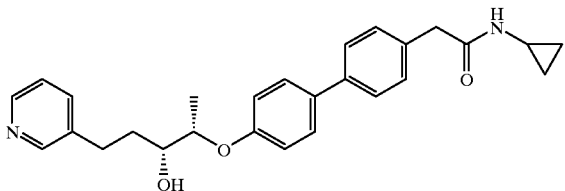

Prepared according to the method described in Example 66. (1S,2R)-[4'-(2-hydroxy-1-methyl-4-pyridin-3-yl-butoxy)-biphenyl-4-yl]acetic acid (Example 55, 0.07 g), cyclopropylamine (0.011 g), 1-(3-dimethylaminopropyl)-3-ethylcarbodiimide hydrochloride (0.038 g) and 1-hydroxybenzotriazole (0.027 g) were dissolved in dimethylformamide (2 ml) and stirred for 16 hours at room temperature. The dimethylformamide was removed by vacuum distillation, the residue was dissolved in dichloromethane, filtered and purified by normal-phase HPLC eluting with a gradient of 0–10% ethanol in dichloromethane to give the title compound as a solid (0.063 g).

m.p. 117–118° C.

MS (APCI) 431 (M+H)$^+$ $^1$H NMR (CDCl$_3$) 8.51(1H, d); 8.47(1H, dd); 7.55–7.48 (5H, m); 7.29–7.26(1H, m); 7.25–7.20(2H, m); 6.96(2H, dd); 5.50(1H, br.s); 4.41–4.37 (1H, m); 3.90–3.80(1H, m); 3.57(2H, s); 3.05–2.90(1H, m); 2.80–2.65(2H, m); 2.18(1H, d); 1.90–1.80(2H, m); 1.30(3H, d); 0.75–0.70(2H, m); 0.45–0.40(2H, m).

EXAMPLE 68

(1S,2R)-2-[4'-(2-Hydroxy-1-methyl-4-pyridin-3-yl-butoxy)biphenyl-4-yl]-1-pyrrolidin-1-ylethanone

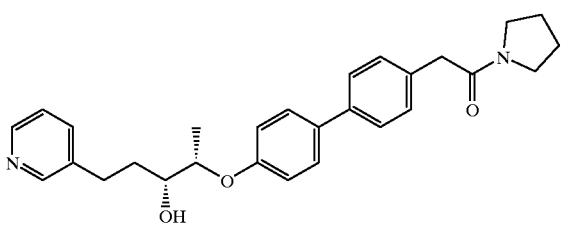

Prepared according to the method described in Example 66. (1S,2R)-[4'-(2-Hydroxy-1-methyl-4-pyridin-3-yl-butoxy)-biphenyl-4-yl]-acetic acid (Example 55, 0.07 g),pyrrolidine (0.014 g), 1-(3-dimethylaminopropyl)-3-ethylcarbodiimide hydrochloride (0.038 g) and 1-hydroxybenzotriazole (0.027 g) were dissolved in dimethylformamide (2 ml) and stirred for 16 hours at room temperature. The dimethylformamide was removed by vacuum distillation, the residue was dissolved in dichloromethane, filtered and purified by normal-phase HPLC eluting with a gradient of 0–10% ethanol in dichloromethane to give the title compound as a glass (0.068 g).

MS (APCI) 435 (M+H)$^+$ $^1$H NMR (CDCl$_3$) 8.51(1H, d); 8.46 (1H, dd); 7.55(1H, dt); 7.50–7.47(4H, m); 7.32(2H, d); 7.24–7.22(1H, m); 6.95–6.92 (2H, m); 4.40–4.36(1H, m); 3.87–3.86(1H, m); 3.68(2H, s); 3.53–3.44(4H, m); 3.0–2.90(1H, m); 2.80–2.65 (1H, m); 2.15(1H, d); 2.0–1.80(6H, m); 1.30(3H, d).

EXAMPLE 69

(1S,2R)-2-Methyl-4'-(2-hydroxy-1-methyl-4-pyridin-3-yl-butoxy)biphenyl-5-sulfonic acid amide

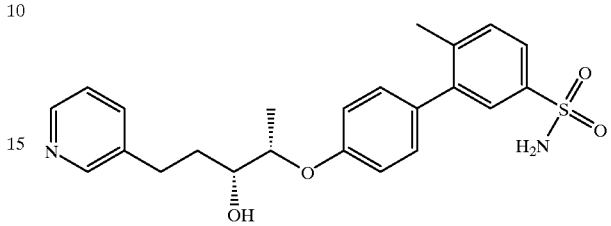

a) 3-Bromo-4-methylphenylsulfonic acid amide

A solution of 3-bromo-4-methylaniline (3.0 g) in concentrated hydrochloric acid (15 ml) was cooled to below 5° C. A solution of sodium nitrite (1.17 g) in water (4 ml) was added dropwise whilst maintaining the internal temperature below 5° C. After addition was complete anhydrous magnesium chloride (2.0 g) was added (CARE: exothermic). A saturated solution of sulfur dioxide in glacial acetic acid (40 ml) was prepared at 0° C. and copper (II) chloride (0.22 g) was added. To this acetic acid solution at room temperature was added the solution of the diazonium salt, and the mixture warmed to 30° C. After 1 hr the mixture was poured into saturated brine and extracted with ethyl acetate. The combined extracts were washed with water and brine, dried over magnesium sulphate, filtered and evaporated. The residual oil was dissolved in tetrahydrofuran (50 ml) and ammonium hydroxide (50 ml) added. After 2 hours the mixture was diluted with water and extracted with ethyl acetate. The combined extracts were dried over magnesium sulfate, filtered and evaporated. The crude material was purified by column chromatography on silica gel eluting with 1:1 ethyl acetate:isohexane, to afford the sub-title compound as a solid (0.49 g).

MS (APCI-ve) 249/251 (M–H)$^-$ $^1$H NMR (CDCl$_3$) 8.09(1H, s); 7.76(1H, d); 7.38(1H, d); 4.85(2H, br.s); 2.48(3H, s).

b) (1S ,2R)-2-Methyl-4'-(2-hydroxy-1-methyl-4-pyridin-3-yl-butoxy)biphenyl-5-sulfonic acid amide Prepared according to the method described in Example 12b) from (1S,2R)-4-(2-hydroxy-1-methyl-4-pyridin-3-ylbutoxy)benzeneboronic acid (0.15 g, Example 33), 3-bromo-4-methylphenylsulfonic acid amide (0.25 g, Example 69a)), ethanol (3 ml), 2M aqueous sodium carbonate (0.5 ml) and tetrakis(triphenylphosphine)palladium (0) (0.03 g) with heating at 90° C. for 3 hours. After work-up, the residue was purified by normal-phase HPLC eluting with a gradient of 0–25% ethanol in dichloromethane to give the title compound as a foam (0.19 g).

MS (APCI) 427 (M+H)$^+$ $^1$H NMR (CDCl$_3$) 8.48(1H, s); 8.44(1H, d); 7.78(1H, s); 7.77(1H, d); 7.57(1H, d); 7.39(1H, d); 7.25(1H, d); 7.21(2H, d); 6.93(2H, d); 5.00(2H, br.s); 4.40(1H, m); 3.87(1H, m); 2.95(1H, m); 2.75(1H, m); 2.33(3H, s); 1.85(2H, m), 1.33 (3H, d).

EXAMPLE 70

(1S,2R)-2,2,2-Trifluoro-N-[4'-(2-hydroxy-1-methyl-4-pyridin-3-yl-butoxy)-biphenyl-3-yl]-N-methylacetamide

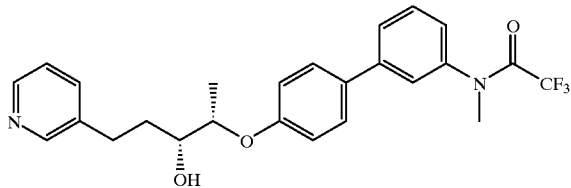

a) N-(3-bromo-phenyl)-2,2,2-trifluoro-N-methylacetamide

N-(3-Bromophenyl)-2,2,2-trifluoroacetamide (*J. Chem. Soc.*, 1952, 4014) in tetrahydrofuran (3 ml) was added dropwise to sodium hydride (0.16 g) in tetrahydrofuran (5 ml). The reaction mixture was stirred for 30 minutes at room temperature. Iodomethane (0.25 ml) was added dropwise to the reaction mixture and it was stirred overnight at room temperature. Water was added and the product extracted with ethyl acetate. The combined extracts were dried over anhydrous magnesium sulfate, filtered and concentrated under reduced pressure. The residue was purified by column chromatography over silica gel eluting with iso-hexane: dichloromethane (1: 1) to give the sub-title compound as an oil (0.385 g).

$^1$H NMR (CDCl$_3$) 7.57(1H, d); 7.43(1 H, s); 7.32(1H, t); 7.21 (1H, d); 3.35(3H, s).

b) (1S,2R)-2,2,2-Trifluoro-N-[4'-(2-hydroxy-1-methyl-4-pyridin-3-yl-butoxy)-biphenyl-3-yl]-N-methylacetamide Prepared according to the method described in Example 12b) from (1S,2R)-4-(2-hydroxy-1-methyl-4-pyridin-3-ylbutoxy)benzeneboronic acid (0.150 g, Example 33), N-(3-bromo-phenyl)-2,2,2-trifluoro-N-methylacetamide (0.282 g), 2M aqueous sodium carbonate (0.50 ml) and tetrakis (triphenylphosphine)palladium (0) (0.020 g) in ethanol (3 ml) with heating at 90° C. for 2 hours. After work up, the residue was purified by normal-phase HPLC eluting with a gradient of 0–25% ethanol in dichloromethane. The product obtained was dissolved in dichloromethane (3 ml) and cooled to 0° C. Trifluoroacetic anhydride (0.09 ml) was added dropwise, the reaction mixture stirred for 1 hour at room temperature, before concentrating under reduced pressure. Methanol (10 ml) and water (10 ml) were added and the resulting mixture was stirred for 30 minutes at room temperature. The product was extracted with ethyl acetate, and the combined extracts were dried over anhydrous magnesium sulfate, filtered and concentrated under reduced pressure to give the title compound as an oil (0.148 g).

MS(APCI) 459 (M+H)$^+$ $^1$H NMR (CDCl$_3$) 8.82 (1H, s); 8.65(1H, d); 8.18(1H, d); 7.74(1H, t); 7.57(1H, d); 7.52–7.45(3H, m); 7.40(1H, s); 7.18(1H, d); 6.97(2H, d); 5.10(1H, br.s); 4.42–4.36(1H, m); 3.84–3.79(1H, m); 3.40(3H, s); 3.18–3.10(1H, m); 3.02–2.94(1H, m); 1.96–1.90(2H, m); 1.31(3H, d).

EXAMPLE 71

(1S,2R)-4'-(2-Hydroxy-1-methyl-4-pyridin-3-ylbutoxy)biphenyl-3,4-dicarbonitrile

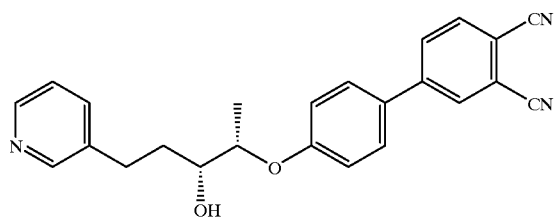

Prepared according to the method described in Example 12b) from (1S,2R)-4-(2-hydroxy-1-methyl-4-pyridin-3-ylbutoxy)benzeneboronic acid (0.197 g, Example 33), 4-iodo-1,2-dicyanobenzene (0.421 g, *Can. J. Chem.*, 1985, 63, 3057), 2M aqueous sodium carbonate (0.50 ml) and tetrakis(triphenylphosphine)palladium (0) (0.054 g) in ethanol (3 ml). The reaction mixture was heated in a sealed vial at 90° C. for 4 hours. After cooling, the solution was concentrated under reduced pressure and the residue purified by chromatography over silica eluting with ethyl acetate. The residue was further purified by chromatography over silica gel eluting with dichloromethane:2-propanol (19:1). The residue was then further purified by reverse-phase HPLC eluting a gradient of 25–100% acetonitrile in 0.1 w/v aqueous ammonium acetate solution. The HPLC fractions were concentrated under reduced pressure, the residue dissolved in dichloromethane, filtered and concentrated under reduced pressure. The residue was triturated with ether to give the title to compound as a solid (0.060 g).

m.p. 135.5–137° C.

MS (APCI) 384 (M+H)$^+$ $^1$H NMR (DMSO) 8.47–8.43(2H, m); 8.38(1H, dd); 8.25–8.12(2H, m); 7.79(2H, d), 7.63(1H, dt); 7.30(1H, dd); 7.06(2H, d); 5.03(1H, d); 4.41(1H, quintet); 3.63–3.5(1H, m); 2.9–2.75(1H, m); 2.75–2.6(1H, m); 1.95–1.8(1H, m); 1.75–1.55(1H, m); 1.24(3H, d).

EXAMPLE 72

(3R,4S)-1-Pyridin-3-yl-4-[3'-(pyrrolidine-1-sulfonyl)biphenyl-4-yloxy]pentan-3-ol

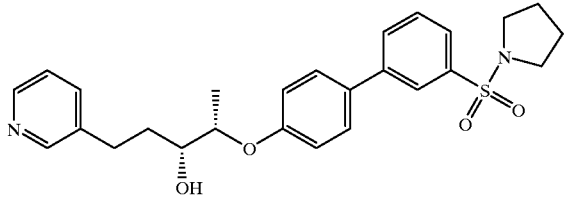

a) 3-bromobenzenesulfonic acid, pyrrolidinyl amide

A solution of pyrrolidine (0.33 ml) and triethylamine (0.6 ml) in dichloromethane (10 ml) was added dropwise to a stirred solution of 3-bromobenzenesulfonyl chloride (1 g) in dichloromethane (20 ml), and the mixture stirred at room temperature for 18 hours. The reaction was poured onto water, and the aqueous mixture was extracted with dichloromethane. The combined organic extracts were washed with brine, dried over magnesium sulfate, filtered, and concentrated under reduced pressure to give an oil. This was purified by column chromatography over silica gel, eluting with ethyl acetate isohexane (1:4) to give the sub-title compound as a solid (1.10 g)

m.p. 82–84° C.

MS (APCI) 290(M+H)+

1H NMR (DMSO) 7.95–7.9(2H, m); 7.85–7.8(1H, m); 7.60(1H, t); 3.2–3.13(4H, m); 1.75–1.6(4H; m).

b) (3R,4S )-1-Pyridin-3-yl-4-[3'-(pyrrolidine-1-sulfonyl) biphenyl-4-yloxy]pentan-3-ol Prepared according to the method described in Example 12b) from (1S,2R)-4-(2-hydroxy-1-methyl-4-pyridin-3-ylbutoxy)benzeneboronic acid (0.150 g, Example 33), 3-bromobenzenesulfonic acid, pyrrolidinyl amide (0.290 g), 2M aqueous sodium carbonate (0.50 ml) and tetrakis (triphenylphosphine)palladium(0) (0.025 g) in ethanol (3 ml). The reaction mixture was heated at 90° C. for 4 hours. After cooling, the solution was concentrated under reduced pressure, taken up in ethanol and concentrated again (twice). The residue was triturated with acetone and then filtered through silica gel. The filtrate was concentrated under reduced pressure, dissolved in dichloromethane, filtered and purified by normal-phase HPLC eluting with a gradient of 0–25% ethanol in dichloromethane to give a gum, which was further purified by reverse-phase HPLC to give the title compound as a foam (0.137 g).

MS (APCI) 467 (M+H)+.

1H NMR (DMSO) 8.44(1H, s); 8.38(1H, d); 7.95–7.88 (2H, m); 7.75–7.6(5H, m); 7.30(1H, q); 7.4(2H, d); 5.01(1H, d); 4.4–4.3(1H, m); 3.6–3.5(1H, m); 3.18(4H, t); 2.9–2.6 (2H, br.m); 1.92–1.8(1H, m); 1.7–1.6(5H, m);1.25(3H, d).

EXAMPLE 73

(1S,2R)-6-Fluoro-4'-(2-hydroxy-1-methyl-4-pyridin-3-yl-butoxy)-biphenyl-3-carbonitrile

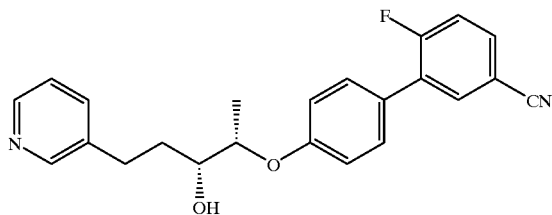

Prepared according to the method described in Example 12b) from (1S,2R)-4-[2-(tert-butyldimethylsilanyloxy)-1-methyl-4-pyridin-3-ylbutoxyl]enzeneboronic acid (0.20 g, Example 33), 3-bromo-4-fluorobenzonitrile (0.27 g), 2M aqueous sodium carbonate (0.76 ml) and tetrakis (triphenylphosphine)palladium (0) (0.019 g) in ethanol (5 ml) with heating at 90° C. for 4 hours. After work up, the residue was purified by normal-phase HPLC eluting with a gradient of 0–10% ethanol in dichloromethane to give the title compound as an oil (0.22 g).

MS(APCI) 377(M+H)+

1H NMR(CDCl3) 8.51(1H, d); 8.46(1H, dd); 7.73(1H, dd); 7.62–7.54(2H, m); 7.45(2H, dd); 7.43–7.22(2H, m); 6.97(2H, d); 4.42–4.39(1H, m); 3.87–3.86(1H, m); 2.96–2.94(1H, m); 2.76–2.72(1H, m); 2.21(1H, d); 1.90–1.82(2H, m); 1.32(3H, d).

EXAMPLE 74

(1S,2R)-4'-(2-Hydroxy-1-methyl-4-pyridin-3-yl-butoxy)-5-trifluoromethyl-biphenyl-3-sulfonic acid amide

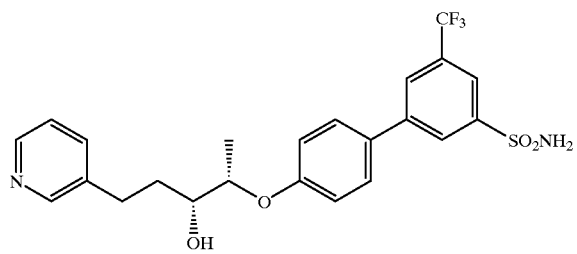

a) 3-Bromo-5-trifluoromethylbenzenesulfonamide

3-Amino-5-bromobenzotrifluoride was added to concentrated hydrochloric acid (20 ml) and cooled to −5° C. A saturated solution of sodium nitrite (3.88 g) in water (4 ml) was dropwise added at such a rate to maintain the temperature below 0° C. Magnesium chloride (8 g) was added (CARE: exotherm) and the resulting mixture added with stirring to a saturated solution of sulfur dioxide in acetic acid (37.5 ml) and toluene (20 ml), containing cupric chloride (2.75 g) at room temperature. The mixture was stirred for 16 hours, poured into water and extracted into toluene. The combined toluene extracts were washed with water, dilute sodium hydrogen carbonate, dried over anhydrous magnesium sulfate and concentrated. The residue was dissolved in tetrahydrofuran (200 ml) and 880 ammonia (50 ml) was added to the solution. The mixture was stirred at room temperature for 4 hours and then concentrated under reduced pressure. The residue was partitioned between water and ethyl acetate. The combined ethyl acetate extracts were dried over anhydrous magnesium sulfate and concentrated to afford the sub-title compound as a solid (4.2 g).

m.p. 174–175° C.

MS (APCI) 302/304 (M–H+)

1H NMR (CDCl3) 8.31 (1H, s); 8.27 (1H, s); 8.11(1H, s); 7.72 (2H, s).

b) (1S,2R)-4'-(2-Hydroxy-1-methyl-4-pyridin-3-yl-butoxy)-5-trifluoromethyl-biphenyl-3-sulfonic acid amide Prepared according to the method described in Example 12b) from (1S,2R)-4-(2-hydroxy-1-methyl-4-pyridin-3-ylbutoxy)benzeneboronic acid (0.20 g, Example 33), 3-bromo-5-trifluoromethylbenzosulphonamide (0.40 g, Example 74), 2M aqueous sodium carbonate (0.76 ml) and tetrakis(triphenylphosphine)palladium (0) (0.019 g) in ethanol (5 ml) with heating at 90° C. for 4 hours. After work up, the residue was purified by normal-phase HPLC eluting with a gradient of 0–10% ethanol in dichloromethane to give the title compound as a solid (0.24 g). m.p. 57–59° C.

MS(APCI) 481 (M+H)+

1H NMR(CDCl3) 8.49(1H, d); 8.45(1H, dd); 8.26(1H, s); 8.09(1H, s); 7.95(1H, s); 7.59–7.56(1H, m); 7.54(2H, d); 7.26–7.22(1H, m); 6.98(2H, d); 5.18(2H, br.s); 4.42–4.39 (1H, m); 3.87–3.84(1H, m); 2.95–2.93(1H, m); 2.77–2.73 (1H, m); 1.90–1.82(2H, m); 1.32(3H, d).

EXAMPLE 76

(1S,2R)-N-[3-Fluoro-4'-(2-hydroxy-1-methyl-4-pyridin-3-yl-butoxy)-biphenyl-4-yl]-acetamide

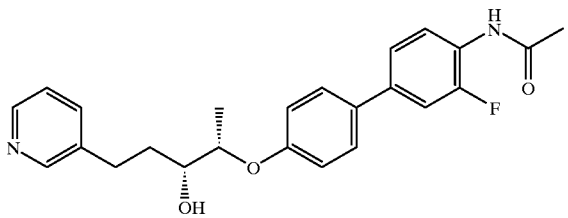

a) 2-Fluoro-4-iodo-acetanilide

2-Fluoro-4-iodoaniline (5.0 g) was heated at reflux in acetic anhydride (50 ml). The reaction was quenched by pouring into water and the product was extracted into ethyl acetate. The organic layers were combined, dried over anhydrous magnesium sulfate and filtered before evaporation. The product was purified by flash chromatography on silica gel, eluting with 4:1 isohexane:ethyl acetate to afford the sub-title compound as a solid (0.390 g).

m.p. 155–156° C.

MS (GCMS) 279 (M)+

$^1$H NMR (CDCl$_3$) 9.78 (1H, br.s); 7.73 (1H, t), 7.65 (1H, m); 7.50 (1H, bd); 2.08 (3H, s).

b) (1S,2R)-N-[3-Fluoro-4'-(2-hydroxy-1-methyl-4-pyridin-3-yl-butoxy)-biphenyl-4-yl]-acetamide Prepared according to the method described in Example 12b) from (1S,2R)-4-(2-hydroxy-1-methyl-4-pyridin-3-ylbutoxy)benzeneboronic acid (0.200 g, Example 33), 2-fluoro-4-iodo-acetanilide (0.279 g, Example 76a)), ethanol (3 ml), 2M aqueous sodium carbonate (0.67 ml) and tetrakis(triphenylphosphine)palladium (0) (0.030 g), heating at 90° C. for 4 hours. After work-up, the residue was purified by normal-phase HPLC, eluting with a gradient of 0–10% ethanol in dichloromethane to afford the title compound as a foam (0.107 g).

MS APCI 409 (M+H)+

$^1$H NMR (CDCl$_3$) 8.51 (1H, m); 8.45 (1H, m); 8.32 (1H, t); 7.56 (2H, m); 7.45 (2H, m); 7.20–7.32 (3H, m); 6.93 (2H, d); 4.38 (1H, m); 3.86 (1H, bm); 2.95 (1H, m); 2.73 (1H, m); 2.35 (1H, br.s); 2.39 (3H, s); 1.85 (2H, m); 1.31 (3H, d).

EXAMPLE 77

(1S,2R)-4'-(2-Hydroxy-1-methyl-4-pyridin-3-yl-butoxy)-6-methyl-biphenyl-3-carboxylic acid methylamide

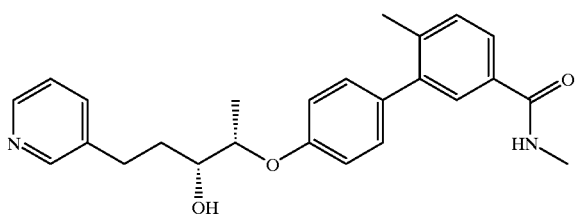

a) 3-Bromo-4-methylbenzoic acid, methyl amide

Oxalyl chloride (1.45 ml) was added dropwise to a stirred solution of 3-bromo-4-methylbenzoic acid (3.5 g) in dichloromethane (25 ml) and dimethylformamide (1 drop). The mixture was stirred at room temperature for 2 hours. The solvents were removed under reduced pressure, and the residue dissolved in tetrahydrofuran (10 ml). A portion of this solution (5 ml) was added dropwise to a stirred solution of methylamine in tetrahydrofuran (2M, 10 ml), and stirred at room temperature for 3 days. The mixture was poured into water, and the organic phase separated. The organic phase was extracted into dichloromethane, the combined organic phases were washed with brine, dried over magnesium sulfate, filtered, and the filtrate concentrated under reduced pressure. The residue was purified by column chromatography over silica eluting with ethyl acetate isohexane (3:1) to give the sub-title compound as solid (1.33 g).

m.p. 114–116° C.

MS (APCI) 228/230 (M+H)+

$^1$H NMR (DMSO) 8.5(1H, br d); 8.03(1H, d); 7.74(1H, dd); 7.44(1H, d); 2.77(3H, d); 2.52–2.48(3H, m).

b) (1S,2R)-4'-(2-Hydroxy-1-methyl-4-pyridin-3-yl-butoxy)-6-methylbiphenyl-3-carboxylic acid methylamide Prepared according to the method described in Example 12b) from (1S,2R)-4-[2-hydroxy-1-methyl-4-pyridin-3-ylbutoxy]benzeneboronic acid (0.20 g, Example 33 (0.290 g), 3-bromo-4-methylbenzoic acid, methyl amide (0.30 g), 2M aqueous sodium carbonate (0.66 ml) and tetrakis (triphenylphosphine)palladium(0) (0.038 g) in ethanol (3 ml). The reaction mixture was heated at 90° C. for 4 hours. After cooling, the solution was concentrated under reduced pressure, taken up in ethanol and concentrated again (twice). The residue was triturated with acetone and then filtered through silica gel. The filtrate was concentrated under reduced pressure, dissolved in dichloromethane, filtered and purified by normal-phase HPLC eluting with a gradient of 0–25% ethanol in dichloromethane to give an oil, which was further purified by column chromatography over silica gel eluting with ethyl acetate:ethanol (9:1) to give the title compound as a foam(0.20 g).

MS (APCI) 405 (M+H)+

$^1$H NMR (DMSO) 8.40(3H, m); 7.73–7.6(3H, m); 7.39–7.25(4H, m); 6.98(2H, d); 5.00(1H, d); 4.33(1H, t); 3.56(1H, d); 2.87–2.6(5H, m); 2.27(3H, s); 1.95–1.82(1H, m); 1.7–1.6(1H, m); 1.25(3H, d).

EXAMPLE 78

(1S,2R)-4-Methyl-4'-(2-hydroxy-1-methyl-4-pyridin-3-yl-butoxy)biphenyl-3-sulfonic acid amide

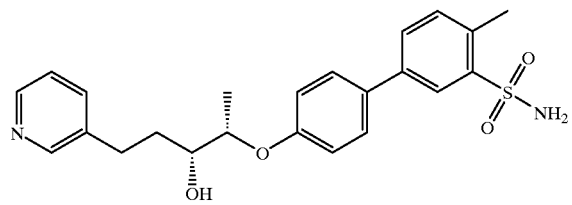

a) 5-Bromo-2-methylaniline

A slurry of 5-bromo-2-methylnitrobenzene (3.00 g), iron powder (3.11 g), and ammonium chloride (2.97 g), in 3:1 ethanol : water (50 ml) was heated at reflux temperature for 1 hour. The mixture was poured into 10% aqueous sodium hydroxide and filtered through Celite®. The filtrate was then extracted with ethyl acetate, the extracts washed with brine, dried over magnesium sulfate, filtered and evaporated to afford the subtitle compound as an oil (2.64 g).

$^1$H NMR (CDCl$_3$) 6.89 (1H, d); 6.79(2H, m); 3.64(2H, br.s); 2.10(3H, s).

b) 5-Bromo-2-methylbenzenesulfonic acid amide

Prepared by the method of Example 69a) using 5-bromo-2-methylaniline (2.60 g, Example 78a)), sodium nitrite (1.05 g), concentrated hydrochloric acid (20 ml), anhydrous magnesium chloride (2.6 g), acetic acid saturated with sulfur dioxide (50 ml) and containing copper (II) chloride (0.37 g). The normal work-up and subsequent treatment with ammonium hydroxide (50 ml) followed by the same work-up afforded the subtitle compound as a solid (0.42 g).

MS(APCI) 248/250 (M−H)+

$^1$H NMR (CDCl$_3$) 8.15(1H, s); 7.58(1H, d); 7.20(1H, d); 4.86(2H, br.s); 2.63(3H, s).

c) (1S,2R)-4-Methyl-4'-(2-hydroxy-1-methyl-4-pyridin-3-yl-butoxy)biphenyl-3-sulfonic acid amide Prepared according to the method described in Example 12b) from (1S,2R)-4-(2-hydroxy-1-methyl-4-pyridin-3-ylbutoxy)benzeneboronic acid (0.2g, Example 33), 5-bromo-2-methylbenzenesulfonic acid amide (1.7 g, Example 78a), ethanol (3 ml), 2M aqueous sodium carbonate (0.7 ml) and tetrakis(triphenylphosphine)palladium (0) (0.03 g) with heating at 80° C. for 3 hours. After work-up, the residue was purified by normal-phase HPLC eluting with a gradient of 0–25% ethanol in dichloromethane to give the title compound as a foam (0.10 g).

MS (APCl) 427 (M+H)+

NMR (CDCl$_3$) 8.50(1H, s); 8.45(1H, d); 8.20(1H, s); 7.63(1H, d); 7.56(1H, d); 7.50(2H, d); 7.37(1H, d); 7.24–7.21(1H, m); 6.95(2H, d); 4.95(2H, s); 4.42–4.38(1H, m); 3.87(1H, br.s); 2.98–2.91(1H, m); 2.77–2.71(4H, m); 2.26(1H, br.s); 1.94–1.79(2H, m); 1.31(3H, d).

EXAMPLE 79

(1S,2R)-3-Methyl-4'-(2-hydroxy-1-methyl-4-pyridin-3-yl-butoxy)biphenyl-4-sulfonic acid amide

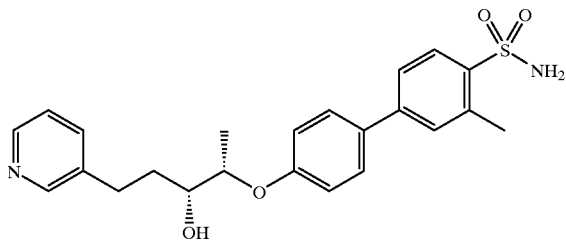

a) 4-Bromo-2-methylbenzenesulfonic acid amide

Prepared by the method of Example 69a) using 3-bromo-4-methylaniline (2.60 g, Example 78a)), sodium nitrite (1.05 g), concentrated hydrochloric acid (20 ml), anhydrous magnesium chloride (2.6 g), acetic acid saturated with sulfur dioxide (50 ml) and copper (II) chloride (0.37 g). The normal work-up and subsequent treatment with ammonium hydroxide (50 ml) followed by the same work-up afforded the subtitle compound as a solid (1.51 g).

m.p. 179–180° C.

MS(APCI) 250/251 (M−H+)

$^1$H NMR (CDCl$_3$) 7.76(1H, d); 7.64(1H, s); 7.59(1H, d); 7.49(2H, br.s); 2.57(3H, s).

b) (1S,2R)-3-Methyl-4'-(2-hydroxy-1-methyl-4-pyridin-3-yl-butoxy)biphenyl-4-sulfonic acid amide Prepared according to the method described in Example 12b) from (1S,2R)-4-(2-hydroxy-1-methyl-4-pyridin-3-ylbutoxy)benzeneboronic acid (0.2 g, Example 33), 4-bromo-2-methylbenzenesulfonic acid amide (1.7 g, Example 79a), ethanol (3 ml), 2M aqueous sodium carbonate (0.7 ml) and tetrakis(triphenylphosphine)palladium (0) (0.03 g) with heating at 80° C. for 3 hours. After work-up, the residue was purified by normal-phase HPLC eluting with a gradient of 0–25% ethanol in dichloromethane to give the title compound as a foam (0.13 g).

MS (APCI) 427 (M+H)+

$^1$H NMR (CDCl$_3$) 8.52(1H, s); 8.46(1H, d); 8.05(1H, d); 7.57–7.46(5H, m); 7.26–7.21(1H, m); 6.97(2H, d); 4.83(2H, s); 4.42–4.39(1H, m); 3.92–3.83(1H, m); 3.01–2.91(1H, m); 2.79–2.69(4H, m); 2.17–2.14(1H, m); 1.90–1.82(2H, m); 1.32(3H, d).

EXAMPLE 80

(1S,2R)-3-Fluoro-4'-(2-hydroxy-1-methyl-4-pyridin-3-yl-butoxy)biphenyl-4-sulfonic acid amide

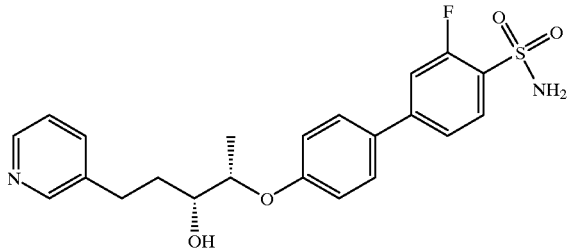

b) (1S,2R)-3-Fluoro-4'-(2-hydroxy-1-methyl-4-pyridin-3-yl-butoxy)biphenyl-4-sulfonic acid amide Prepared according to the method described in Example 12b) from 4-[(2S,3R)-5-(pyridin-3-yl)-3-hydroxypent-2-yloxy]benzeneboronic acid (0.20 g, Example 33), 4-bromo-2-fluorophenylsulfonic acid amide (0.20 g), ethanol (3 ml), 2M aqueous sodium carbonate (1.0 ml) and tetrakis(triphenylphosphine)palladium (0) (0.03 g) with heating at 90° C. for 3 hours. After work-up, the residue was purified by normal-phase HPLC eluting with a gradient of 0–25% ethanol in dichloromethane, followed by recrystalisation from aqueous ethanol, to give the title compound as a solid (0.11 g).

m.p. 178.5–179.5° C.

MS (APCI) 431 (M+H)+

$^1$H NMR (CDCl$_3$) 8.44(1H, s); 8.39(1H, d); 7.80(1H, dd); 7.65(7H, m); 7.30(1H, dd); 7.03(2H, d); 5.01(1H, d); 4.37 (1H, m); 3.55(1H, m); 2.80(1H, m); 2.65(1H, m); 1.84(1H, m); 1.64(1H, m); 1.24(3H, d).

EXAMPLE 81

(1S,2R)-3-Fluoro-4'-(2-hydroxy-1-methyl-4-pyridin-3-yl-butoxy)-biphenyl-4-carbonitrile

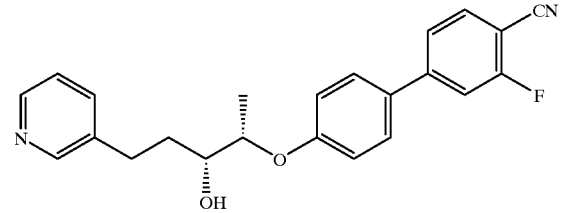

Prepared according to the method described in Example 12b) from (1S,2R)-4-(2-hydroxy-1-methyl-4-pyridin-3-ylbutoxy)benzeneboronic acid (0.20 g, Example 33), 4-bromo-2-fluorobenzonitrile (0.16 g), 2M aqueous sodium carbonate (0.76 ml) and tetrakis(triphenylphosphine) palladium (0) (0.03 g) in ethanol (3 ml) with heating at 90° C. for 4 hours. After work up, the residue was purified by normal-phase HPLC eluting with a gradient of 0–25% ethanol in dichloromethane to give the title compound as a gum (0.14 g)

MS(APCI) 377/378 (M+H)+

¹H NMR(CDCl₃) 8.51(1H, s); 8.46(1H, d); 7.64(1H, dd); 7.24(1H, dd); 7.52(3H, m); 7.43(1H, dd); 7.37(1H, dd); 6.98(2H, d); 4.41(1H, m); 3.85(1H, m); 2.96(1H, m); 2.75 (1H, m); 2.25(1H, br.s); 1.87(2H, m); 1.32(3H, d).

EXAMPLE 82

(1S,2R)-4-Fluoro-4'-(2-hydroxy-1-methyl-4-pyridin-3-yl-butoxy)-biphenyl-3-carboxylic acid amide, hydrochloride salt

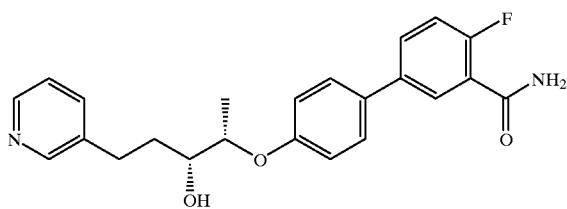

a) 2-Fluoro-5-bromobenzamide

5-Bromo-2-fluorobenzonitrile (0.370 g) was heated at 110° C. for 1 hour in concentrated sulfuric acid (10 ml). After cooling, the reaction was diluted with ice-cold water and the slurry was extracted into ethyl acetate, dried over anhydrous magnesium sulfate, filtered and evaporated to afford the sub-title compound as a solid (0.328 g).

¹H NMR (CDCl₃) 8.26 (1H, m); 7.61 (1H, m); 7.05 (1H, m); 6.64 (1H, bs); 5.89 (1H, br.s).

b) (2S, 3R)-2-(4-fluoro-3'carboxamide-4-biphenyloxy)-5-(pyridin-3-yl)-pentan-3-ol, hydrochloride salt Prepared according to the method described in Example 12b) from (1S,2R)-4-[2-(tert-butyldimethylsilanyloxy)-1-methyl-4-pyridin-3-ylbutoxy]benzeneboronic acid (0.200 g, Example 11), 5-bromo-2-fluorobenzamide (0.158 g, Example 82a), ethanol (3 ml), 2M aqueous sodium carbonate (0.48 ml) and tetrakis(triphenylphosphine)palladium (0) (0.030 g), heating at 60° C. for 8 hours. After cooling, the reaction mixture was evaporated and azeotroped with ethanol. The residue was taken up in acetone, filtered through a pad of silica gel and evaporated to give an oil which was stirred 1 hour at room temperature in a mixture of methanol (4 ml) and concentrated hydrochloric acid (1 ml). The reaction was cooled with an ice-bath, diluted with water and basified to pH 9 by careful addition of sodium bicarbonate solution. The product was extracted into ethyl acetate, the organic phases were combined, dried over anhydrous magnesium sulfate, filtered and evaporated. The residue was purified by normal-phase HPLC eluting with a gradient of 0–10% ethanol in dichloromethane to give the title compound as a foam (0.040 g).

MS (APCI) 395 (M+H)+

¹H NMR (CDCl₃) 8.51 (1H, s); 8.46 (1H, m); 8.30 (1H, m); 7.66 (1H, m); 7.56 (1H, m); 7.50 (2H, d); 7.20 (2H, m); 6.97 (2H, d); 6.74 (1H, br.m), 5.98 (1H, br.s); 4.39(1H, m); 3.87 (1H, m); 2.96 (1H, m); 2.74 (1H, m); 2.44 (1H, br.s); 2.17 (1H, s); 1.84 (2H, m); 1.31 (3H, d).

EXAMPLE 85

(1S,2R)-3-[6-(2-Hydroxy-1-methyl-4-pyridin-3-yl-butoxy)naphthalen-2-yl]-N-methyl-propionamide

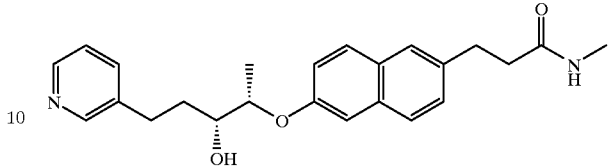

a) (2S,3R)-3-[6-(3-Hydroxy)-5-(pyridin-3-yl)pent-2-yloxy)naphth-2-yl]propenoic acid, methyl ester Prepared according to the method described in Example 40a) from (2S,3R)-4-(6-bromonaphthalen-2-yloxy)-1-pyridin-3-yl-pentan-3-ol (0.68 g Example 10), methylacrylate (0.76 g), palladium acetate (0.04 g), tri-o-tolylphosphine (0.11 g) and triethylamine (2 ml) in acetonitrile (10 ml). After work up crude material was purified by flash column chromatography over silica eluting with 20% acetone in isohexane followed by 50% acetone in isohexane to give the sub-title compound as an oil (0.73 g).

MS (APCI) 392 (M+H)+

NMR (CDCl₃) 8.52(1H, d); 8.46(1H, dd); 7.85(1H, s); 7.79(1H, d); 7.73(1H, d); 7.64(1H, dd); 7.61(1H, dd); 7.56 (1H, d); 7.24–7.20(1H, m); 7.16(1H, dd); 7.12(1H, dd); 6.52(1H, d) 4.53–4.50(1H, m); 3.94–3.88(1H, m); 3.83(3H, s); 2.99–2.92(1H, m); 2.81–2.73(1H, m); 2.18(1H, br.s); 1.92–1.85(2H, m); 1.36(3H, d).

b) (2S,3R)-3-[6-(3-Hydroxy)-5-(pyridin-3-yl)pent-2-yloxy)naphth-2-yl2]propanoic acid, methyl ester Prepared according to the method described in Example 40b) from (2S,3R)-3-[6-(3-hydroxy)-5-(pyridin-3-yl)pent-2-yloxy)naphth-2-yl]propenoic acid, methyl ester(0.73 g, Example 84b)), 10% palladium on carbon (0.2 g) and ethanol (50 ml). After work up crude material was purified by flash column chromatography over silica eluting with 5% ethanol in dichloromethane to give an oil (0.57 g).

MS (APCI) 394 (M+H)+

H NMR (CDCl₃) 8.52(1H, s); 8.46(1H, d); 7.69(1H, d); 7.63(1H, d); 7.56(2H, dd); 7.30(1H, d); 7.24–7.21(1H, m); 7.10(2H, d); 4.49–4.48(1H, m); 3.98–3.87(1H, m); 3.67(3H, s); 3.08(2H, t); 3.09–3.06(1H, m); 2.72–2.69(3H, m); 1.80 (1H, br.s); 1.89–1.85(2H, m); 1.35(3H, d).

c) (1S,2R)-3-[6-(2-Hydroxy-1-methyl-4-pyridin-3-yl-butoxy)naphthalen-2-yl]-N-methyl-propionamide Trimethylaluminium (2.9 ml, 2.0M solution in toluene) was cautiously added to a suspension of methylamine hydrochloride (0.39 g) in toluene (6 ml) at 0° C., with stirring, under nitrogen. During the addition the temperature of the reaction was kept between 0° C. and 5° C. The reaction mixture was then left to come to room temperature for approximately 1 hour. This aluminium/amide reagent was added to a solution of (2S,3R)-3-[6-(3-hydroxy)-5-(pyridin-3-yl)pent-2-yloxy)naphth-2-yl]propanoic acid, methyl ester (0.57 g, Example 84b) in toluene (20 ml) and heated at reflux temperature, under nitrogen, for 16 hours. After cooling, the reaction mixture was acidified with 2M hydrochloric acid and stirred for 1 hour. The aqueous layer was separated and basified by addition of a saturated solution of sodium bicarbonate then extracted with ethyl acetate (3×100 ml). The ethyl acetate fractions were combined, washed with brine and dried over anhydrous magnesium sulfate. After filtration, solvent was removed by evaporation under reduced pressure and the residue purified by flash column chromatography over silica eluting with 5% ethanol in dichloromethane to give the title compound as a solid (0.2 g).

m.p. 68–70° C.

MS (APCI) 393 (M+H)+

$^1$H NMR (CDCl$_3$) 8.51(1H, s); 8.46(1H, d); 7.68(1H, d); 7.63(1H, d); 7.55(2H, d); 7.30(1H, dd); 7.24–7.20(1H, m); 7.12–7.08(2H, m); 5.32(1H, br.s); 4.50–4.47(1H, m);3.91–3.88(1H, m); 3.10(2H, t); 3.01–2.90(1H, m); 2.85–2.70(4H, m); 2.53(2H, t); 2.21(1H, d); 1.90–1.84(2H, m); 1.34(3H, d).

EXAMPLE 86

3-Cyano-4-fluorobenzeneboronic Acid

A solution of n-butyllithium (5.6 ml, 2.5M in hexanes) was added over a 20 minute period to a solution of 5-bromo-2-fluorobenzonitrile and triisopropylborate (3.46 ml) in tetrahydrofuran (10 ml) at −78° C. The resulting solution was stirred at −78° C. for 30 minutes and then quenched by the addition of a 2M hydrochloric acid (20 ml) and extracted into ethyl acetate. The combined extracts were dried over anhydrous magnesium sulfate, filtered and concentrated. The residue was purified by trituration using diethyl ether: hexane 1:2 to afford the sub-title compound as a solid (1.24 g).

m.p.>250° C.

MS (APCI -ve) 164 (M–H)−

$^1$H NMR (DMSO/D$_2$O) 8.20 (1H, dd); 8.16–8.12 (1H, m); 7.53–7.49 (1H, m).

EXAMPLE 87

(1S,2R)-4-Fluoro-4'-(1-ethyl-2-hydroxy-4-pyridin-3-ylbutoxy)biphenyl-3-carbonitrile

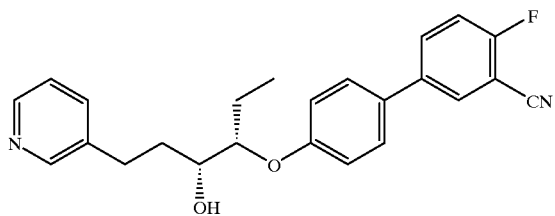

a) (2S)-2-(4-Bromophenoxy)butanoic acid, methyl ester

Prepared according to the method described in Example 1a) from diethylazodicarboxylate (7.8 g), 4-bromophenol (7.8 g), triphenylphosphine (11.8 g), and R-2-hydroxybutanoic acid, methyl ester (5.31g, Tetrahedron, 35, 1601) in anhydrous tetrahydrofuran. After work up crude material was purified by flash column chromatography over silica eluting with 30% dichloromethane in isohexane to give the sub-title compound as an oil (7.53 g). $^1$H NMR (CDCl$_3$) 7.37(2H, dt); 6.76(2H, dt); 4.52(1H, t); 3.75(3H, s); 2.03–1.94(2H, m); 1.07(3H, t).

b) (2S)-2-(4Bromophenoxy)-1-butanol

Prepared according to the method described in Example 4b) from (2S)-2-(4-bromophenoxy)butanoic acid, methyl ester (7.53 g, Example 87a)) and sodium borohydride (1.09 g) in ethanol (100 ml). After work up, crude material was purified by flash column chromatography over silica eluting with dichloromethane to give the sub-title compound as an oil (5.24 g).

$^1$H NMR (CDCl$_3$) 7.37(2H, dt); 6.83(2H, dt); 4.28–4.21 (1H, m); 3.85–3.70(2H, m); 1.85–1.81(1H, m); 1.77–1.57 (2H, m); 0.96(3H, t).

c) (3RS, 4S)-4-(4-Bromophenoxy)-1-pyridin-3-yl-hex-1-yn-3-ol

Freshly activated (dried in oven at 300° C.) powdered molecular sieves (20 g, 3 Å, <5 micron) were added to (2S)-2-(4-bromophenoxy)-1-butanol (5.24 g, Example 87b)) and pyridinium dichromate (12.07 g) in anhydrous dichloromethane (200 ml). This mixture was treated with anhydrous acetic acid (2 drops) and stirred under nitrogen for 2 hours. Celite® (10 g) was added to the reaction mixture which was stirred for 20 minutes. Isohexane (100 ml) was added to this and the mixture filtered. The filtrate was concentrated under reduced pressure and the residue obtained was triturated in diethyl ether. This was filtered through anhydrous magnesium sulfate and the filtrate concentrated under reduced pressure. The residue obtained was assumed to be (2S)-2-(4-bromophenoxy)-1-butanal and dissolved in anhydrous tetrahydrofuran (40 ml). n-Butyl-lithium (5.88 ml, 2.5M solution in hexanes) was added dropwise to a solution of pyridin-3-ylacetylene (1.6g, J. Amer. Chem. Soc. 1935, 57, 1284) in anhydrous tetrahydrofuran (80 ml) at −70° C., under nitrogen. After stirring for 20 minutes the solution of the (2S)-2-(4-bromophenoxy)-1-butanal in tetrahydrofuran was added dropwise, maintaining the reaction temperature at −70° C.. The reaction mixture was then allowed to warm slowly to 0° C. and poured into brine (200 ml). The organic layer was separated and the aqueous layer was extracted with ethyl acetate. The organic fractions were combined and dried over anhydrous magnesium sulfate. After filtration, the filtrate was concentrated under reduced pressure to give an oil which was purified by flash column chromatography over silica eluting with isohexane : ethyl acetate (2:1). This gave the sub-title compound as an oil (3.42 g).

MS (APCI) 348 (M+H)+

$^1$H NMR (CDCl$_3$) 8.70(1H, dd); 8.51(1H, dd); 7.69–7.65 (1H, m); 7.40–7.36(2H, m); 7.27–7.23(1H, m); 6.93–6.88 (2H, m); 4.81(1H, t); 4.37–4.33(1H, m); 3.24(1H, d); 1.94–189(2H, m); 1.08–1.01(3H, m).

d) (3R,4S)-4-(4-Bromophenoxy)-1-pyridin-3-yl-hexan-3-ol

Prepared according to the method described in Example 1d) from (3RS,4S)-4-(4-bromophenoxy)-1-pyridin-3-yl-hex-1-yn-3-ol (3.42 g, Example 87c)) and 5% rhodium on carbon (0.5 g) in ethyl acetate (100 ml). After work up crude material was purified by flash column chromatography over silica eluting with ethyl acetate to give a mixture of diastereomers. The mixture was separated by normal-phase HPLC eluting with 2% propan-2-ol in dichloromethane to give the sub-title compound as the second eluting, major diastereomer (2 g).

MS (APCI) 350 (M+H)+

$^1$H NMR (CDCl$_3$) 8.48(1H, s); 8.45(1H, d); 7.52(1H, dt); 7.38–7.34(2H, m); 7.23–720(1H, m); 6.82–6.77(2H, m); 4.15–4.10(1H, m); 3.83(1H, br. s); 2.96–2.89(1H, m); 2.73–2.66(1H, m); 2.08(1H, br. s); 1.89–1.61(4H, m); 0.95 (3H, t).

e) (1S,2R)-4-Fluoro-4-(1-ethyl-2-hydroxy-4-pyridin-3-ylbutoxy)biphenyl-3-carbonitrile Prepared according to the method described in Example 12b) from (3R, 4S)-4-(4-bromophenoxy)-1-pyridin-3-yl-hexan-3-ol (0.3 g, Example 87d)), 3-cyano-4-fluorobenzeneboronic acid (0.17 g, Example 86), ethanol (3.0 ml), 2M aqueous sodium carbonate (0.5 ml) and tetrakis (triphenylphosphine)palladium (0) (0.03 g) with heating at 100° C. for 4 hours. After work up, the residue was purified by flash column chromatography over silica eluting with isohexane: acetone (2:1) to give the title compound as an oil (0.17 g).

MS (APCI) 391 (M+H)+

¹H NMR (CDCl₃) 8.50(1H, s); 8.46(1H, d); 7.75–7.70 (2H, m); 7.57(1H, d); 7.42(2H, d); 7.28–7.21(2H, m); 7.00 (2H, d); 4.27–4.23(1H, m); 3.89–3.85(1H, m); 2.98–291 (1H, m); 2.76–2.68(1H, m); 2.05(1H, br. s); 1.91–1.67(4H, m); 0.99(3H, t).

EXAMPLE 88

(1S,2R)-4'-[1-Ethyl-2-hydroxy-4-pyridin-3-yl-butoxy]-4-fluorobiphenyl-3-sulfonic acid amide

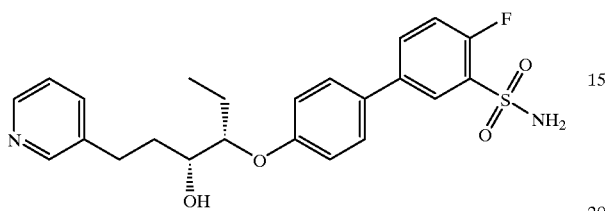

a) (3R,4S)-3-[4-(4-Bromophenoxy)-3-(t-butyldimethylsilanyloxy)hexyl]pyridine

To a solution of (3R,4S)-4-(4-bromophenoxy)-1-pyridin-3-yl-hexan-3-ol (1.34 g, Example 87d)) in dry N,N-dimethylformamide (30 ml) was added tertbutyldimethylsilyl chloride (0.80 g) and imidazole (0.77 g) and the resulting solution heated at 50° C. for 20 hours. The solution was concentrated in vacuo. The residue was made basic by addition of saturated sodium hydrogen carbonate solution and extracted with ethyl acetate. The combined extracts were dried over anhydrous magnesium sulfate, filtered and concentrated under reduced pressure. The residue was purified by column chromatography over silica eluting with ethyl acetate:isohexane (1:1) to give the sub-title compound as an oil (0.71 g).

MS(APCI) 466(M+H)+

¹H NMR(CDCl₃) 8.43(1H, dd); 8.40(1H, d); 7.41–7.33 (1H, m); 7.34(2H, d); 7.20–7.16(1H, m); 6.76(2H, d); 4.11–4.08(1H, m); 3.92–3.90(1H, m); 2.88–2.78(2H, m); 198–171(4H, m); (4H, m); 0.96(3H, t); 0.91(9H, s); 0.06 (6H, d).

b) (1S,2R)-4-[2-(t-Butyldimethylsilanyloxy)-1-ethyl-4-pyridin-3-yl-butoxy]benzeneboronic acid Prepared according to the method as described in Example 5b) from (3R,4S)-3-[4-(4-bromophenoxy)-3-(t-butyldimethylsilanyloxy)hexyl]pyridine (0.71 g, Example 88a)), tertbutyl lithium (1.80 ml, 1.7M in hexanes) and tri-isopropylborate (0.74 ml) in dry tetrahydrofuran (25 ml). After work up, the residue was purified by column chromatography eluting with a gradient 0–25% ethanol in ethyl acetate to give the sub-title compound as a foam (0.41 g).

MS(APCI) 430(M+H)+

¹H NMR(CDCl₃) 8.53–8.51(2H, m); 7.95(2H, d); 7.45–7.42(1H, m); 7.22–7.18(1H, m); 6.89(2H, d); 4.20–4.16(1H, m); 3.98–3.93(1H, m); 3.76–3.69(1H, m); 2.74–2.61(2H, m); 1.98–1.91(1H, m); 1.82–1.73(3H, m); 1.60(1H, br.s); 0.98(3H, t); 0.92(9H, s); 0.02(6H,d).

c) (1S,2R)-4'-[1-Ethyl-2-hydroxy-4-pyridin-3-yl-butoxyl]-4-fluorobiphenyl-3-sulfonic acid amide Prepared according to the method described in Example 12b) from from (3R,4S)-3-[4-(4-Bromophenoxy)-3-(t-butyldimethylsilanyloxy)hexyl]pyridine (0.20 g, Example 88b)), 2-fluoro-5-bromophenylsulfonamide (0.177 g, Example 35a)), 2M aqueous sodium carbonate (0.54 ml) and tetrakis(triphenylphosphine)palladium (0) (0.014 g) in ethanol (3 ml) with heating at 90 ° C. for 4 hours. The residue was purified by column chromatography over silica eluting with ethyl acetate to give the title compound as a foam (0.14 g).

MS(APCI) 445(M+H)+

¹H NMR(CDCl₃) 8.49(1H, d); 8.45(1H, dd); 8.05(1H, dt); 7.74–7.68(1H, m); 7.55–7.52(1H, m); 7.46(2H, d); 7.30–7.21(2H, m); 6.98(2H, d); 5.08(2H, s); 4.23–421(1H, m); 3.96–3.85(1H, m); 2.95–2.86(1H, m); 2.74–2.64(1H, m); 1.96(1H, d); 1.91–1.83(4H, m); 0.98(3H, t).

EXAMPLE 89

(1S,2R)-3-Chloro-4'-(1-ethyl-2-hydroxy-4-pyridin-3-ylbutoxy)biphenyl-4-carbonitrile

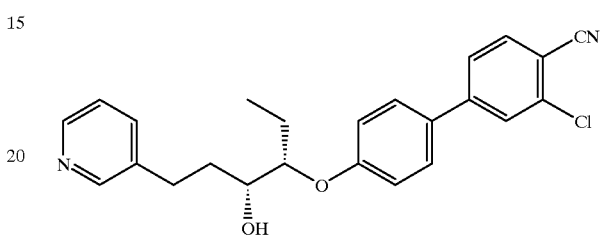

Prepared according to the method described in Example 12b) from (1S,2R)-4-[2-(tertbutyldimethylsilanyloxy)-1-ethyl-4-pyridin-3-yl-butoxy]benzeneboronic acid (0.18 g, Example 88b)), 4-bromo-2-chlorobenzonitrile (0.18 g), 2M aqueous sodium carbonate (0.48 ml) and tetrakis (triphenylphosphine)palladium (0) (0.012 g) in ethanol (3 ml) with heating at 90 ° C. for 4 hours. The residue was purified by column chromatography eluting with a gradient of 50–1 00% ethyl acetate in isohexane to give the title compound as a solid (0.125 g).

m.p. 99–100° C.

MS(APCI)407(M+H)+

¹H NMR(CDCl₃) 8.48(1H, d); 8.45(1H, dd); 7.70–7.56 (2H, m); 7.56–7.48(2H, m); 7.51(2H, d); 7.24–7.20(1H, m); 7.0(2H, d); 4.27–4.25(1H, m); 3.86–3.80(1H, m); 2.94–2.92 (1H, m); 2.74–2.69(1H, m); 2.12(1H, d); 1.92–1.73(4H, m); 0.98(3H, t).

Pharmacological Activity

The pharmacological activity of the compounds of the invention may be tested by the method of E. Wells et al, 'Characterization of primate bronchoalveolar mast cells: II-inhibition of histamine, LTC₄ and PGD₂ release from primate bronchoalveolar mast cells and a comparison with rat peritoneal mast cells', *J. Immunol.*, vol. 137, 3941, 1986.

The compounds of examples 1 to 89 were tested and found to inhibit histamine release at a concentration of less than $10^{31\ 5}$ M ($IC_{50}$).

What is claimed is:

1. A compound of formula I:

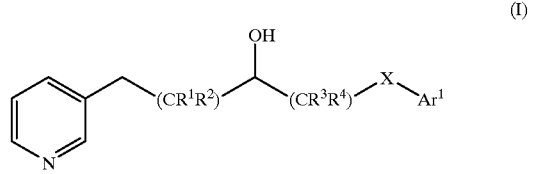

(I)

wherein:

X is O or S;

83

R¹ and R² are independently hydrogen, $C_{1-6}$ alkyl or $C_{3-6}$ cycloalkyl or R¹ and R² together with the carbon atom to which they are attached form a $C_{3-6}$ cycloalkyl group;

R³ is hydrogen, and R⁴ is $C_{1-6}$ alkyl or $C_{3-6}$ cycloalkyl or R³ and R⁴ together with the carbon atom to which they are attached form a $C_{3-6}$ cycloalkyl group;

Ar¹ is indanyl, tetrahydronaphthyl, naphthyl, phenyl, $C_{7-9}$ alkylphenyl or biphenyl, which latter four groups can be optionally substituted by one or more groups selected from halo, nitro, cyano, pyridyl, thiazinyl, $C_{1-10}$ alkyl (optionally substituted by one or more fluorine is atoms), —Y—OR⁵, —Y—NR⁶C(O)NR⁷—R⁸,—O—Z—C(O)NR⁷R⁸, —O—Y—C(S)NR⁷R⁸, —Y—C(O)NR⁷R⁸, —Y—SO₂NR⁷R⁸, —Y—NR⁷R⁸, —Y—OC(O)NR⁷R⁸, —Y—C(S)NR⁷R⁸, —Y—C(O)R⁹, —Y—OC(O)R⁹, —Y—CO₂R⁹, —Y—NR¹⁰C(O)NR¹¹—Z—R¹², SO₂NR¹⁰C(O)NR⁷R⁸, —Y—SO₂NHNR⁷R⁸, —Y—C(O)NR¹¹—Z—R¹², —Y—C(S)NR¹¹—Z—R¹², —Y—N(R¹⁰)SO₂R¹¹, —Y—N(R¹⁰)C(O)R¹¹ or —Y—N(R¹⁰)CO₂R¹¹;

where:

Y is a bond, $C_{1-6}$ alkylene or $C_{2-6}$ alkenylene;

R⁷ and R⁸ are independently hydrogen or $C_{1-6}$ alkyl or together with the nitrogen atom to which they are attached form an optionally substituted 5- to 7-membered heterocyclic ring optionally containing a further heteroatom selected from nitrogen, oxygen or sulfur; R⁵, R⁶, R⁹, R¹⁰ and R¹¹ are independently hydrogen or $C_{1-0}$ alkyl (optionally substituted by one or more fluorine atoms);

Z is $C_{1-6}$ alkylene; and

R¹² is a group NR¹⁰ C(O)R¹¹, NR¹⁰CO₂R¹¹, OR⁵, NR⁷R⁸ or CO₂R¹³ where R⁵, R⁷, R⁸, R¹⁰ and R¹¹ are as defined above and R¹³ is hydrogen, $C_{1-6}$ alkyl, $C_{1-6}$ alkylaryl or aryl optionally substituted by hydroxy, or a salt or solvate thereof.

2. A compound according to claim 1 in which X is O.

3. A compound according to claim 1 in which R¹ and R² are both hydrogen.

4. A compound according to any one of claims in which R³ is hydrogen and R⁴ is $C_{1-6}$ alkyl or R³ together with R⁴ forms a cyclopropyl group.

5. A compound according to any one of claims 1 in which Ar¹ is naphthyl or biphenyl.

6. A compound according to any one of claims 1 in which Ar¹ is biphenyl optionally substituted by one or more substituents selected from halo, cyano, methyl or SO₂NR⁷R⁸.

7. A compound according to claim 1 which is:

(3R,4R)-(Biphenyl-4-yloxy)- 1-pyridin-3-yl-pentan-3-ol,
(3S,4R)-4-(biphenyl-4-yloxy)-1-pyridin-3-yl-pentan-3-ol,
(3R,4S)-4-(Biphenyl-4-yloxy)- 1-pyridin-3-yl-pentan-3-ol.
(3S,4S)-4-(Biphenyl-4-yloxy)- 1-pyridin-3-yl-pentan-3-ol,
(1S,2R)-4'-(2-Hydroxy-1-methyl-4-pyridin-3-ylbutoxy) biphenyl-3-carbonitrile,
(1S,2S)-4'-(2-Hydroxy-1-methyl-4-pyridin-3-ylbutoxy) biphenyl-3-carbonitrile,
(1S,2R)-4'-(2-Hydroxy-1-methyl-4-pyridin-3-yl-butoxy)-biphenyl-3-sulfonic acid amide,
(1S,2S)-4'-(2-Hydroxy-1-methyl-4-pyridin-3-yl-butoxy)-biphenyl-3-sulfonic acid amide,
(3R,4S)-4-(3'-Chlorobiphenyl-4-yloxy)-1-pyridin-3-yl-pentan-3-ol,
(3S,4S)-4-(3'-Chlorobiphenyl-4-yloxy)-1-pyridin-3-yl-pentan-3-ol,

84

(3R,4S)-4-(4'-Fluoro-biphenyl-4-yloxy)-1-pyridin-3-yl-pentan-3-ol,
(3S,4R)-4-(4'-Fluoro-biphenyl-4-yloxy)-1-pyridin-3-yl-pentan-3-ol,
(3R,4S)-4-(Biphenyl-4-yloxy)-5-methyl-1-pyridin-3-yl-hexan-3-ol,
(±)-1-[1-(Bipheny-4-yloxy)-cyclopropyl]-3-pyridin-3-yl-propan-1-ol,
(2S, 3R)-4-(6-Bromonaphthalen-2-yloxy)-1-pyridin-3-yl-pentan-3-ol,
(2R, 3S)-4-(6-Bromonaphthalen-2-yloxy)-1-pyridin-3-yl-pentan-3-ol,
(1S,2R)-2-[4'(2-Hydroxy-1-methyl-4-pyridin-3-ylbutoxy) biphenyl-3-yl]-N-methylacetamide,
(3R,4S)-4-(4'-Chloro-2'-fluorobiphenyl- 4-yloxy)-1-pyridin-3-yl-pentan-3-ol,
(3R,4S)4-(4'-Chlorobiphenyl-4-yloxy)-1-pyridin-3-yl-pentan-3-ol,
(3R,4S)-4-(5'-methoxy-2'-methylbiphenyl-4-yloxy)-1-pyridin-3-yl-pentan-3-ol,
(3R,4S)-4-(3',4'-Dichlorobiphenyl-4-yloxy)-1-pyridin-3-yl-pentan-3-ol,
(3R,4S)-4-(2',4'-Dichlorobiphenyl-4-yloxy)-1-pyridin-3-yl-pentan-3-ol,
(1S,2R)-4'-(2-Hydroxy-1-methyl-4-pyridin-3-yl-butoxy) biphenyl-3-sulfonic acid methylamide,
(1S,2R)-4'-(2-Hydroxy-1-methyl-4-pyridin-3-yl-butoxy)-2-methyl-biphenyl4-carbonitrile, (1S,2R)-N-[2-Chloro-4'-(2-hydroxy- 1-methyl4-pyridin-3-yl-butoxy)-biphenyl-4-yl]-actamide,
(3R,4S)-4-(4'-Amino-2'-chloro-biphenyl-4-yloxy)-1-pyridin-3-yl-pentan-3-ol,
(1S,2R)-2-[4'(2-Hydroxy-1-methyl-4-pyridin-3-ylbutoxy) biphenyl-4-yl]-N-methylacetamide,
(1S,2R)-2-[4'(2-Hydroxy-1-methyl-4-pyridin-3-ylbutoxy) biphenyl-3-yl]-N,N-dimethylacetamide,
(3R,4S)-4-[3'-(2-Dimethylaminoethyl)biphenyl-4-yloxy]-1-pyridin-3-yl-pentan-3-ol,
(3R,4S)-4-[4-(3'-(Methylaminoethyl)biphenyl-4-yloxy]-1-pyridin-3-yl-pentan-3-ol,
(3R,4S )-4-[4'-(2-Methylaminoethyl)biphenyl-4-yloxy]-1-pyridin-3-yl-pentan-3-ol,
(1S,2R)4'-(2-Hydroxy-1-methyl-4-pyridin-3-ylbutoxy) biphenyl-3-yl-urea,
(3R,4S)-4-(3',4'-Dichlorobiphenyl-4-yloxy)-1-pyridin-3-yl-pentan-3-ol,
(1S,2R)-4-(2-Hydroxy-1-methyl-4-pyridin-3-ylbutoxy) benzeneboronic acid,
(1S,2R)-4'-(2-Hydroxy-1-methyl-4-pyridin-3-yl-butoxy)-3-methyl-biphenyl-4-carbonitrile,
(1S,2R)-4-Fluoro-4'-(2-hydroxy-1-methyl-4-pyridin-3-yl-butoxy)biphenyl-3-sulfonic acid amide, and (1S,2S)-4-Fluoro-4'-(2-hydroxy-1-methyl-4-pyridin-3-yl-butoxy) biphenyl-3-sulfonic acid amide,
(1S,2R)-4-Fluoro4'-(2-hydroxy-1-methyl4-pyridin-3-yl-butoxy)biphenyl-3-carbonitrile,
(1S,2R)-2,5-Difluoro-4'-(2-hydroxy-1-methyl-4-pyridin-3-yl-butoxy)biphenyl4-sulfonic acid amide, (1S,2R)-3-Chloro4'-(2-hydroxy-1-methyl-4-pyridin-3-ylbutoxy)biphenyl-4-carbonitrile,
(1S,2R)-3-[6-(2-Hydroxy-1-methyl-4-pyridin-3-ylbutoxy) naphthalen-2-yl]-N,N-dimethylacrylamide,
(1S,2R)4'-(2-Hydroxy-1-methyl-4-pyridin-3-yl-butoxy) biphenyl-3-N-sulfonamido-N'-isopropyl-urea,
(1S,2R)-3-[6-(2-Hydroxy-1-methyl-4-pyridin-3-y-butoxy)-naphthalen-2-yl]-1-morpholin-4-yl-propan-1-one,
(3R,4S)-4-[6-(3-Morpholin-4-yl-propyl)naphthalen-2-yloxy]-1-pyridin-3-yl-pentan-3ol, (3R,4S)-4-[6-(3-Methylamninopropyl)naphthalen-2-yloxy]-1-pyridin-3-yl-pentan-3-ol,
(1S,2R)-4'-(2-Hydroxy-1-isopropyi4-pyridin-3-yl-butoxy) blphenyl-3-carbonitrile,
(3R,4S)4-(3'-Methanesulfonylbiphenyl-4-yloxy)-1-pyridin-3-yl-pentan-3-ol,
(1S,2R)-4'-(2-Hydroxy-1-methyl-4-pyridin-3-yl-butoxy) biphenl-3-carboxylic acid amide, (1S,2R)-2-[4'-(2-Hydroxy-1-methyl-4-pyridin-3-yl-butoxy)-biphenyl-3-yloxy]acetamide,
(2S,3R)-1-Pyridin-3-yl-4-(2'-trifluoromethoxybiphenyl-4-yloxy)pentan-3-ol,
(1S,2R)-4'-(2-Hydroxy-1-methyl-4-pyridin-3-yl-butoxy)-6-methoxybiphenyl-3-carbonitrile,
(3R,4S)-4-(4'-Chloro-2'-methoxy-5'-methylbiphenyl-4-yloxy)-1-pyridin-3-yl-pentan-3-ol,
(1S,2R)-4'-(2-Hydroxy-1-methyl-4-pyridin-3-yl-butoxy)-biphenyl-3-carboxylic acid methylamide,
(1S,2R)-[4'-(2-Hydroxy-1-methyl-4-pyridin-3-yl-butoxy)-biphenyl-4-yl]acetic acid,
(1S,2R)-N-[4'-(2-Hydroxy-1-methyl-4-pyridin-3-yl-butoxy)-5-trifluoromethyl-biphenyl-2-yl]acetamide,
(1S,2R)-2-[4'-(2-Hydroxy-1-methyl-4-pyridin-3-yl-butoxy)-biphenyl-yl]-N-methylacetamide,
(1S,2R)-N-[4'-(2-Hydroxy-1-methyl-4-pyridin-3yl-butoxy)-2-methylbiphenyl -4-yl]acetamide,
(1S,2R)-N-[4'-(2-Hydroxy-1-methyl-4-pyridin-3-yl-butoxy) biphenyl-3-yl]methanesulfonamide,
(1S,2R)-4'-(2-Hydroxy-1-methyl-4-pyridin-3-yl-butoxy) biphenyl-4-sulfonic acid amide,
(1S,2R)4'-(2-Hydroxy-1-isopropyl-4-pyridin-3-yl-butoxy) biphenyl-3-sulfonic acid amide,
(1S,2R)-[4'-(2-Hydroxy-1-methyl 4-pyridin-3-yl-butoxy) biphenyl-4-yl]urea,
(1S,2R)-4'-(2-Hydroxy-1-methyl-4-pyridin-3-yl-butoxy)-2-methyl-biphenyl-4-carboxylic acid (2-pyrrolidin-1-yl-ethyl)amide,
(1S,2R)4'-(2-Hydroxy-1-methyl-4-pyridin-3-yl-butoxy) biphenyl-3-sufonic acid (2,2.2-trifluoroethyl)amide,
(1S,2R)-1-[4'-(2-Hydroxy-1-methyl-4-pyridin-3-ylbutoxy) -biphenyl4-yl]-3-methylurea,
(1S,2R)-2-[4'-(2-Hydroxy-1-methyl-4-pyridin-3-yl-butoxy)-biphenyl-4-yl]-N-isopropylacetamide,
(1S,2R)-N-Cyclopropyl-2-[4'-(2-hydroxy-1-methyl-4-pyridin-3-yl-butoxy) -biphenyl-4-yl]-acetamide,
(1S,2R)-2-[4'-(2-Hydroxy-1-methyl-4-pyridin-3-yl-butoxy) biphenyl -4-yl]-1-pyrrolidin-1-ylethanone,
(1S,2R)-2-Methyl-4'-(2-hydroxy-1-methyl-4-pyridin-3-yl-butoxy)biphenyl-5-sulfonic acid amide.
(1S,2R)-2,2,2-Trifluoro-N-[4'-(2-hydroxy-1-methyl-4-pyridin-3yl-butoxy) -biphenyl-3-yl]-N-methylacetamide,
(1S,2R)4'-(2-Hydroxy-1-methyl-4-pyridin-3-ylbutoxy) biphenyl-3,4-dicarbonitrile,
(3R,4S)-1-Pyridin-3-yl-4-[3'-(pyrrolidine-1-sulfonyl) biphenyl -4-yloxy]pentan-3-ol,
(1S,2R)-6-Fluoro-4'-(2-hydroxy-1-methyl-4-pyridin-3-yl-butoxy)-biphenyl-3-carbonitrile,
(1S,2R)-4'-(2-Hydroxy-1-methyl-4-pyridin-3-yl-butoxy) -5-trifluoromethyl-biphenyl-3-sulfonic acid amide,
(1S,2R)-N-[3-Fluoro-4'-(2-hydroxy-1-methyl-4-pyridin-3-yi-butoxy) -biphenyl-4-yl]-acetamide,
(1S,2R)-4'-(2-Hydroxy-1-methyl-4-pyridin-3-yl-butoxy) -6-methyl-biphenyl-3-carboxylic acid methylamide,
(1S,2R)-4-Methyl-4'-(2-hydroxy-1-methyl-4-pyridin-3-yl-butoxy)biphenyl-3-sulfonic acid amide,
(1S,2R)-3-Methyl-4'-(2-hydroxy-1-methyl-4-pyridin-3-yl-butoxy)biphenyl-4-sulfonic acid amide,
(1S,2R)-3-Fluoro4'-(2-hydroxy-1-methyl4-pyridin-3-yl-butoxy)biphenyl-4-sulfonic acid amide,
(1S,2R)-3-Fluoro-4'-(2-hydroxy-1-methyl4-pyridin-3-yl-butoxy) -biphenyl-4-carbonitrile,
(1S,2R)4-Fluoro4'-(2-hydroxy-1-methyl-4-pyridin-3-yl-butoxy) -biphenyl-3-carboxylic acid amide,
(1S,2R)-3-[6-(2-Hydroxy-1-methyl-4-pyridin-3-yl-butoxy) naphthalen-2-yl]-N-methyl-propionamide,
(1S,2R)-4-Fluoro-4'-(1-ethyl-2-hydroxy-4-pyridin-3-ylbutoxy) biphenyl-3-carbonitrile,
(1S,2R)4'-[1-Ethyl-2-hydroxy-4-pyridin-3-yl-butoxy]-4-fluorobiphenyl-3-sulfonic acid amide,
(1S,2R)-3-Chloro-4'-(1-ethyl-2-hydroxy-4-pyridin-3-ylbutoxy) biphenyl-4-carbonitrile, or salts or solvates thereof.

8. A pharmaceutical composition comprising a compound of formula I or a salt or solvate thereof as defined in association with a pharmaceutically acceptable adjuvant, diluent or carrier.

9. A process for the preparation of compounds of formula I as defined in claim 1 which comprises:

(a) reduction of a compound of formula (II):

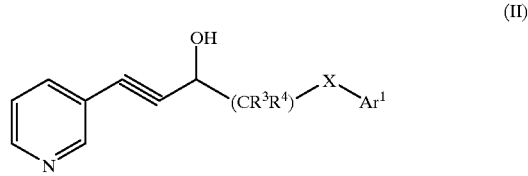

(II)

in which $R^3$, $R^4$, X and $Ar^1$ are as defined in formula (I); or (b) reduction of a compound of formula (III):

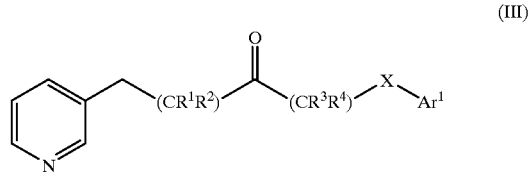

(III)

in which $R^1$, $R^2$, $R^3$, $R^4$, X and $Ar^1$ are as defined in formula (I); or (c) preparation of compounds of formula (I) where $Ar^1$ is a substituted biphenyl group by reaction of a compound of formula (IV):

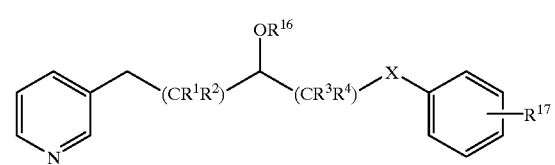

(IV)

with a compound of formula (V):

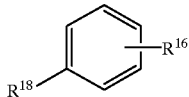
(V)

where X, R$^1$, R$^2$, R$^3$, and R$^4$ are as defined in formula (I), R$^{15}$ is an Ar$^1$ substituent as defined in formula (I), and R$^{16}$ is a suitable hydroxy protecting group, and one of R$^{17}$/R$^1$ is triflate or halo and the other is B(OH)$_2$ or ZnHal, or and optionally thereafter in any order:

removing any protecting groups converting a compound of formula (I) into another compound of formula (I)

forming a pharmaceutically acceptable salt or solvate.

10. A method of treating asthma comprising the step of administering to a patient in need of such treatment an effective amount of a compound of formula (I).

* * * * *